United States Patent
Yeung et al.

(10) Patent No.: US 12,414,685 B2
(45) Date of Patent: Sep. 16, 2025

(54) SURGICAL SYSTEMS AND DEVICES, INCLUDING METHODS FOR CONFIGURING SURGICAL SYSTEMS AND DEVICES, FOR MANAGING POSTPARTUM HEMORRHAGING

(71) Applicant: iEMIS (HK) Limited, Kowloon (HK)

(72) Inventors: Chung Kwong Yeung, Hong Kong (HK); Wing Fai Lam, Quarry Bay (HK); Hon Shing Chan, Kowloon (HK); Biji Sreedhar, Pok Fu Lam (HK)

(73) Assignee: iEMIS (HK) Limited, Kowloon (HK)

( * ) Notice: Subject to any disclaimer, the term of this patent is extended or adjusted under 35 U.S.C. 154(b) by 407 days.

(21) Appl. No.: 18/110,798

(22) Filed: Feb. 16, 2023

(65) Prior Publication Data
US 2024/0277221 A1    Aug. 22, 2024

(51) Int. Cl.
*A61B 1/303* (2006.01)
*A61B 1/015* (2006.01)
*A61B 17/42* (2006.01)

(52) U.S. Cl.
CPC .............. *A61B 1/303* (2013.01); *A61B 1/015* (2013.01); *A61B 17/42* (2013.01); *A61B 2017/4225* (2013.01)

(58) Field of Classification Search
CPC . A61B 1/303; A61B 17/42; A61B 2017/4216; A61B 2017/4241; A61M 2210/1433
See application file for complete search history.

(56) References Cited

U.S. PATENT DOCUMENTS

| 2015/0202411 A1* | 7/2015 | Duncan ................. A61B 17/42 604/544 |
| 2022/0031148 A1* | 2/2022 | Yeung ...................... A61B 1/12 |
| 2023/0241303 A1* | 8/2023 | Greenhalgh .......... A61M 1/915 604/313 |
| 2024/0382235 A1* | 11/2024 | MacLachlan ......... A61M 1/743 |

\* cited by examiner

*Primary Examiner* — Elizabeth Houston
*Assistant Examiner* — Lindsey Bachman

(57) ABSTRACT

Embodiments relate to a hysteroscopic system for managing post-partum hemorrhaging. The hysteroscopic system includes a main assembly and a uterine assembly. The main assembly includes a main channel, a cervical seal member, a first anchoring member, a second anchoring member, and a third anchoring member. The uterine assembly includes a first negative pressure port, a uterine expandable member, and a second negative pressure port.

29 Claims, 33 Drawing Sheets

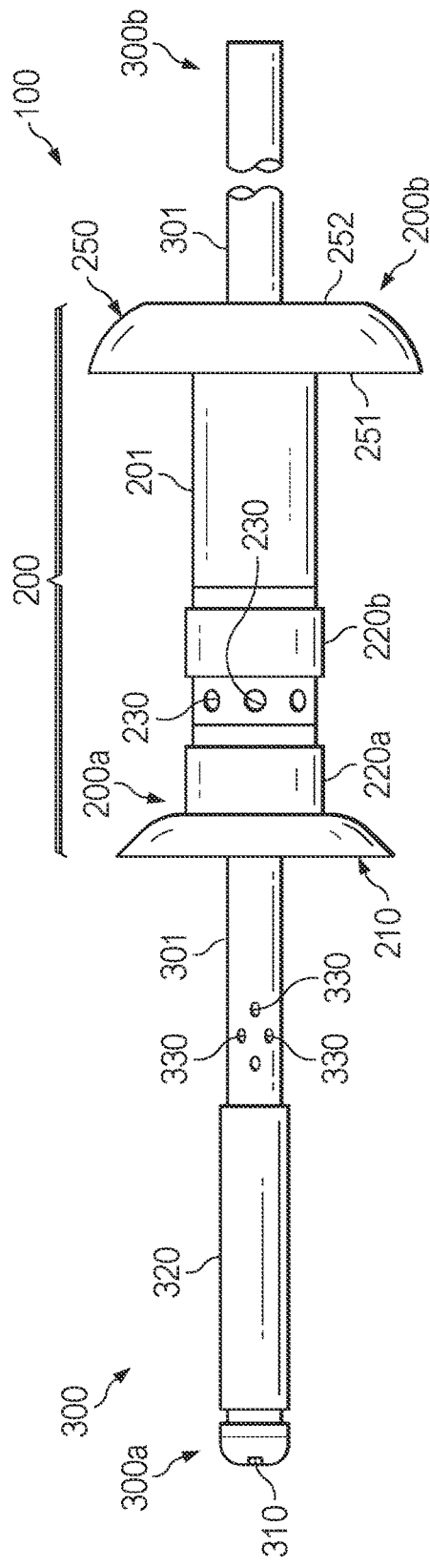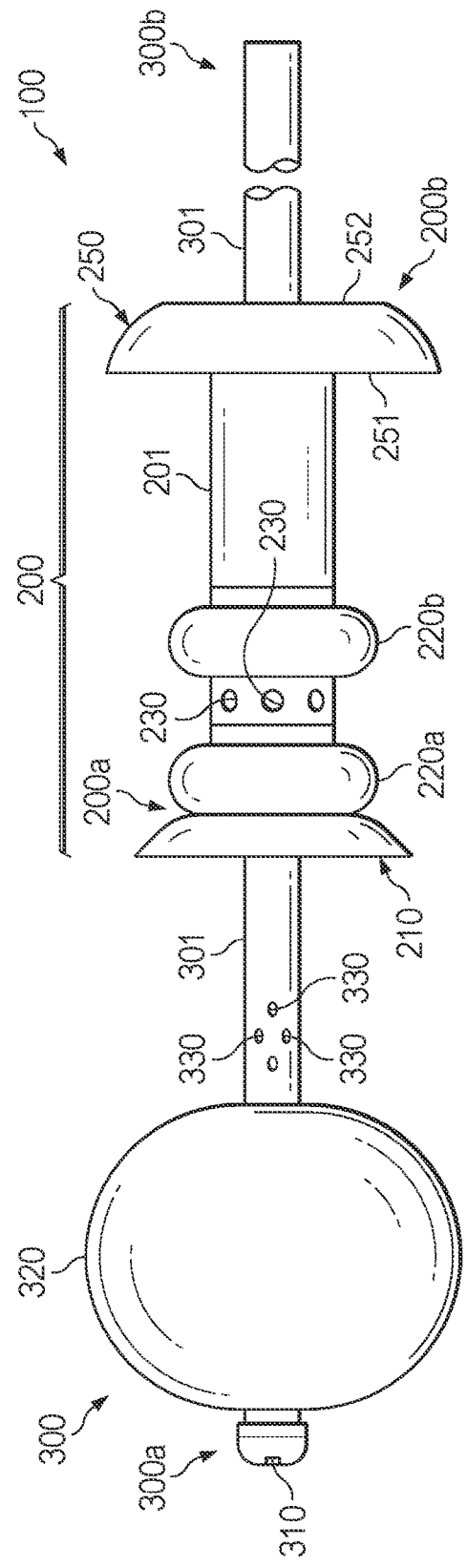

SURGICAL SYSTEMS AND DEVICES, INCLUDING METHODS FOR CONFIGURING SURGICAL SYSTEMS AND DEVICES, FOR MANAGING POSTPARTUM HEMORRHAGING

TECHNICAL FIELD

The present disclosure relates generally to systems, devices, and methods for managing postpartum hemorrhaging, and in particular, to surgical systems, subsystems, processors, devices, logic, methods, and processes for managing and controlling postpartum hemorrhaging.

BACKGROUND

Postpartum hemorrhaging (or "PPH") is the leading cause of maternal morbidity and mortality worldwide, responsible for more than 25% of deaths annually. PPH is generally understood and accepted as blood loss of greater than 500 ml for vaginal delivery and greater than 1,000 ml for caesarean delivery, although accurate estimation of blood loss at delivery and subsequent ascertainment of PPH can be challenging. Leading causes of PPH include uterine atony (failure of the uterus to contract), lacerations, retained placenta or clots, and clotting factor deficiency secondary to massive blood transfusion. In addition to death, other serious morbidity resulting from postpartum bleeding may include multi-organ failure, shock, adult respiratory distress syndrome, disseminated coagulopathy, and loss of fertility due to emergency hysterectomy (i.e., removal of the uterus).

Most cases of PPH have no identifiable risk factors. Despite advances in the field of obstetrics, PPH remains one of the main causes of maternal death in several countries. In fact, approximately 14 million women suffer from PPH, and of these, it is estimated that more than 125,000 women die of PPH in the world annually. Likewise, it is well known that 99% of these deaths occur in developing countries. Generally, PPH-related symptoms include, but are not limited to, dizziness, loss of consciousness, presence of hypotension, acceleration of heart rate, and an abnormal reduction in urine. These symptoms may last up to twenty-four hours (or more or less).

Uterine contraction is a natural physiological process that controls bleeding by constricting the vasculature of the uterus. If abnormal postpartum uterine bleeding occurs, initial conservative management, including uterine massage and administration of therapeutic oxytocin, is performed. If these interventions are found to be unsuccessful in regaining uterine tone and controlling uterine bleeding, additional conservative methods such as therapeutic doses of uterotonic medications are implemented. If these medications do not adequately control abnormal postpartum uterine bleeding or cannot be used in a patient due to contraindications, additional interventions are required.

However, the above methods usually take long time to completely control the PPH. Whereas immediately after diagnosis of primary PPH, it is imperative to implement appropriate and timely therapeutic measures as most deaths occur within the first few hours after onset of major bleeding. As such, an immediate arrest of bleeding is essential to save life.

BRIEF SUMMARY

Present example embodiments relate generally to and/or include systems, subsystems, assemblies, processors, and devices for addressing conventional problems, including those described above and in the present disclosure, and more specifically, example embodiments relate to systems, subsystems, assemblies, processors, and devices for managing post-partum hemorrhaging.

In an exemplary embodiment, a hysteroscopic system for managing post-partum hemorrhaging is described. The hysteroscopic system includes a main assembly. The main assembly is formed as an elongated body having an in vivo end and an in vitro end. When in operation, the in vivo end of the main assembly is configured to be inserted into and housed in a vaginal cavity of a patient; and the in vitro end of the main assembly is configured to remain outside of the vaginal cavity of the patient. The main assembly includes a main channel formed through the elongated body of the main assembly between the in vivo and in vitro ends of the main assembly. The main channel is formed along a first central axis (and/or is formed in such a way as to include the first central axis formed through it). The main assembly also includes a cervical seal member. The cervical seal member is formed at the in vivo end of the main assembly. The cervical seal member includes a central axis coaxial to the first central axis. The cervical seal member includes a contact wall and a non-contact wall opposite to the contact wall of the cervical seal member. The contact wall of the cervical seal member is configured in such a way as to face and contact with at least a portion of a cervix of the patient. The cervical seal member is configured to hermetically isolate a uterine cavity of the patient from the vaginal cavity of the patient when the contact wall of the cervical seal member is positioned to be in contact with at least a portion of the cervix of the patient. Alternatively or in addition, the cervical seal member is configured to ensure the main assembly does not enter into the uterine cavity of the patient. The main assembly also includes a first anchoring member. The first anchoring member is formed on (and/or attached to, formed with, etc.) the elongated body of the main assembly and adjacent to the cervical seal member. The first anchoring member is configured to transition between an anchoring state and a non-anchoring state. The anchoring state of the first anchoring member is a state in which the first anchoring member has a first overall volume (e.g., expanded outwardly away from the elongated body of the main assembly towards the wall of the vaginal cavity). The non-anchoring state of the first anchoring member is a state in which the first anchoring member has a second overall volume (e.g., not expanded outwardly away from the elongated body of the main assembly). The first overall volume is greater than the second overall volume. The main assembly also includes a second anchoring member. The second anchoring member is formed on (and/or attached to) the elongated body of the main assembly. The second anchoring member is configured to transition between an anchoring state and a non-anchoring state. The anchoring state of the second anchoring member is a state in which the second anchoring member has a third overall volume (e.g., expanded outwardly away from the elongated body of the main assembly towards the wall of the vaginal cavity). The non-anchoring state of the second anchoring member is a state in which the second anchoring member has a fourth overall volume (e.g., not expanded outwardly away from the elongated body of the main assembly). The third overall volume is greater than the fourth overall volume. The first overall volume may (or may not) be the same volume as the third overall volume. The second overall volume may (or may not) be the same volume as the fourth overall volume. The main assembly also includes a third anchoring member. The third anchoring member is formed between the first and second anchoring members. The third anchoring member is configured to transition between an anchoring state and a non-anchoring state. The anchoring state of the third anchoring member is a state in which the third anchoring member applies at least a first negative pressure (e.g., suction). The first negative pressure is an amount of negative pressure required to collapse at least a portion of the vaginal cavity (or vaginal wall forming the vaginal cavity) towards the elongated body of the main assembly. The non-anchoring state of the third anchoring member is a state in which the third anchoring member does not apply at least the first negative pressure (e.g., the non-anchoring state of the third anchoring member may be a state in which the third anchoring member does not apply any negative pressure).

The hysteroscopic system also includes a uterine assembly. The uterine assembly is formed as an elongated body having an in vivo end and an in vitro end. The uterine assembly is configured to be slidably housed in the main channel of the main assembly in such a way that the in vivo end of the uterine assembly is extendible outwardly away from the in vivo end of the main assembly (e.g., the uterine assembly can slide into and out of the main channel of the main assembly in both directions). The uterine assembly includes a first negative pressure port. The first negative pressure port is formed at or near a distal end of the in vivo end of the uterine assembly. The first negative pressure port is configured to transition between a haemostasis state and a non-haemostasis state. The haemostasis state of the first negative pressure port is a state in which the first negative pressure port applies a negative pressure having a magnitude that is greater than or equal to a second negative pressure. For example, such second negative pressure may be an amount of negative pressure required to collapse at least a portion of the uterine cavity (or uterine wall forming the uterine cavity) towards the elongated body of the uterine assembly. The non-haemostasis state of the first negative pressure port is a state in which the first negative pressure port does not apply a negative pressure having a magnitude that is greater than or equal to the second negative pressure (e.g., the non-haemostasis state of the first negative pressure port may be a state in which the first negative pressure port does not apply any negative pressure). The uterine assembly also includes a uterine expandable member. The uterine expandable member is formed on (and/or attached to, formed with, etc.) the elongated body of the uterine assembly and adjacent to the first negative pressure port. The uterine expandable member is configured to transition between a haemostasis state and a non-haemostasis state. The haemostasis state of the uterine expandable member is a state in which the uterine expandable member has a third overall volume (e.g., expanded outwardly away from the elongated body of the uterine assembly towards the wall of the uterine cavity). The non-haemostasis state of the uterine expandable member is a state in which the uterine expandable member has a fourth overall volume (e.g., not expanded outwardly away from the elongated body of the uterine assembly). The third overall volume is greater than the fourth overall volume. The uterine assembly also includes a second negative pressure port. The second negative pressure port is formed adjacent to the uterine expandable member in such a way that the uterine expandable member is positioned between the first and second negative pressure ports. The second negative pressure port is configured to transition between a haemostasis state and a non-haemostasis state. The haemostasis state of the second negative pressure port is a state in which the second negative pressure port applies a negative pressure having a magnitude that is greater than or equal to a third negative pressure. For example, such third negative pressure may be an amount of negative pressure required to collapse at least a portion of the uterine cavity (or uterine wall forming the uterine cavity) towards the elongated body of the uterine assembly. The non-anchoring state of the second negative pressure port is a state in which the second negative pressure port does not apply a negative pressure having a magnitude that is greater than or equal to the third negative pressure (e.g., the non-haemostasis state of the second negative pressure port may be a state in which the second negative pressure port does not apply any negative pressure). The uterine assembly is configured to apply the second and third negative pressures in such a way that a combination of the second and third negative pressures is a sufficient amount of negative pressure (and/or sufficiently directed in the right directions and/or placed in the right locations within the uterine cavity) so as to collapse at least a portion of the uterine cavity (or uterine wall forming the uterine cavity) towards the elongated body of the uterine assembly.

In another exemplary embodiment, a hysteroscopic system for managing post-partum hemorrhaging is described. The hysteroscopic system includes a main assembly. The main assembly is formed as an elongated body having an in vivo end and an in vitro end. The in vivo end of the main assembly is configured to be inserted into and housed in a vaginal cavity of a patient. The in vitro end of the main assembly is configured to remain outside of the vaginal cavity of the patient. The main assembly includes a main channel. The main channel is formed through the elongated body of the main assembly between the in vivo and in vitro ends of the main assembly. The main channel is formed along a first central axis (and/or is formed in such a way as to include the first central axis formed through it). The main assembly also includes a first anchoring member. The first anchoring member is formed on (and/or attached to, formed with, etc.) the elongated body of the main assembly. The first anchoring member is configured to transition between an anchoring state and a non-anchoring state. The anchoring state of the first anchoring member is a state in which the first anchoring member is expanded away from the elongated body of the main assembly (e.g., the anchoring state of the first anchoring member may be a state in which the first anchoring member is protruded towards the vaginal walls forming the vaginal cavity of the patient and/or a state in which the first anchoring member has an increased volume as compared to the non-anchoring state). The main assembly also includes a second anchoring member. The second anchoring member is formed on (and/or attached to) the elongated body of the main assembly. The second anchoring member is configured to transition between an anchoring state and a non-anchoring state. The anchoring state of the second anchoring member is a state in which the second anchoring member is expanded away from the elongated body of the main assembly (e.g., the anchoring state of the second anchoring member may be a state in which the second anchoring member is protruded towards the vaginal walls forming the vaginal cavity of the patient and/or a state in which the second anchoring member has an increased volume as compared to the non-anchoring state). The main assembly also includes a vaginal seal member. The vaginal seal member is formed at the in vitro end of the main assembly. The vaginal seal member may include a central axis coaxial to the first central axis. The vaginal seal member includes a contact wall and a non-contact wall opposite to the contact wall. The contact wall of the vaginal seal member is configured in such a way as to face and contact with at least a portion of a vulva of the patient. The vaginal seal member is configured to hermetically isolate the vaginal cavity of the patient when the contact wall of the vaginal seal member is positioned to be in contact with at least a portion of the vulva of the patient. Alternatively or in addition, the vaginal seal member is configured to ensure the main assembly is properly positioned in the vaginal cavity of the patient. The main assembly also includes a third anchoring member. The third anchoring member is formed between the first and second anchoring members. The third anchoring member is configured to transition between an anchoring state and a non-anchoring state. The anchoring state of the third anchoring member is a state in which the third anchoring member applies at least a first negative pressure (e.g., suction).

The hysteroscopic system also includes a uterine assembly. The uterine assembly is formed as an elongated body having an in vivo end and an in vitro end. The uterine assembly is configured to be slidably housed in the main channel of the main assembly (e.g., the uterine assembly can slide into and out of the main channel of the main assembly in both directions). The uterine assembly includes a first negative pressure port. The first negative pressure port is formed at a distal end of the in vivo end of the uterine assembly. The first negative pressure port is configured to transition between a haemostasis state and a non-haemostasis state. The haemostasis state of the first negative pressure port is a state in which the first negative pressure port applies at least a second negative pressure. For example, such second negative pressure may be an amount of negative pressure required to collapse at least a portion of the uterine cavity (or uterine wall forming the uterine cavity) towards the elongated body of the uterine assembly. The uterine assembly also includes a uterine expandable member. The uterine expandable member is formed on (and/or attached to, formed with, etc.) the elongated body of the uterine assembly and adjacent to the first negative pressure port. The uterine expandable member is configured to transition between a haemostasis state and a non-haemostasis state. The haemostasis state of the uterine expandable member is a state in which the uterine expandable member is expanded away from the elongated body of the uterine assembly (e.g., the haemostasis state of the uterine expandable member may be a state in which the uterine expandable member is protruded towards the uterine wall forming the uterine cavity of the patient and/or a state in which the uterine expandable member has an increased volume as compared to the haemostasis state). The uterine assembly also includes a second negative pressure port. The second negative pressure port is formed adjacent to the uterine expandable member in such a way that the uterine expandable member is positioned between the first and second negative pressure ports. The second negative pressure port is configured to transition between a haemostasis state and a non-haemostasis state. The haemostasis state of the second negative pressure port is a state in which the second negative pressure port applies at least a third negative pressure. For example, such third negative pressure may be an amount of negative pressure required to collapse at least a portion of the uterine cavity (or uterine wall forming the uterine cavity) towards the elongated body of the uterine assembly.

In another exemplary embodiment a hysteroscopic system for managing post-partum hemorrhaging is described. The hysteroscopic system includes a main assembly. The main assembly is formed as an elongated body having an in vivo end and an in vitro end. When in operation, the in vivo end of the main assembly is configured to be inserted into and housed in a vaginal cavity of a patient; and the in vitro end of the main assembly is configured to remain outside of the vaginal cavity of the patient. The main assembly includes a main channel. The main channel is formed through the elongated body of the main assembly between the in vivo and in vitro ends of the main assembly. The main channel is formed along a first central axis (and/or is formed in such a way as to include the first central axis formed through it). The main assembly also includes a cervical seal member. The cervical seal member is formed at the in vivo end of the main assembly. The cervical seal member includes a central axis coaxial to the first central axis. The cervical seal member includes a contact wall and a non-contact wall opposite to the contact wall of the cervical seal member. The contact wall of the cervical seal member is configured in such a way as to face and contact with at least a portion of a cervix of the patient. The cervical seal member is configured to hermetically isolate a uterine cavity of the patient from the vaginal cavity of the patient when the contact wall of the cervical seal member is positioned to be in contact with at least a portion of the cervix of the patient. Alternatively or in addition, the cervical seal member is configured to ensure the main assembly does not enter into the uterine cavity of the patient. The main assembly also includes a first anchoring member. The first anchoring member is formed on (and/or attached to, formed with, etc.) the elongated body of the main assembly and adjacent to the cervical seal member. The first anchoring member is configured to transition between an anchoring state and a non-anchoring state. The anchoring state of the first anchoring member is a state in which the first anchoring member has a first overall volume (e.g., expanded outwardly away from the elongated body of the main assembly towards the wall of the vaginal cavity). The non-anchoring state of the first anchoring member is a state in which the first anchoring member has a second overall volume (e.g., not expanded outwardly away from the elongated body of the main assembly). The first overall volume is greater than the second overall volume. The main assembly also includes a second anchoring member. The second anchoring member is formed on (and/or attached to) the elongated body of the main assembly. The second anchoring member is configured to transition between an anchoring state and a non-anchoring state. The anchoring state of the second anchoring member is a state in which the second anchoring member has a third overall volume (e.g., expanded outwardly away from the elongated body of the main assembly towards the wall of the vaginal cavity). The non-anchoring state of the second anchoring member is a state in which the second anchoring member has a fourth overall volume (e.g., not expanded outwardly away from the elongated body of the main assembly). The third overall volume is greater than the fourth overall volume. The first overall volume may (or may not) be the same volume as the third overall volume. The second overall volume may (or may not) be the same volume as the fourth overall volume. The main assembly also includes a third anchoring member. The third anchoring member is formed between the first and second anchoring members. The third anchoring member is configured to transition between an anchoring state and a non-anchoring state. The anchoring state of the third anchoring member is a state in which the third anchoring member applies at least a first negative pressure (e.g., suction). The first negative pressure is an amount of negative pressure required to collapse at least a portion of the vaginal cavity (or vaginal wall forming the vaginal cavity of the patient) towards the elongated body of the main assembly. The non-anchoring state of the third anchoring member is a state in which the third anchoring member does not apply at least the first negative pressure (e.g., the non-anchoring state of the third anchoring member may be a state in which the third anchoring member does not apply any negative pressure). The main assembly also includes a vaginal seal member. The vaginal seal member is formed at the in vitro end of the main assembly. The vaginal seal member includes a central axis coaxial to the first central axis. The vaginal seal member includes a contact wall and a non-contact wall opposite to the contact wall. The contact wall of the vaginal seal member is configured in such a way as to face and contact with at least a portion of a vulva of the patient. The vaginal seal member is configured to hermetically isolate the vaginal cavity of the patient when the contact wall of the vaginal seal member is positioned to be in contact with at least a portion of the vulva of the patient. Alternatively or in addition, the vaginal seal member is configured to ensure the main assembly is properly positioned in the vaginal cavity of the patient.

The hysteroscopic system also includes a uterine assembly. The uterine assembly is formed as an elongated body having an in vivo end and an in vitro end. The uterine assembly is configured to be slidably housed in the main channel of the main assembly in such a way that the in vivo end of the uterine assembly is extendible outwardly away from the in vivo end of the main assembly (e.g., the uterine assembly can slide into and out of the main channel of the main assembly in both directions). The uterine assembly includes a first negative pressure port. The first negative pressure port is formed at a distal end of the in vivo end of the uterine assembly. The first negative pressure port is configured to transition between a haemostasis state and a non-haemostasis state. The haemostasis state of the first negative pressure port is a state in which the first negative pressure port applies a negative pressure having a magnitude that is greater than or equal to a second negative pressure. For example, such second negative pressure may be an amount of negative pressure required to collapse at least a portion of the uterine cavity (or uterine wall forming the uterine cavity) towards the elongated body of the uterine assembly. The non-haemostasis state of the first negative pressure port is a state in which the first negative pressure port does not apply a negative pressure having a magnitude that is greater than or equal to the second negative pressure (e.g., the non-haemostasis state of the second negative pressure port may be a state in which the second negative pressure port does not apply any negative pressure). The uterine assembly also includes a uterine expandable member. The uterine expandable member is formed on (and/or attached to, formed with, etc.) the elongated body of the uterine assembly and adjacent to the first negative pressure port. The uterine expandable member is configured to transition between a haemostasis state and a non-haemostasis state. The haemostasis state of the uterine expandable member is a state in which the uterine expandable member has a third overall volume (e.g., expanded outwardly away from the elongated body of the uterine assembly towards the wall of the uterine cavity). The non-haemostasis state of the uterine expandable member is a state in which the uterine expandable member has a fourth overall volume (e.g., not expanded outwardly away from the elongated body of the uterine assembly). The third overall volume greater than the fourth overall volume. The uterine assembly also includes a second negative pressure port. The second negative pressure port is formed adjacent to the uterine expandable member in such a way that the uterine expandable member is positioned between the first and second negative pressure ports. The second negative pressure port is configured to transition between a haemostasis state and a non-haemostasis state. The haemostasis state of the second negative pressure port is a state in which the second negative pressure port applies a negative pressure having a magnitude that is greater than or equal to a third negative pressure. For example, such third negative pressure may be an amount of negative pressure required to collapse at least a portion of the uterine cavity (or uterine wall forming the uterine cavity) towards the elongated body of the uterine assembly. The non-haemostasis state of the second negative pressure port is a state in which the second negative pressure port does not apply a negative pressure having a magnitude that is greater than or equal to the third negative pressure (e.g., the non-haemostasis state of the second negative pressure port may be a state in which the second negative pressure port does not apply any negative pressure).

In another exemplary embodiment a hysteroscopic system for managing post-partum hemorrhaging is described. The hysteroscopic system includes a main assembly. The main assembly is formed as an elongated body having an in vivo end and an in vitro end. The in vivo end of the main assembly is configured to be inserted into and housed in a vaginal cavity of a patient. The in vitro end of the main assembly is configured to remain outside of the vaginal cavity of the patient. The main assembly includes a main channel. The main channel is formed through the elongated body of the main assembly between the in vivo and in vitro ends of the main assembly. The main channel is formed along a first central axis (and/or is formed in such a way as to include the first central axis formed through it). The main assembly also includes a first anchoring member. The first anchoring member is formed on the elongated body of the main assembly. The first anchoring member is configured to transition between an anchoring state and a non-anchoring state. The anchoring state of the first anchoring member is a state in which the first anchoring member is expanded away from the elongated body of the main assembly. The main assembly also includes a second anchoring member. The second anchoring member is configured to transition between an anchoring state and a non-anchoring state. The anchoring state of the second anchoring member is a state in which the second anchoring member is expanded away from the elongated body of the main assembly. The main assembly also includes a third anchoring member. The third anchoring member is formed between the first and second anchoring members. The third anchoring member is configured to transition between an anchoring state and a non-anchoring state. The anchoring state of the third anchoring member is a state in which the third anchoring member applies at least a first negative pressure (e.g., suction).

The hysteroscopic system also includes a uterine assembly. The uterine assembly is formed as an elongated body having an in vivo end and an in vitro end. The uterine assembly is configured to be slidably housed in the main channel of the main assembly (e.g., the uterine assembly can slide into and out of the main channel of the main assembly in both directions). The uterine assembly includes a first negative pressure port. The first negative pressure port is formed at or near a distal end of the in vivo end of the uterine assembly. The first negative pressure port is configured to transition between a haemostasis state and a non-haemostasis state. The haemostasis state of the first negative pressure port is a state in which the first negative pressure port applies at least a second negative pressure. The uterine assembly also includes a uterine expandable member. The uterine expandable member is formed on the elongated body of the uterine assembly and adjacent to the first negative pressure port. The uterine expandable member is configured to transition between a haemostasis state and a non-haemostasis state. The haemostasis state of the uterine expandable member is a state in which the uterine expandable member is expanded away from the elongated body of the uterine assembly. The uterine assembly also includes a second negative pressure port. The second negative pressure port is formed adjacent to the uterine expandable member in such a way that the uterine expandable member is positioned between the first and second negative pressure ports. The second negative pressure port is configured to transition between a haemostasis state and a non-haemostasis state. The haemostasis state of the second negative pressure port is a state in which the second negative pressure port applies at least a third negative pressure.

The hysteroscopic system also includes a controller. The controller is configured to perform at least a transitioning of the first anchoring member between the anchoring state and the non-anchoring state. The controller is also configured to perform at least a transitioning of the second anchoring member between the anchoring state and the non-anchoring state. The controller is also configured to perform at least a transitioning of the third anchoring member between the anchoring state and the non-anchoring state. The controller is also configured to perform at least a transitioning of the first negative pressure port between the haemostasis state and the non-haemostasis state. The controller is also configured to perform at least a transitioning of the uterine expandable member between the haemostasis state and the non-haemostasis state. The controller is also configured to perform at least a transitioning of the second negative pressure port between the haemostasis state and the non-haemostasis state. The controller is also configured to apply the second and third negative pressures in such a way that a combination of the second and third negative pressures is a sufficient amount of negative pressure (and/or sufficiently directed in the right directions and/or placed in the right locations within the uterine cavity) so as to collapse at least a portion of the uterine cavity (or uterine wall forming the uterine cavity) towards the elongated body of the uterine assembly.

In another exemplary embodiment a method of configuring a hysteroscopic system to manage post-partum hemorrhaging is described. The method includes providing a hysteroscopic system. The hysteroscopic system includes a main assembly. The main assembly is formed as an elongated body having an in vivo end and an in vitro end. The main assembly includes a main channel. The main channel is formed through the elongated body of the main assembly between the in vivo and in vitro ends of the main assembly. The main channel is formed along a first central axis (and/or is formed in such a way as to include the first central axis formed through it). The main assembly also includes a cervical seal member. The cervical seal member is formed at the in vivo end of the main assembly. The cervical seal member includes a central axis coaxial to the first central axis. The cervical seal member includes a contact wall and a non-contact wall opposite to the contact wall of the cervical seal member. The contact wall of the cervical seal member is configured in such a way as to face and contact with at least a portion of a cervix of the patient. The cervical seal member is configured to hermetically isolate a uterine cavity of the patient from the vaginal cavity of the patient when the contact wall of the cervical seal member is positioned to be in contact with at least a portion of the cervix of the patient. Alternatively or in addition, the cervical seal member is configured to ensure the main assembly does not enter into the uterine cavity of the patient. The main assembly also includes a first anchoring member. The first anchoring member is formed on (and/or attached to, formed with, etc.) the elongated body of the main assembly and adjacent to the cervical seal member. The first anchoring member is configured to transition between an anchoring state and a non-anchoring state. The anchoring state of the first anchoring member is a state in which the first anchoring member has a first overall volume (e.g., expanded outwardly away from the elongated body of the main assembly towards the wall of the vaginal cavity). The non-anchoring state of the first anchoring member is a state in which the first anchoring member has a second overall volume (e.g., not expanded outwardly away from the elongated body of the main assembly). The first overall volume is greater than the second overall volume. The main assembly also includes a second anchoring member. The second anchoring member is formed on (and/or attached to) the elongated body of the main assembly. The second anchoring member is configured to transition between an anchoring state and a non-anchoring state. The anchoring state of the second anchoring member is a state in which the second anchoring member has a third overall volume (e.g., expanded outwardly away from the elongated body of the main assembly towards the wall of the vaginal cavity). The non-anchoring state of the second anchoring member is a state in which the second anchoring member has a fourth overall volume (e.g., not expanded outwardly away from the elongated body of the main assembly). The third overall volume is greater than the fourth overall volume. The first overall volume may (or may not) be the same volume as the third overall volume. The second overall volume may (or may not) be the same volume as the fourth overall volume. The main assembly also includes a third anchoring member. The third anchoring member is formed between the first and second anchoring members. The third anchoring member is configured to transition between an anchoring state and a non-anchoring state. The anchoring state of the third anchoring member is a state in which the third anchoring member applies at least a first negative pressure (e.g., suction). The first negative pressure is an amount of negative pressure required to collapse at least a portion of the vaginal cavity (or vaginal wall forming the vaginal cavity) towards the elongated body of the main assembly. The non-anchoring state of the third anchoring member is a state in which the third anchoring member does not apply at least the first negative pressure (e.g., the non-anchoring state of the third anchoring member may be a state in which the third anchoring member does not apply any negative pressure). The hysteroscopic system also includes a uterine assembly. The uterine assembly is formed as an elongated body having an in vivo end and an in vitro end. The uterine assembly is configured to be slidably housed in the main channel of the main assembly in such a way that the in vivo end of the uterine assembly is extendible outwardly away from the in vivo end of the main assembly (e.g., the uterine assembly can slide into and out of the main channel of the main assembly in both directions). The uterine assembly includes a first negative pressure port. The first negative pressure port is formed at or near a distal end of the in vivo end of the uterine assembly. The first negative pressure port is configured to transition between a haemostasis state and a non-haemostasis state. The haemostasis state of the first negative pressure port is a state in which the first negative pressure port applies a negative pressure having a magnitude that is greater than or equal to a second negative pressure. For example, such second negative pressure may be an amount of negative pressure required to collapse at least a portion of the uterine cavity (or uterine wall forming the uterine cavity) towards the elongated body of the uterine assembly. The non-haemostasis state of the first negative pressure port is a state in which the first negative pressure port does not apply a negative pressure having a magnitude that is greater than or equal to the second negative pressure (e.g., the non-haemostasis state of the first negative pressure port may be a state in which the first negative pressure port does not apply any negative pressure). The uterine assembly also includes a uterine expandable member. The uterine expandable member is formed on (and/or attached to, formed with, etc.) the elongated body of the uterine assembly and adjacent to the first negative pressure port. The uterine expandable member is configured to transition between a haemostasis state and a non-haemostasis state. The haemostasis state of the uterine expandable member is a state in which the uterine expandable member has a third overall volume (e.g., expanded outwardly away from the elongated body of the uterine assembly towards the wall of the uterine cavity). The non-haemostasis state of the uterine expandable member is a state in which the uterine expandable member has a fourth overall volume (e.g., not expanded outwardly away from the elongated body of the uterine assembly). The third overall volume is greater than the fourth overall volume. The uterine assembly also includes a second negative pressure port. The second negative pressure port is formed adjacent to the uterine expandable member in such a way that the uterine expandable member is positioned between the first and second negative pressure ports. The second negative pressure port is configured to transition between a haemostasis state and a non-haemostasis state. The haemostasis state of the second negative pressure port is a state in which the second negative pressure port applies a negative pressure having a magnitude that is greater than or equal to a third negative pressure. For example, such third negative pressure may be an amount of negative pressure required to collapse at least a portion of the uterine cavity (or uterine wall forming the uterine cavity) towards the elongated body of the uterine assembly. The non-anchoring state of the second negative pressure port is a state in which the second negative pressure port does not apply a negative pressure having a magnitude that is greater than or equal to the third negative pressure (e.g., the non-haemostasis state of the second negative pressure port may be a state in which the second negative pressure port does not apply any negative pressure). The uterine assembly is configured to apply the second and third negative pressures in such a way that a combination of the second and third negative pressures is a sufficient amount of negative pressure (and/or sufficiently directed in the right directions and/or placed in the right locations within the uterine cavity) so as to collapse at least a portion of the uterine cavity (or uterine wall forming the uterine cavity) towards the elongated body of the uterine assembly.

The method also includes configuring the uterine assembly and the main assembly in such a way that at least a portion of the uterine assembly is housed in the main channel of the main assembly. The method also includes introducing the hysteroscopic system trans-vaginally until the cervical seal member is brought into contact with at least a portion of a cervix. The contact of the cervical seal member and at least a portion of a cervix limits the air to pass in or out. The method also includes transitioning the main assembly to be in the anchoring state. The transitioning of the main assembly to be in the anchoring state causes at least a portion of the vaginal cavity to collapse towards the elongated body of the main assembly. The transitioning of the main assembly to be in the anchoring state includes transitioning the first anchoring member to be in the anchoring state. The transitioning of the main assembly to be in the anchoring state also includes transitioning the second anchoring member to be in the anchoring state. The transitioning of the main assembly to be in the anchoring state also includes transitioning the third anchoring member to be in the anchoring state. The method also includes transitioning the uterine assembly to be in the haemostasis state. The transitioning of the uterine assembly causes at least a portion of the uterine cavity to collapse towards the elongated body. The transitioning of the uterine assembly to be in the haemostasis state includes transitioning the uterine expandable member to be in the haemostasis state. The transitioning of the uterine assembly to be in the haemostasis state also includes transitioning the first negative pressure port to be in the haemostasis state. The transitioning of the uterine assembly to be in the haemostasis state also includes transitioning the second negative pressure port to be in the haemostasis state. The method also includes transitioning the uterine assembly from the haemostasis state to the non-haemostasis state. The method also includes removing the uterine assembly from the main channel of the main assembly. The transitioning of the uterine assembly from the haemostasis state to the non-haemostasis state includes transitioning the uterine expandable member to be in the non-haemostasis state. The transitioning of the uterine assembly from the haemostasis state to the non-haemostasis state also includes transitioning the first negative pressure port to be in the non-haemostasis state. The transitioning of the uterine assembly from the haemostasis state to the non-haemostasis state also includes transitioning the second negative pressure port to be in the non-haemostasis state.

BRIEF DESCRIPTION OF THE FIGURES

For a more complete understanding of the present disclosure, example embodiments, and their advantages, reference is now made to the following description taken in conjunction with the accompanying figures, in which like reference numbers indicate like features, and:

FIG. 2C is another illustration of a side view of an example embodiment of a hysteroscopic system (with main assembly in non-anchoring state and uterine assembly in non-haemostasis state) for managing post-partum hemorrhaging;

FIG. 2D is another illustration of a side view of an example embodiment of a hysteroscopic system (with main assembly in anchoring state and uterine assembly in haemostasis state) for managing post-partum hemorrhaging;

Although similar reference numbers may be used to refer to similar elements in the figures for convenience, it can be appreciated that each of the various example embodiments may be considered to be distinct variations.

Figure 1A:
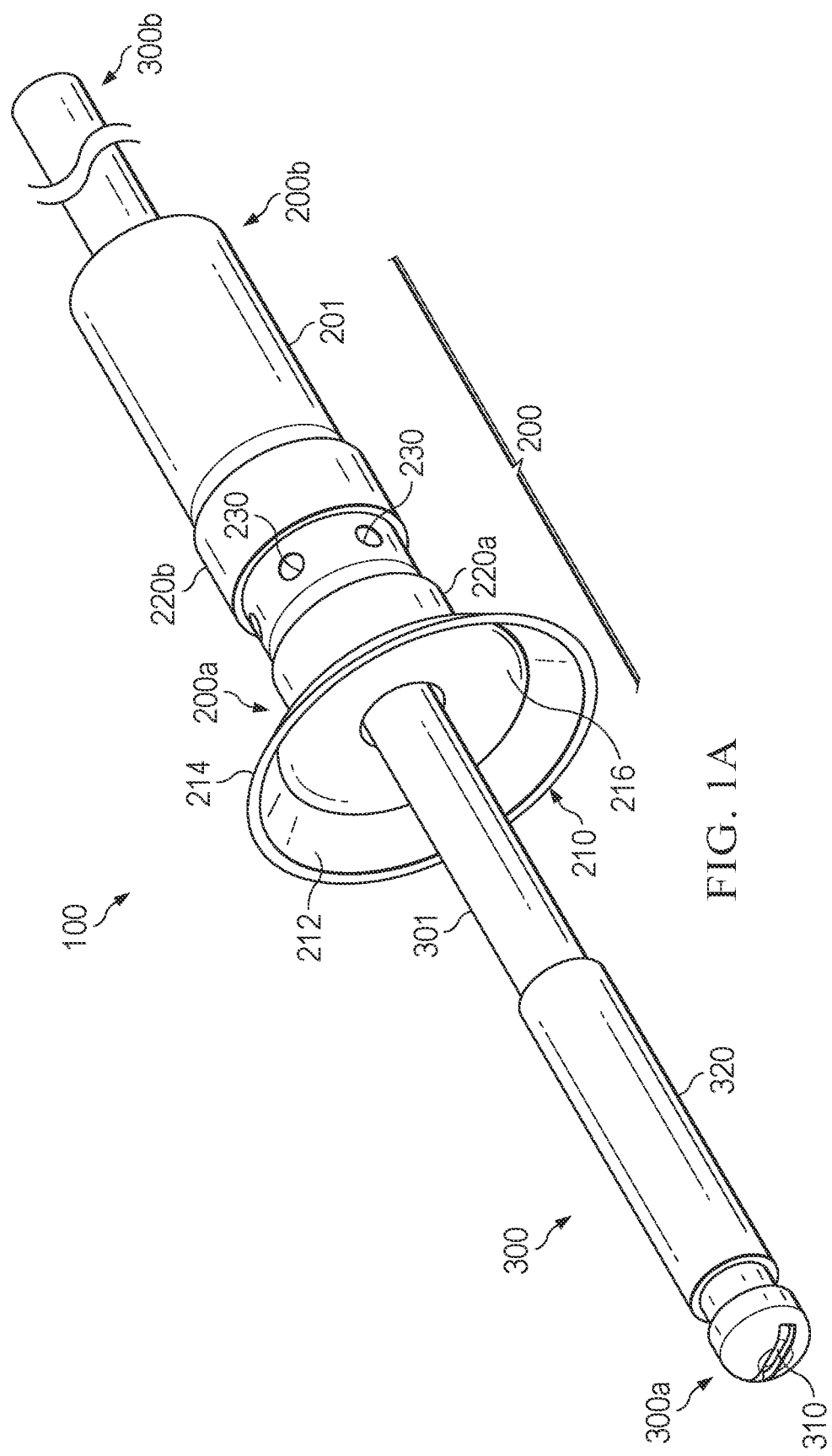
FIG. 1A is an illustration of a perspective view of an example embodiment of a hysteroscopic system (with main assembly in non-anchoring state and uterine assembly in non-haemostasis state) for managing post-partum hemorrhaging.
Figure 1B:
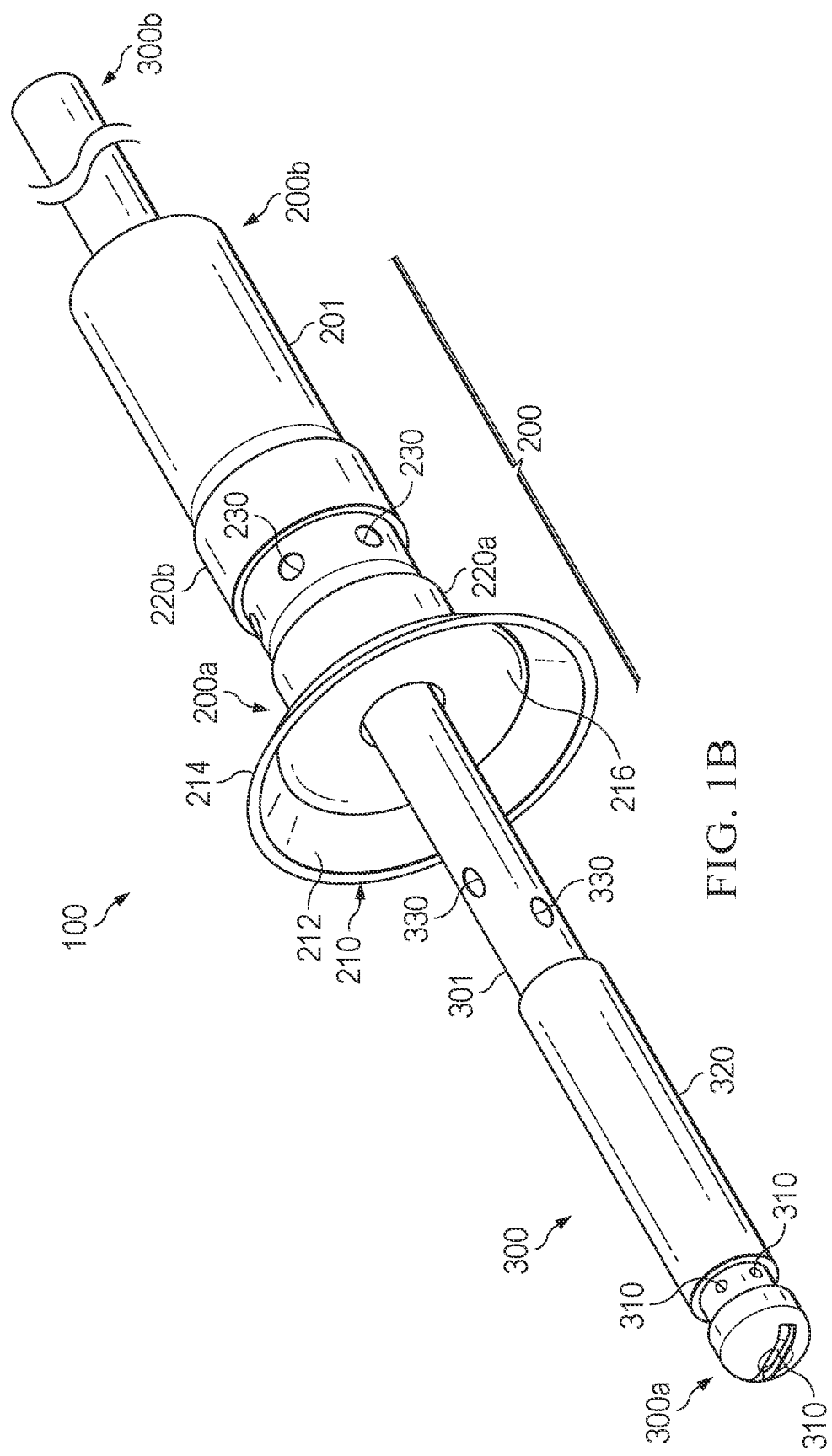
FIG. 1B is another illustration of a perspective view of an embodiment of a hysteroscopic system (with main assembly in non-anchoring state and uterine assembly in non-haemostasis state) for managing post-partum hemorrhaging.

Example embodiments will now be described with reference to the accompanying figures, which form a part of the present disclosure and which illustrate example embodiments which may be practiced. As used in the present disclosure and the appended claims, the terms "embodiment", "example embodiment", "exemplary embodiment", and "present embodiment" do not necessarily refer to a single embodiment, although they may, and various example embodiments may be readily combined and/or interchanged without departing from the scope or spirit of example embodiments. Furthermore, the terminology as used in the present disclosure and the appended claims is for the purpose of describing example embodiments only and is not intended to be limitations. In this respect, as used in the present disclosure and the appended claims, the term "in" may include "in" and "on", and the terms "a", "an", and "the" may include singular and plural references. Furthermore, as used in the present disclosure and the appended claims, the term "by" may also mean "from," depending on the context. Furthermore, as used in the present disclosure and the appended claims, the term "if" may also mean "when" or "upon", depending on the context. Furthermore, as used in the present disclosure and the appended claims, the words "and/or" may refer to and encompass any and all possible combinations of one or more of the associated listed items.

DETAILED DESCRIPTION

Present example embodiments relate generally to and/or include systems, subsystems, assemblies, processors, and devices for addressing conventional problems, including those described above and in the present disclosure, and more specifically, example embodiments relate to systems, subsystems, assemblies, processors, controllers, and devices for managing postpartum hemorrhaging.

It is to be understood in the present disclosure that example embodiments may also be used to manage, control, reduce, treat, stop, or the like (referred to herein as "manage") other clinical conditions including, but not limited to, obstetric hemorrhaging, post-abortion hemorrhaging, vaginal bleeding, uterine atony, cervical laceration, uterine perforation, cervical pregnancy, etc.

Example embodiments will now be described below with reference to the accompanying figures, which form a part of the present disclosure.

Example Embodiments of a Hysteroscopic System for Managing Postpartum Hemorrhaging (e.g., Hysteroscopic System 100).

FIG. 1A, FIG. 1B, FIG. 1C, FIG. 1D, FIG. 1E, FIG. 1F, FIG. 1G, FIG. 1H, FIG. 2A, FIG. 2B, FIG. 2C, and FIG. 2D illustrate example embodiments of a hysteroscopic system (e.g. hysteroscopic system 100). The hysteroscopic system 100 may be configurable or configured to manage postpartum hemorrhaging (or "PPH"). Alternatively or in addition, the hysteroscopic system 100 may be configurable or configured to manage other clinical conditions including, but not limited to, obstetric hemorrhaging, post-abortion hemorrhaging, vaginal bleeding, uterine atony, cervical laceration, uterine perforation, cervical pregnancy. Alternatively or in addition, the hysteroscopic system 100 may be configurable or configured to manage other clinical conditions using suction and/or anchorage mechanism.

To perform the actions, functions, processes, and/or methods described above and in the present disclosure, example embodiments of the hysteroscopic system 100 include one or more elements.

For example, the hysteroscopic system 100 includes a main assembly (e.g., main assembly 200). The main assembly 200 may be formed as and/or including an elongated body 201 having an in vivo end 200a and an in vitro end 200b. The main assembly 200 may include a main channel 202 formed through the elongated body 201 of the main assembly 200. The main assembly 200 may also include one or more cervical seal members 210 formed at the in vivo end 200a of the main assembly 200. The cervical seal member 210 may be configurable or configured to, among other things, ensure that the main assembly 200 is properly positioned in a vaginal cavity of the patient (e.g., by ensuring that the cervical seal member 210 abuts, is adjacent to, seals, encloses, and/or is in contact with at least a portion of a cervix (and/or surround areas of the cervix) of the patient) and/or ensure that the uterine cavity and the vaginal cavity of the patient are isolated from one another (e.g., by providing a separation, seal, and/or hermetic seal for the uterine cavity). The main assembly 200 may also include one or more first anchoring members 220a. The main assembly 200 may also include one or more second anchoring members 220b. The main assembly 200 may also include one or more third anchoring members 230. The main assembly 200 may also include one or more locking members or mechanisms 240. The locking member 240 may be configurable or configured to join, lock, restrict, or the like, movement of the main assembly 200 relative to another element of the hysteroscopic system 100 (e.g., relative to the uterine assembly 300 when the uterine assembly 300 is inserted through the main channel 202; relative to the manipulator assembly 400 when the manipulator assembly 400 is inserted through the main channel 202; etc.). The main assembly 200 may also include one or more vaginal seal members 250. The vaginal seal member 250 may be configurable or configured to, among other things, ensure that the main assembly 200 is properly positioned in a vaginal cavity of the patient (e.g., by ensuring that the vaginal seal member 250 abuts, is adjacent to, seals, encloses, and/or is in contact with at least a portion of a vulva (and/or surrounding areas of the vulva) of the patient) and/or ensure that the vaginal cavity of the patient is separated and/or hermetically sealed (e.g., separated from outside of the patient).

As will be further described in the present disclosure, when in operation, the in vivo end 200a of the main assembly 200 is configurable or configured to be inserted into (e.g., through a patient's vagina) and housed in a vaginal cavity of the patient. The in vitro end 200*b* of the main assembly 200 is configurable or configured to remain outside of the vaginal cavity of the patient. As will be further described in the present disclosure, the main assembly 200 is configurable or configured to be anchored and/or secured in the vaginal cavity of the patient (and/or anchored and/or secured relative to the vaginal cavity of the patient and/or vaginal walls forming the vaginal cavity of the patient; also referred to herein as an "anchoring state" or "anchored state") through one or more other elements of the hysteroscopic system 100 (e.g., via transitioning of the first anchoring member 220*a* to an anchoring state; transitioning of the second anchoring member 220*b* to an anchoring state; and/or transitioning of the third anchoring member 230 to an anchoring state). The main assembly 200 is also configurable or configured to be non-anchored and/or non-secured (or not anchored or not secured) in the vaginal cavity of the patient (and/or non-anchored and/or non-secured relative to the vaginal cavity of the patient and/or vaginal walls forming the vaginal cavity of the patient; also referred to herein as an "non-anchoring state" or "non-anchored state") through one or more other elements of the hysteroscopic system 100 (e.g., via transitioning of the first anchoring member 220*a* to a non-anchoring state; transitioning of the second anchoring member 220*b* to a non-anchoring state; and/or transitioning of the third anchoring member 230 to a non-anchoring state).

As used in the present disclosure, a reference to "anchor", "anchoring", "anchored", "anchorable", "secure", "securing", "secured", "securable", or the like, of one or more elements of the hysteroscopic system 100 (e.g., the main assembly 200, first anchoring member 220*a*, second anchoring member 220*b*, third anchoring member 230, uterine assembly 300, first negative pressure port 310, uterine expandable member 320, and/or second negative pressure port 330) to one or more cavities and/or walls forming a cavity of a patient (e.g., vaginal cavity, vaginal wall forming a vaginal cavity of the patient, uterine cavity, and/or uterine wall forming a uterine cavity of the patient) includes setting, changing, or transitioning a state of one or more elements of the hysteroscopic system 100 (e.g., transitioning from a non-anchoring state to an anchoring state; transitioning from a non-hemostasis state to a hemostasis state; transitioning from a non-securing state to a securing state; etc.); actuating, adjusting, expanding, and/or protruding one or more elements of the hysteroscopic system 100 (e.g., for expandable members, such as the first anchoring member 220*a*, second anchoring member 220*b*, uterine expandable member 320, etc.); setting, applying, or increasing negative pressure or suction from one or more elements of the hysteroscopic system 100 (e.g., for negative pressure ports, such as the third anchoring member 230, first negative pressure port 310, second negative pressure port 330, etc.); or the like, in such a way that such one or more elements of the hysteroscopic system 100 (e.g., the main assembly 200, uterine assembly 300, etc.) are not readily or easily movable, slidable, or the like, relative to the cavity and/or wall forming the cavity of the patient (e.g., not readily or easily movable, slidable, or the like, as compared to when the element of the hysteroscopic system 100 is not anchored; and such anchoring may be able to withstand a force of between 10N to 50N applied to such one or more elements of the hysteroscopic system 100).

The hysteroscopic system 100 also includes a uterine assembly (e.g., uterine assembly 300). The uterine assembly 300 may be formed as an elongated body 301 having an in vivo end 300*a* and an in vitro end 300*b*. The uterine assembly 300 may include one or more first negative pressure ports 310. The uterine assembly 300 may also include one or more uterine expandable members 320. The uterine assembly 300 may also include one or more second negative pressure ports 330. The uterine assembly 300 may also include one or more locking members or mechanisms (not shown). The locking member for the uterine assembly 300 may be configurable or configured to join, lock, restrict, or the like, movement of the uterine assembly 300 relative to the main assembly 200 (and may do so either in cooperation with the locking member 240 of the main assembly 200 or without use of the locking member 240 of the main assembly 200). The uterine assembly 300 is configurable or configured to cooperate with the main assembly 200 in performing a surgical action, including managing of PPH. As will be further described in the present disclosure, when in operation, the uterine assembly 300 is configurable or configured to be inserted into a main channel 202 of the main assembly 200 (from the in vitro end 200*b* of the main assembly 200) in such a way that the in vivo end 300*a* of the uterine assembly 300 is positioned outwardly away from the in vivo end 200*a* of the main assembly 200. In this regard, when the in vivo end 300*a* of the uterine assembly 300 is positioned outwardly away from the in vivo end 200*a* of the main assembly 200 (i.e., not housed in the main channel 202 of the main assembly 200, but housed in a uterine cavity of a patient (e.g., see at least FIGS. 6B-G)), at least a portion of the elongated body 301 of the uterine assembly 300 remains housed in the main channel 202 of the main assembly 200 (e.g., see at least FIGS. 6B-G). Furthermore, at least a portion of the in vitro end 300*b* of the uterine assembly 300 is not housed in the main channel 202 of the main assembly 200. As will be further described in the present disclosure, the uterine assembly 300 is configurable or configured to be anchored and/or secured in the uterine cavity of the patient (and/or anchored and/or secured relative to the uterine cavity of the patient and/or uterine walls forming the uterine cavity of the patient; also referred to herein as a "hemostasis state" or "anchored state") through one or more other elements of the hysteroscopic system 100 (e.g., via transitioning of the first negative pressure port 310 to a hemostasis state or anchored state; transitioning of the uterine expandable member to a hemostasis state or anchored state; and/or transitioning of the second negative pressure port to a hemostasis state or anchored state). The uterine assembly 300 is also configurable or configured to be non-anchored and/or non-secured (or not anchored or not secured) in the uterine cavity of the patient (and/or non-anchored and/or non-secured relative to the uterine cavity of the patient and/or uterine walls forming the uterine cavity of the patient; referred to herein as the "non-hemostasis state") through one or more other elements of the hysteroscopic system 100 (e.g., via transitioning of the first negative pressure port 310 to a non-hemostasis state or non-anchoring state; transitioning of the uterine expandable member to a non-hemostasis state or non-anchoring state; and/or transitioning of the second negative pressure port to a non-hemostasis state or non-anchoring state).

The hysteroscopic system 100 may also include a manipulator assembly (e.g., manipulator assembly 400). The manipulator assembly 400 may be formed as an elongated body 401 having an in vivo end 400*a* and an in vitro end 400*b*. The manipulator assembly 400 may include one or more end effectors 410. The manipulator assembly 400 may also include one or more expandable members (not shown) similar to or the same as the uterine expandable member 320 of the uterine assembly 300. The manipulator assembly 400 may also include one or more negative pressure ports (not shown) similar to or the same as the first negative pressure port 310 and/or second negative pressure port 330 of the uterine assembly 300. The manipulator assembly 400 may also include one or more locking members or mechanisms (not shown). The locking member for the manipulator assembly 400 may be configurable or configured to join, lock, restrict, or the like, movement of the manipulator assembly 400 relative to the main assembly 200 (and may do so either in cooperation with the locking member 240 of the main assembly 200 or without use of the locking member 240 of the main assembly 200). The manipulator assembly 400 is configurable or configured to cooperate with the main assembly 200 in performing a surgical action, including managing of PPH. As will be further described in the present disclosure, when in operation, the manipulator assembly 400 is configurable or configured to be inserted into a main channel 202 of the main assembly 200 (from the in vitro end 200b of the main assembly 200) in such a way that the in vivo end 400a of the manipulator assembly 400 is positioned outwardly away from the in vivo end 200a of the main assembly 200 so as to allow an end effector 410 of the manipulator assembly 400 to perform a surgical action in the uterine cavity of the patient. In this regard, when the in vivo end 400a of the manipulator assembly 400 is positioned outwardly away from the in vivo end 200a of the main assembly 200 (i.e., not housed in the main channel 202 of the main assembly 200, but housed in a uterine cavity of a patient (e.g., see at least FIG. 6I)), at least a portion of the elongated body 401 of the manipulator assembly 400 remains housed in the main channel 202 of the main assembly 200 (e.g., see at least FIG. 6I). Furthermore, at least a portion of the in vitro end 400b of the manipulator assembly 400 is not housed in the main channel 202 of the main assembly 200.

In an example embodiment, the uterine assembly 300 is a separate assembly from the main assembly 200. When in operation, the main assembly 200 is insertable into and anchorable in the vaginal cavity of the patient (and/or anchorable relative to the vaginal cavity of the patient and/or vaginal walls forming the vaginal cavity of the patient) (e.g., via the first anchoring member 220a, second anchoring member 220b, and/or third anchoring member 230). As will be further described in the present disclosure, a cervical seal member 210 is configurable or configured to, among other things, assist in properly positioning the main assembly 200 in the vaginal cavity of the patient.

Once the main assembly 200 is properly positioned and anchored in the vaginal cavity of the patient, the uterine assembly 300 is then insertable (or slidable) through the main channel 202 (from the in vitro end 200b of the main assembly 200) until the in vivo end 300a of the uterine assembly 300 passes through the main channel 220 and into the uterine cavity of the patient.

Once at least a portion of the in vivo end 300a of the uterine assembly 300 is provided or housed in the uterine cavity of the patient (e.g., the at least one portion of the in vivo end 300a of the uterine assembly 300 that includes the first negative pressure port 310, the uterine expandable member 320, and the second negative pressure port 330), the uterine assembly 300 is transitionable from a non-hemostasis state (or non-anchoring state) to a hemostasis state (or anchoring state), which is a state in which the hysteroscopic system 100 can commence managing PPH of the patient. More specifically, the hemostasis state (or anchoring state) of the uterine assembly 300 may be a state in which the first negative pressure port 310 has transitioned to a hemostasis state (or anchoring state) (e.g., the hemostasis state (or anchoring state) of the first negative pressure port 310 may be a state in which the first negative pressure port 310 applies a negative pressure having a magnitude greater than or equal to a threshold value (such threshold value being a sufficient amount of negative pressure to encourage, bring in, urge, and/or collapse at least a portion of the uterine cavity and/or uterine wall forming the uterine cavity towards the elongated body 301 of the uterine assembly 300)); the uterine expandable member 320 has transitioned to a hemostasis state (or anchoring state) (e.g., the hemostasis state (or anchoring state) of the uterine expandable member 320 may be a state in which the uterine expandable member 320 is expanded outwardly away from the elongated body 301 of the uterine assembly 300); and/or the second negative pressure port 330 has transitioned to a hemostasis state (or anchoring state) (e.g., the hemostasis state (or anchoring state) of the second negative pressure port 330 may be a state in which the second negative pressure port 330 applies a negative pressure having a magnitude greater than or equal to a threshold value (such threshold value being a sufficient amount of negative pressure to encourage, bring in, urge, and/or collapse at least a portion of the uterine cavity and/or uterine wall forming the uterine cavity towards the elongated body 301 of the uterine assembly 300)).

In an example embodiment, the hemostasis state (or anchoring state) of the uterine assembly 300 may be a state in which a combination of the negative pressures applied by the first negative pressure port 310 and second negative pressure port 320 is a sufficient amount of negative pressure required to encourage, bring in, urge, and/or collapse at least a portion of the uterine cavity (or uterine wall forming the uterine cavity) towards the elongated body 301 of the uterine assembly 300.

Once the uterine assembly 300 is transitioned to the hemostasis state (or anchoring state) (e.g., when the first negative pressure port 310, uterine expandable member 320, and second negative pressure port 330 are transitioned to the hemostasis state (or anchoring state)), the first negative pressure port 310 and the second negative pressure port 330 are configurable or configured in such a way that the collective negative pressure from the first negative pressure port 310 and the second negative pressure port 330 is sufficient to cause the uterine cavity and/or the uterine walls forming the uterine cavity to collapse, cave-in, envelope, shrink, or the like, inwards towards the uterine expandable member 320 (which is also transitioned to the hemostasis state (or anchoring state)). A locking mechanism 240 (and/or locking mechanism (not shown) of the uterine assembly 300) may be further configurable or configured to secure or lock the main assembly 200 (and/or movement and/or position of the main assembly 200) relative to the uterine assembly 300 so as to enable the uterine assembly 300 to be held in the homeostasis state (or anchoring state) for a prolonged period of time to manage (e.g., stop) the PPH for the patient (e.g., for between 5 minutes to over 24 hours).

As used in the present disclosure, when applicable, a reference to a hysteroscopic system 100 (and/or one or more of its elements), surgeon console (not shown) (and/or one or more of its elements), and/or controller (not shown) (and/or one or more of its elements) may also refer to, apply to, and/or include one or more computing devices, processors, servers, systems, cloud-based computing, or the like, and/or functionality of one or more processors, computing devices, servers, systems, cloud-based computing, or the like. The hysteroscopic system 100 (and/or one or more of its elements), surgeon console (and/or one or more of its elements), and/or controller (and/or one or more of its elements) may be or have any processor, server, system, device, computing device, controller, microprocessor, microcontroller, microchip, semiconductor device, or the like, configurable or configured to perform, among other things, positioning determination and/or control of one or more elements of the hysteroscopic system 100; image capturing (including video image and still image capturing); image processing (including automated image processing of video images and still images); and/or any one or more other actions, functions, methods, and/or processes described above and in the present disclosure. Alternatively or in addition, the hysteroscopic system 100 (and/or one or more of its elements), surgeon console (and/or one or more of its elements), and/or controller (and/or one or more of its elements) may include and/or be a part of a virtual machine, processor, computer, node, instance, host, or machine, including those in a networked computing environment.

These and other elements of the hysteroscopic system 100 will now be further described with reference to the accompanying figures.

The Main Assembly (e.g., Main Assembly 200).

As illustrated in at least in FIG. 3A, FIG. 3B, FIG. 3C, and FIG. 3D, the hysteroscopic system 100 includes a main assembly (e.g., main assembly 200). The main assembly 200 is configurable or configured to be inserted into and anchored in a vaginal cavity of a patient (and/or anchored relative to the vaginal cavity of the patient and/or vaginal walls forming the vaginal cavity of the patient).

To perform the actions, functions, processes, and/or methods described above and in the present disclosure, example embodiments of the main assembly 200 include one or more elements.

For example, the main assembly 200 includes and/or is formed as an elongated body 201 having an in vivo end 200a and an in vitro end 200b opposite to the in vivo end 200a. The elongated body 201 of the main assembly 200 may be formed in one or more of a variety of shapes, dimensions, configurations, etc. For example, the elongated body 201 of the main assembly 200 may be formed in the shape of a cylindrical tube, or the like, and/or with a circular, elliptical, oval, or other cross sectional shape.

The main assembly 200 also includes a main channel 202. The main channel 202 may be any channel, means, opening, passageway, pathway, tunnel, or the like, formed through the elongated body 201 of the main assembly 200 between the in vivo end 200a of the main assembly 200 and the in vitro end 200b of the main assembly 200. The main channel 202 may be formed along a first central axis of the elongated body 201 of the main assembly 200. The main assembly 200 also includes one or more cervical seal members 210. The cervical seal member 210 may be configurable or configured to properly position the main assembly 200 in a vaginal cavity of a patient (e.g., by positioning the main assembly 200 in such a way that the cervical seal member 210 abuts, is adjacent to, seals, encloses, and/or is in contact with at least a portion of a cervix (and/or surround areas of the cervix) of the patient). Alternatively or in addition, the cervical seal member 210 may be configurable or configured to isolate the uterine cavity of the patient from the vaginal cavity of the patient (e.g., by providing a separation, seal, and/or hermetic seal for the uterine cavity). The main assembly 200 also includes one or more first anchoring members 220a. The first anchoring member 220a is configurable or configured to selectively expand (when in an anchoring state) and contract (when in a non-anchoring state). The main assembly 200 also includes one or more second anchoring members 220b. Similar to the first anchoring member 220a, the second anchoring member 220b is configurable or configured to selectively expand (when in an anchoring state) and contract (when in a non-anchoring state). The main assembly 200 also includes one or more third anchoring members 230. The third anchoring member 230 is configurable or configured to provide a negative pressure (or suction). The main assembly 200 may also include one or more vaginal seal members 250 (e.g., as illustrated in at least FIGS. 2C, 2D, and 3D). The main assembly 200 may also include one or more locking members or mechanisms 240 (e.g., as illustrated in at least FIG. 1H). The main assembly 200 may also include one or more first extendible members 260 (e.g., as illustrated in at least FIG. 3B).

These and other elements of the main assembly 200 will now be further described with reference to the accompanying figures.

The Elongated Body of the Main Assembly (e.g., Elongated Body 201).

As illustrated in at least FIGS. 1A-1H and 2A-2D, the main assembly 200 includes an elongated body of the main assembly (e.g., elongated body 201). The elongated body 201 of the main assembly 200 may be configurable or configured to function as a core structure to provide structural rigidity for the main assembly 200, and to position one or more elements of the hysteroscopic system 100 to perform one or more actions. The elongated body 201 of the main assembly 200 may be configurable or configured to support each element of the main assembly 200 (e.g. the cervical seal member 210, the first anchoring member 220a, the second anchoring member 220b, the third anchoring member 230, the locking member 240, the vaginal seal member 250, the first extendible member 260, etc.). The elongated body 201 of the main assembly 200 is formed having sufficient rigidity so as to not bend, collapse, or deform when in operation, including not bend, collapse, or deform when: the cervical seal member 210 provides a separation, seal, and/or hermetic seal; the first anchoring member 220a is in the anchoring state (and/or is transitioned to and/or from the anchoring state); the second anchoring member 220b is in the anchoring state (and/or is transitioned to and/or from the anchoring state); the third anchoring member 230 is in the anchoring state (and/or is transitioned to and/or from the anchoring state); and/or when the vaginal seal member 250 provides a separation, seal, and/or hermetic seal.

The elongated body 201 of main assembly 220 may be formed as a tubular shaped member, cylindrical shaped member, hollow member, square tubular shaped member, etc.

The Cervical Seal Member (e.g., Cervical Seal Member 210).

As illustrated in at least FIGS. 1A-1H, 2A-2D, and 3A-3D, and FIG. 4A, FIG. 4B, FIG. 4C, FIG. 4D, FIG. 4E, FIG. 4F, FIG. 4G, and FIG. 4H, the main assembly 200 includes one or more cervical seal members (e.g., cervical seal member 210). The cervical seal member 210 may be configurable or configured to separate, isolate, seal, and/or hermetically seal a uterine cavity of a patient from a vaginal cavity of the patient. Alternatively or in addition, the cervical seal member 210 may be configurable or configured to ensure the main assembly 200 does not enter into the uterine cavity of the patient. Alternatively or in addition, the cervical seal member 210 may be configurable or configured to properly position the main assembly 200 within the vaginal cavity of the patient.

The cervical seal member 210 may be formed at the in vivo end 200a of the main assembly 200. In example embodiments, the cervical seal member 210 includes a central axis that is coaxial to the central axis of the main assembly 200 (and/or central axis of the main channel 202). The cervical seal member 210 may be introduced transvaginally to abut, contact, seal, and/or hermetically seal a cervix (and/or surrounding areas of the cervix) of a patient. The cervical seal member 210 may be formed along a plane that is orthogonal or substantially orthogonal to the main channel 202 (and/or a central axis formed through the main channel 202). The cervical seal member 210 may include an outermost edge portion (or perimeter portion or rim portion) formed between the contact wall 212 and non-contact wall 214 of the cervical seal member 210. Such outermost edge portion of the cervical seal member 210 may be formed along a plane that is orthogonal or substantially orthogonal to the main channel 202 (and/or a central axis formed through the main channel 202).

To perform the actions, functions, processes, and/or methods described above and in the present disclosure, example embodiments of the cervical seal member 210 includes one or more elements and/or characteristics. For example, the cervical seal member 210 includes one or more contact walls 212. In some embodiments, the cervical seal member 210 may also include one or more non-contact walls 214. In some embodiments, the cervical seal member 210 may also include one or more sealable members 216 (e.g., a gel sheet, plate, or the like, capable of allowing one or more elements of the hysteroscopic system 100 (e.g., the uterine assembly 300) to pass through, while also providing a seal around the portion of the element that is passed through). In some embodiments, the cervical seal member 210 may also include one or more suction module 218 (e.g., negative pressure openings or ports that provide negative pressure or suction).

The Contact Wall of the Cervical Seal Member (e.g., Contact Wall 212).

Figure 4A:
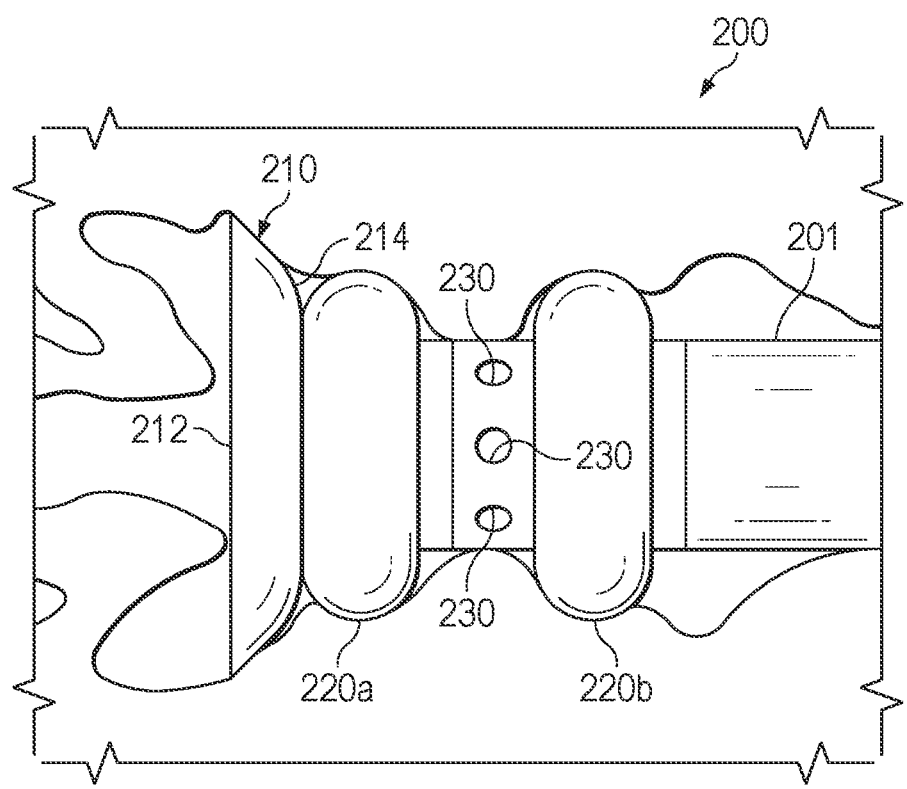
FIG. 4A is an illustration of a main assembly (anchoring state) having an example embodiment of a cervical seal member with a shallow concave or dish-like shaped contact wall.
Figure 4B:
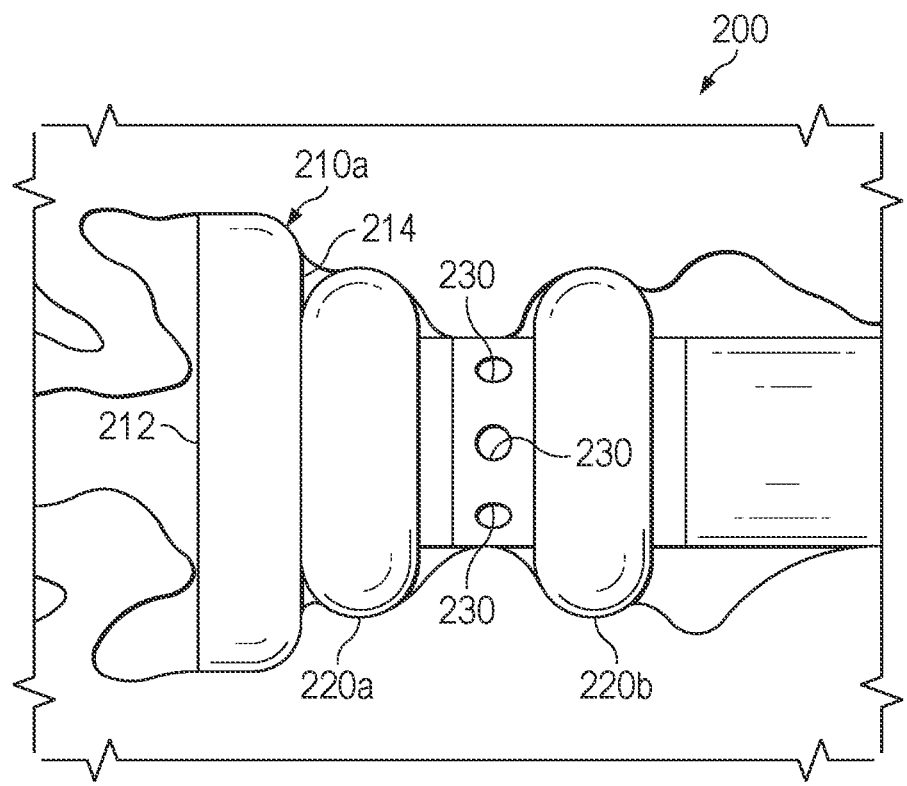
FIG. 4B is an illustration of a main assembly (anchoring state) having another example embodiment of a cervical seal member with a deeper concave or bowl-like shaped contact wall.
Figure 4C:
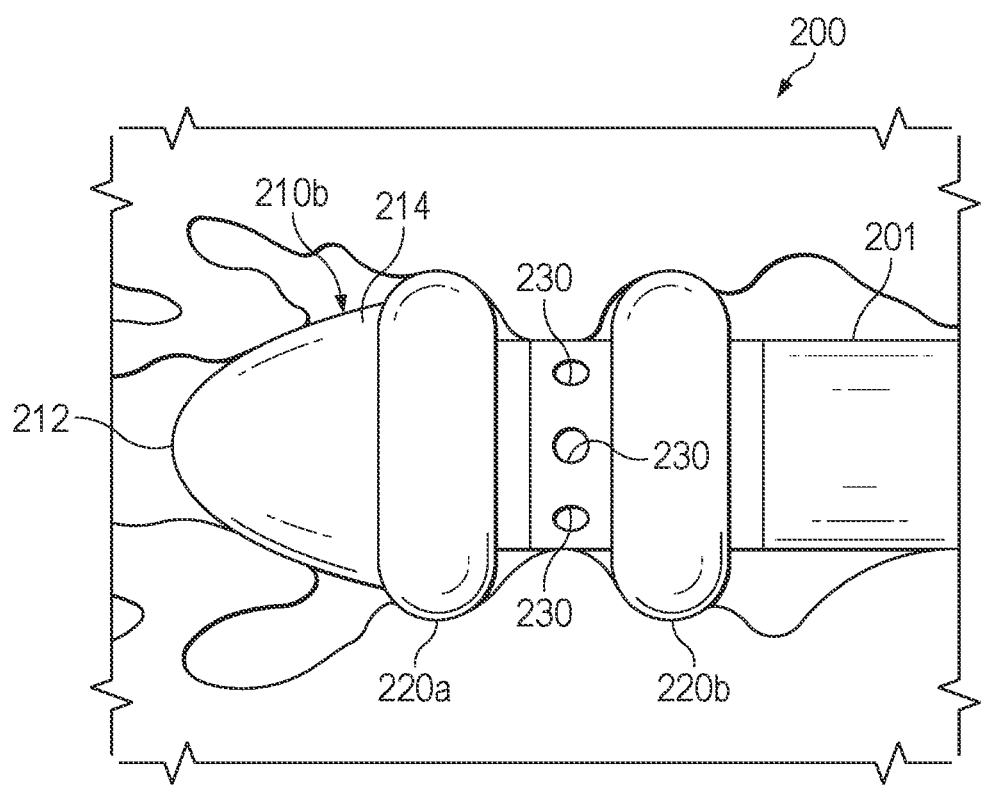
FIG. 4C is an illustration of a main assembly (anchoring state) having another example embodiment of a cervical seal member with an oval or convex shaped contact wall.
Figure 4D:
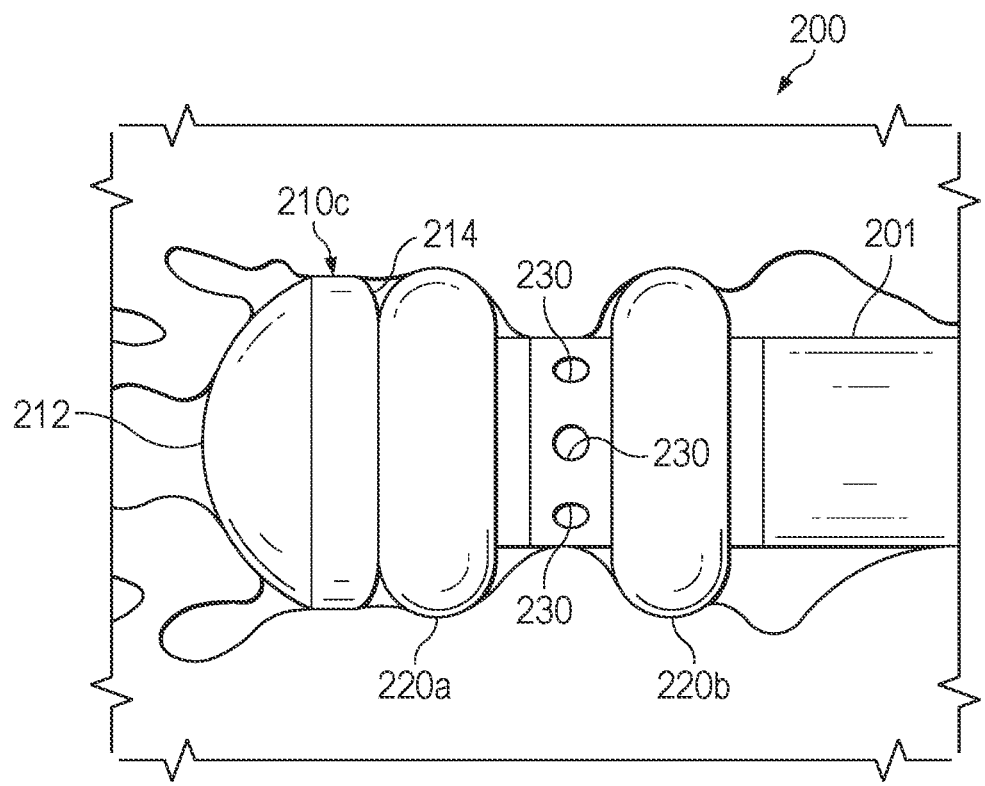
FIG. 4D is an illustration of a main assembly (anchoring state) having another example embodiment of a cervical seal member with a spherical or convex shaped contact wall.
Figure 4E:
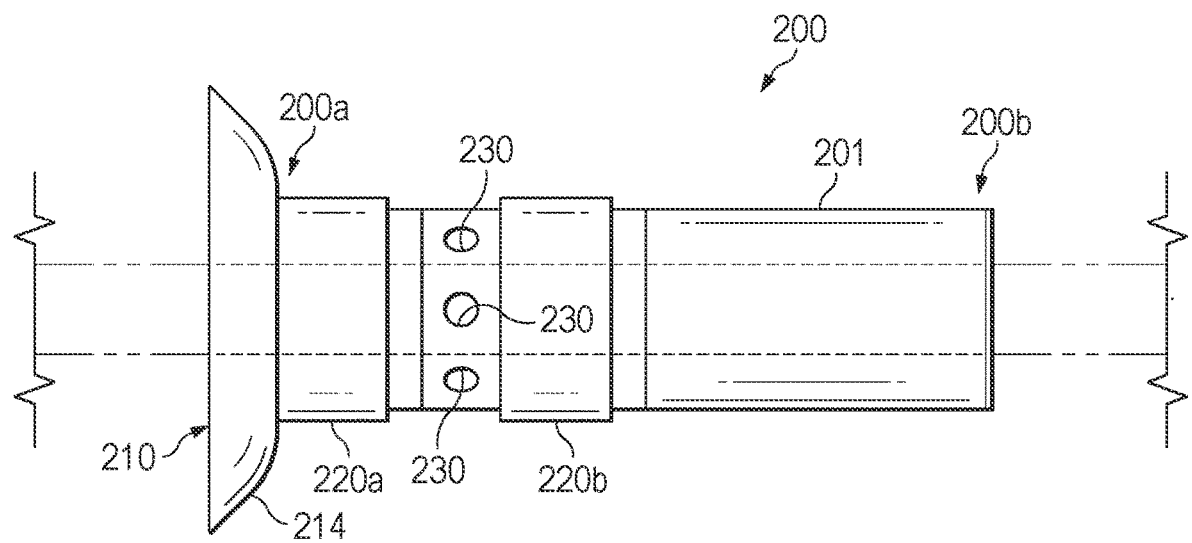
FIG. 4E is an illustration of a side view of a main assembly.
Figure 4F:
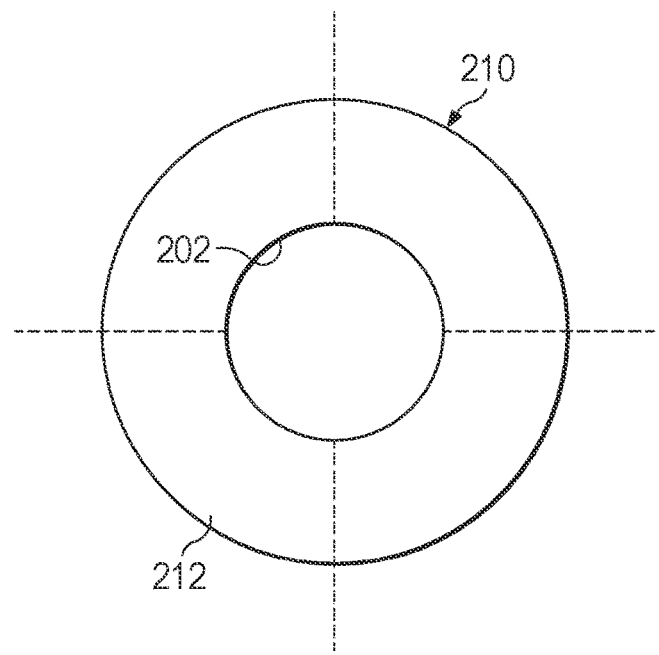
FIG. 4F is an illustration of a front view of a main assembly having a main channel.
Figure 4G:
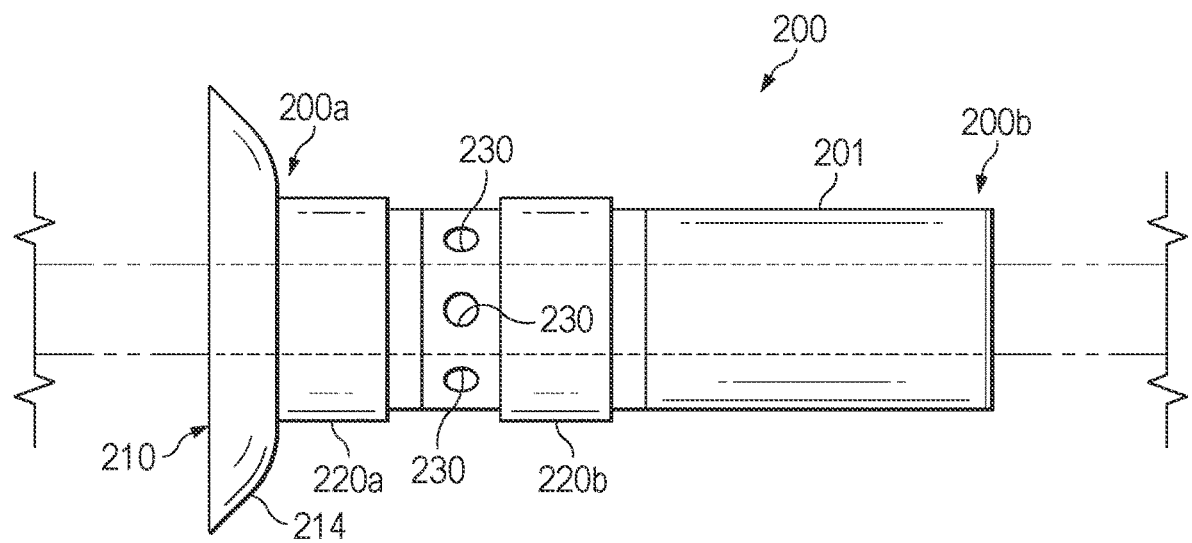
FIG. 4G is illustration of a side view of a main assembly.
Figure 4H:
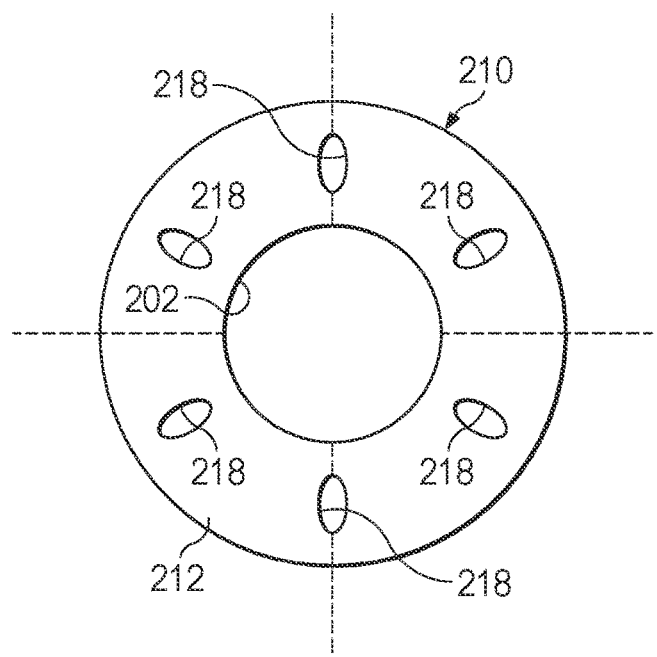
FIG. 4H is illustration of a front view of a main assembly having one or more suction modules on the cervical seal member.

As illustrated in at least FIGS. 1A-H and 4A-H, the cervical seal member 210 includes one or more contact walls 212. The contact wall 212 of the cervical seal member 210 may be configurable or configured to contact with at least a portion of the cervix of the patient. When contacting with at least a portion of the cervix of the patient, the contact wall 212 may separate, isolate, and/or hermetically seal the uterine cavity of the patient from the vaginal cavity of the patient (e.g., in cooperation with the sealable member 216 and/or one or more other elements of the hysteroscopic system 100, such as the uterine assembly 300). The contact wall 212 of the cervical seal member 210 may include a circular contact portion (and/or any other geometrical shape). The circular contact portion of the contact wall 212 may be formed along a plane that is substantially orthogonal to a central axis formed through the main channel 202 (also referred to herein as the first central axis). The contact wall 212 of the cervical seal member 210 may include at least a portion that is formed in a concave shape. Alternatively or in addition, the contact wall 212 of the cervical seal member 210 may include at least a portion that is formed in a convex shape, curve shape, rounded shape, etc. In some embodiments, the contact wall 212 of the cervical seal member 210 may be formed in a concave or dish-like shape (e.g., as illustrated in FIG. 4A). In some embodiments, the contact wall 212 of the cervical seal member 210a may be formed in a deeper concave or bowl-like shape (e.g., as illustrated in FIG. 4B). In some embodiments, the contact wall 212 of the cervical seal member 210b may be formed in a convex or oval-like shape (e.g., as illustrated in FIG. 4C). In some embodiments, the contact wall 212 of the cervical seal member 210c may be formed in a convex or sphere-like shape (e.g., as illustrated in FIG. 4D). In some embodiments, the contact wall 212 of the cervical seal member 210 may be formed in a ball-like shape (not shown) and/or other geometrical shapes (not shown) that can be closely contacted with at least a portion of the cervix of a patient. In some example embodiments, the contact wall 212 of the cervical seal member 210 is in a dish-like shape having a circular contact portion (e.g., as illustrated in FIGS. 4E and 4G). In some example embodiments, the circular contact portion of the contact wall 212 of the cervical seal member 210 may be formed along a plane that is orthogonal or substantially orthogonal to the main channel 202 (and/or a central axis formed through the main channel 202) (e.g., as illustrated in FIG. 4F). In some example embodiments, the circular contact portion of the contact wall 212 of the cervical seal member 210 may have one or more suction modules 218 on the cervical seal member 210 (e.g., as illustrated in FIG. 4H). The contact wall 212 and/or non-contact wall 214 of the cervical seal member 210 may include one or more flexible portions (e.g., the outermost edge portion formed between the contact wall 212 and non-contact wall 214). The at least one flexible portion of the contact wall 212 and/or non-contact wall 214 of the cervical seal member 210 is configured to dynamically adapt to a surface topology of the cervix of the patient (and/or provide a seal and/or hermetic seal).

The Non-Contact Wall of the Cervical Seal Member (e.g., Non-Contact Wall 214).

In an example embodiment, the cervical seal member 210 may also include a non-contact wall 214. The non-contact wall 214 of the cervical seal member 210 may be opposite to the contact wall 212 of the cervical seal member 210. The non-contact wall 214 of the cervical seal member 210 may be adjacently positioned next to the first anchoring member 220a. The non-contact wall 214 of the cervical seal member 210 may include one or more portions formed in a concave shape. Alternatively or in addition, the non-contact wall 214 of the cervical seal member 210 may include at least a portion that is formed in a convex shape, curve shape, rounded shape, etc. In some example embodiments, the non-contact wall 214 of the cervical seal member 210 includes at least a portion that is formed in a convex shape. The non-contact wall 214 of the cervical seal member 210 may be formed along a plane that is orthogonal or substantially orthogonal to the main channel 202 (and/or a central axis formed through the main channel 202).

The Sealable Member of the Cervical Seal Member (e.g., Sealable Member 216).

As illustrated in at least FIGS. 1A-H, the cervical seal member 210 may also include one or more sealable members 216. The sealable member 216 may be configurable or configured to dynamically adjust or transition between an opening state (e.g., a state in which one or more elements of the hysteroscopic system 100 are provided through the sealable member 216) and a closed state (e.g., a state in which no elements of the hysteroscopic system 100 are provided through the sealable member 216).

For example, when a uterine assembly 300 is provided through the sealable member 216 (opening state), the sealable member 216 is configurable or configured to provide a hermetic seal around the uterine assembly 300 (or the portion of the uterine assembly 300 provided through the sealable member 216). The sealable member 216 may be configurable or configured to allow the uterine assembly 300 to slide or pass through in both directions (opening state). As another example, when a manipulator assembly 400 is provided through the sealable member 216 (opening state), the sealable member 216 is configurable or configured to provide a hermetic seal around the manipulator assembly 400 (or the portion of the manipulator assembly 400 provided through the sealable member 216). The sealable member 216 may be configurable or configured to allow the manipulator assembly 400 to slide or pass through in both directions (opening state). The sealable member 216 may be configurable or configured to hermetically seal itself when the manipulator assembly 400 is not provided through the sealable member 216 (closed state). The sealable member 216 may be formed coaxial to the cervical seal member 210 (and/or a central axis formed through the cervical seal member 210). Alternatively or in addition, the sealable member 216 may be formed coaxial to the main channel 202 (and/or a central axis formed through the main channel 202). The Suction Module of the Cervical Seal Member (e.g., Suction Module 218).

Figure 1C:
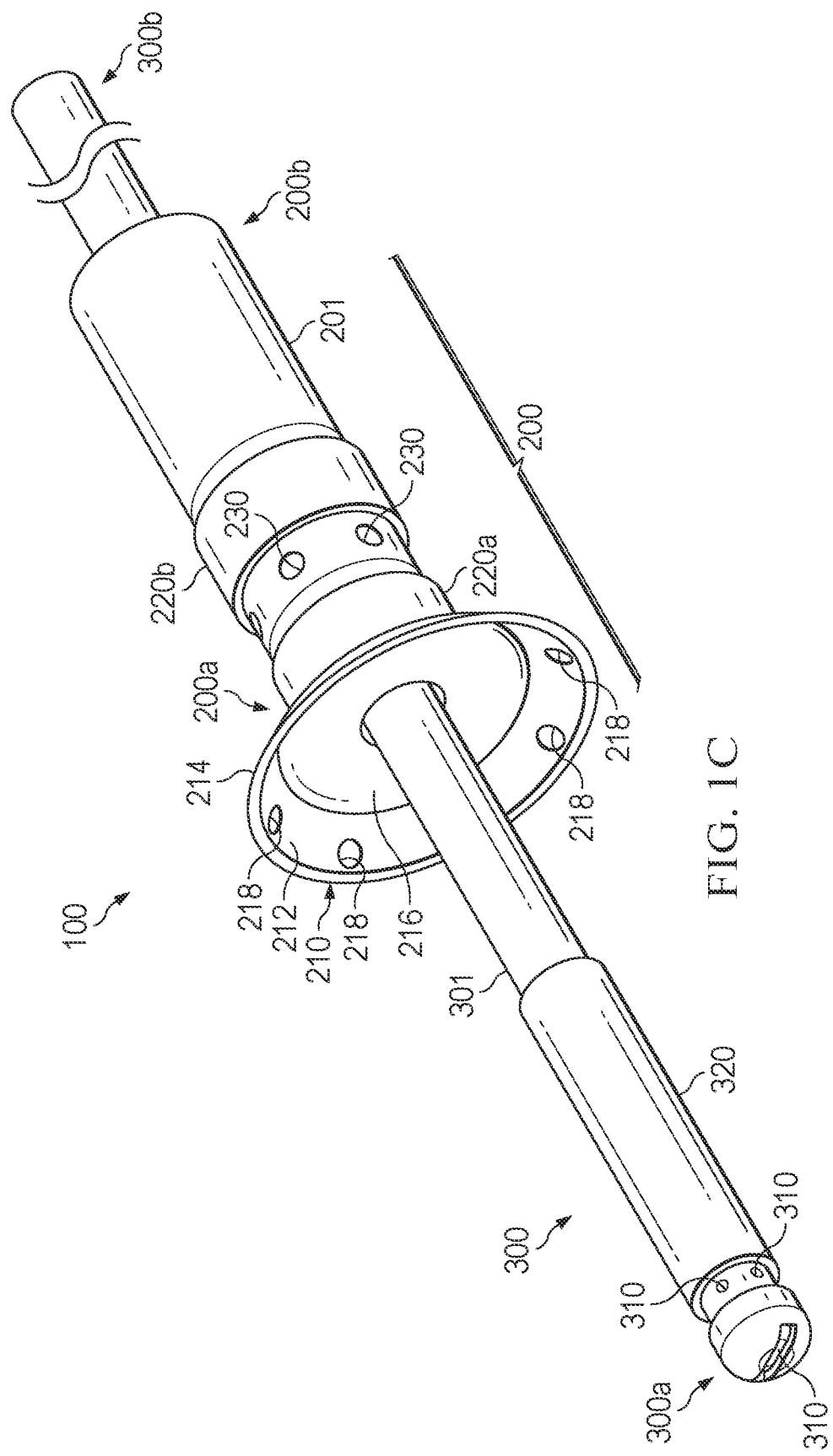
FIG. 1C is another illustration of a perspective view of an embodiment of a hysteroscopic system (with main assembly in non-anchoring state and uterine assembly in non-haemostasis state) for managing post-partum hemorrhaging.
Figure 1D:
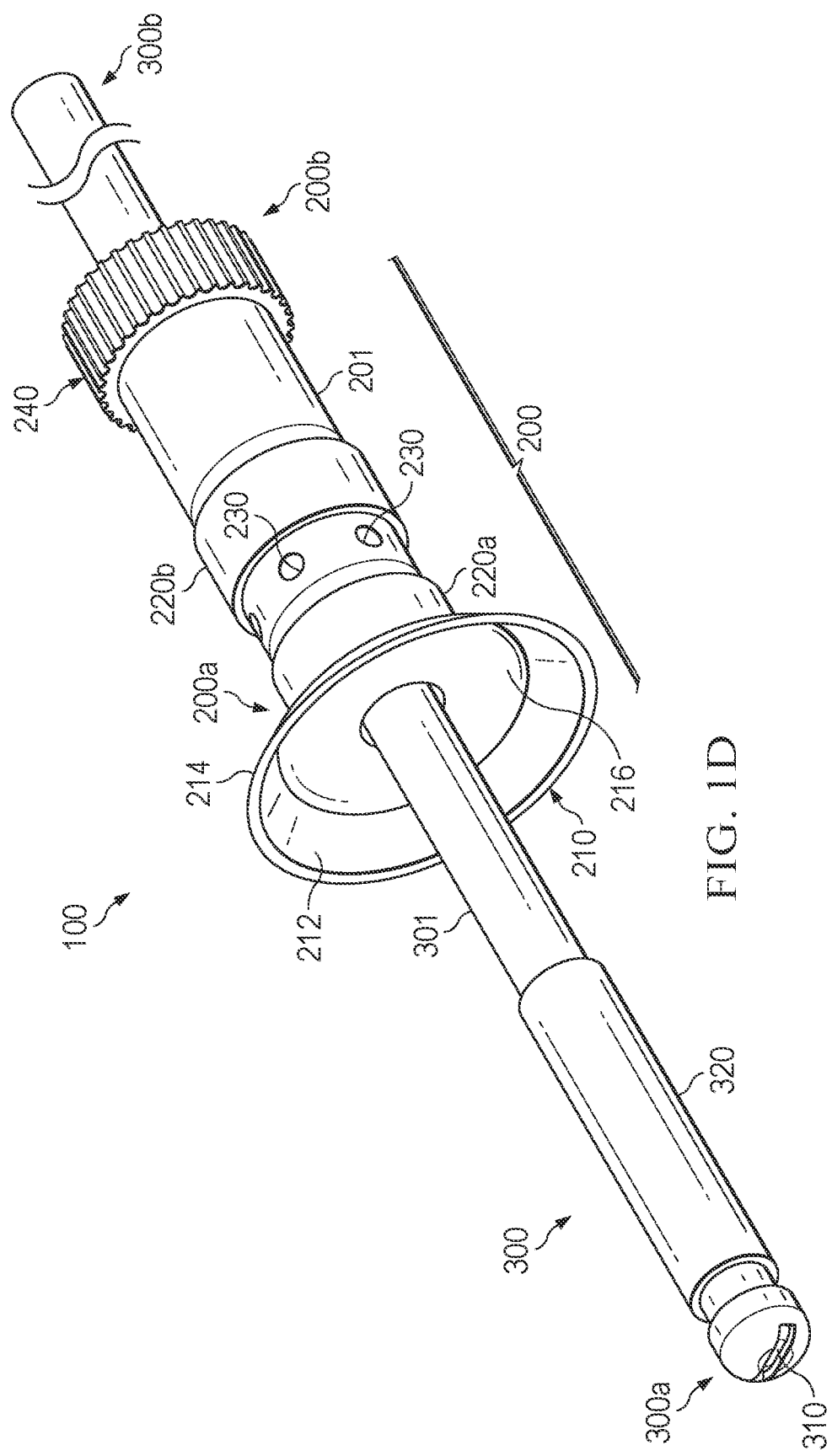
FIG. 1D is another is an illustration of a perspective view of an embodiment of a hysteroscopic system (with main assembly in non-anchoring state and uterine assembly in non-haemostasis state) for managing post-partum hemorrhaging.
Figure 1E:
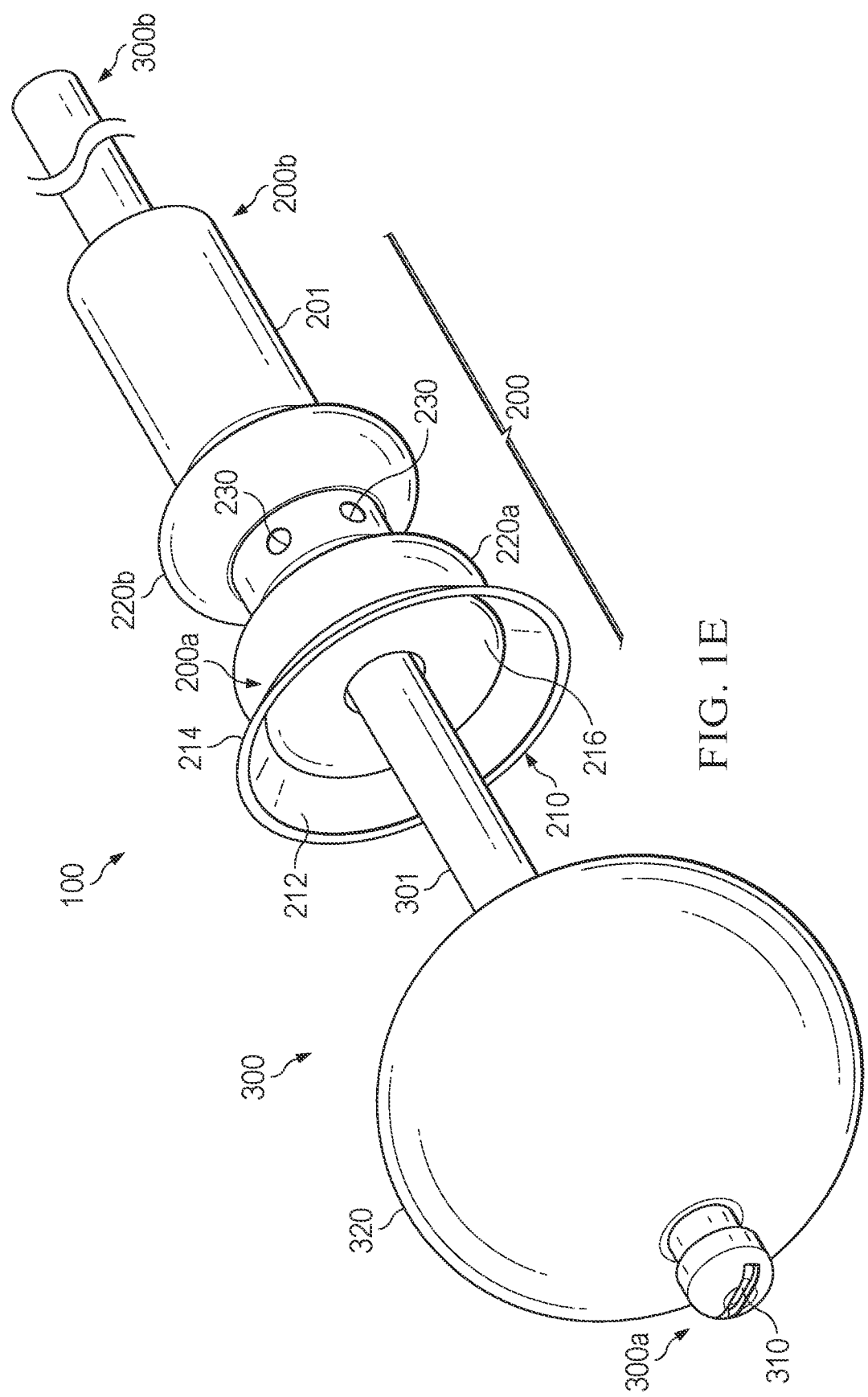
FIG. 1E is another illustration of a perspective view of an example embodiment of a hysteroscopic system (with main assembly in anchoring state and uterine assembly in haemostasis state) for managing post-partum hemorrhaging.
Figure 1F:
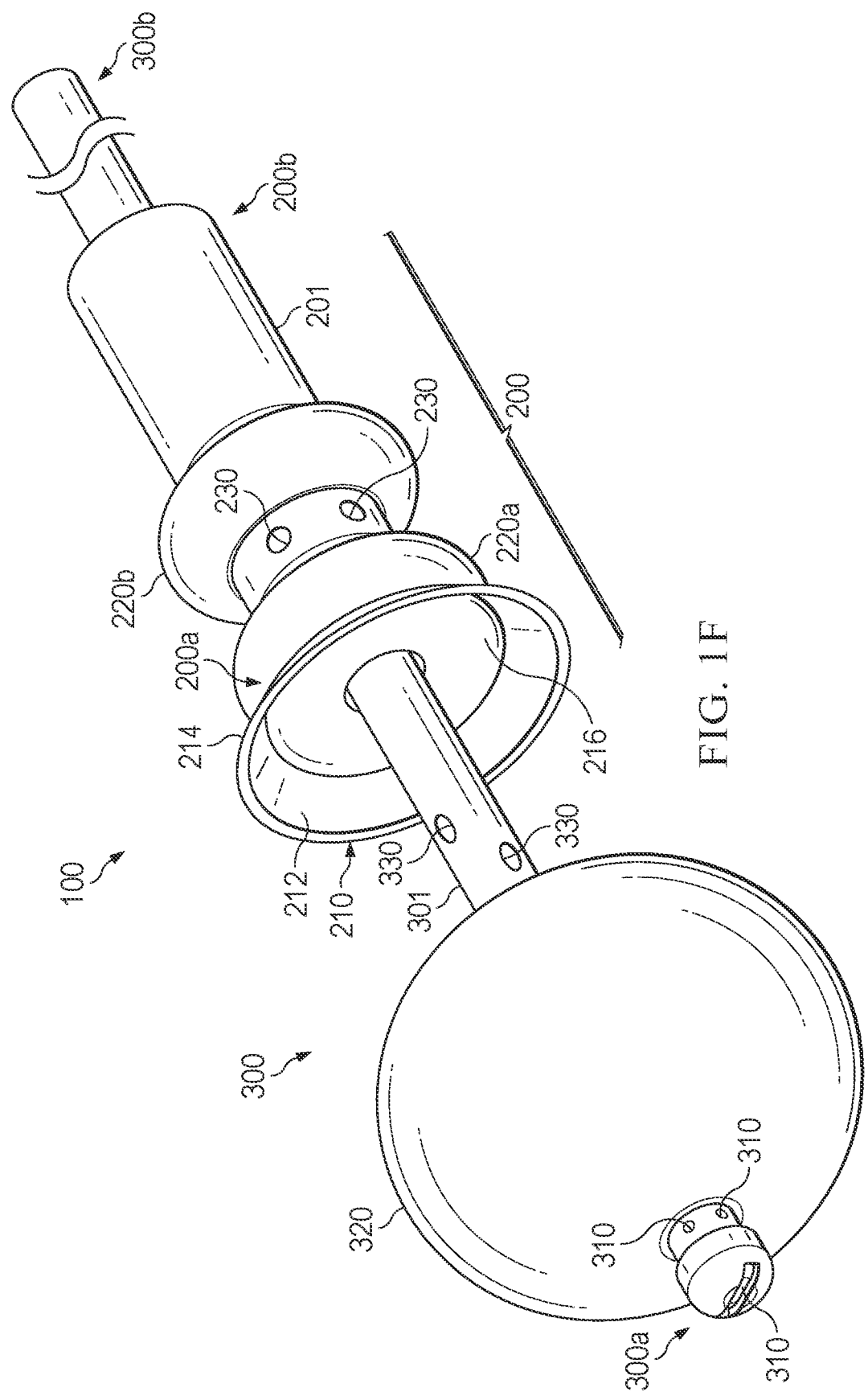
FIG. 1F is another illustration of a perspective view of an example embodiment of a hysteroscopic system (with main assembly in anchoring state and uterine assembly in haemostasis state) for managing post-partum hemorrhaging.
Figure 1G:
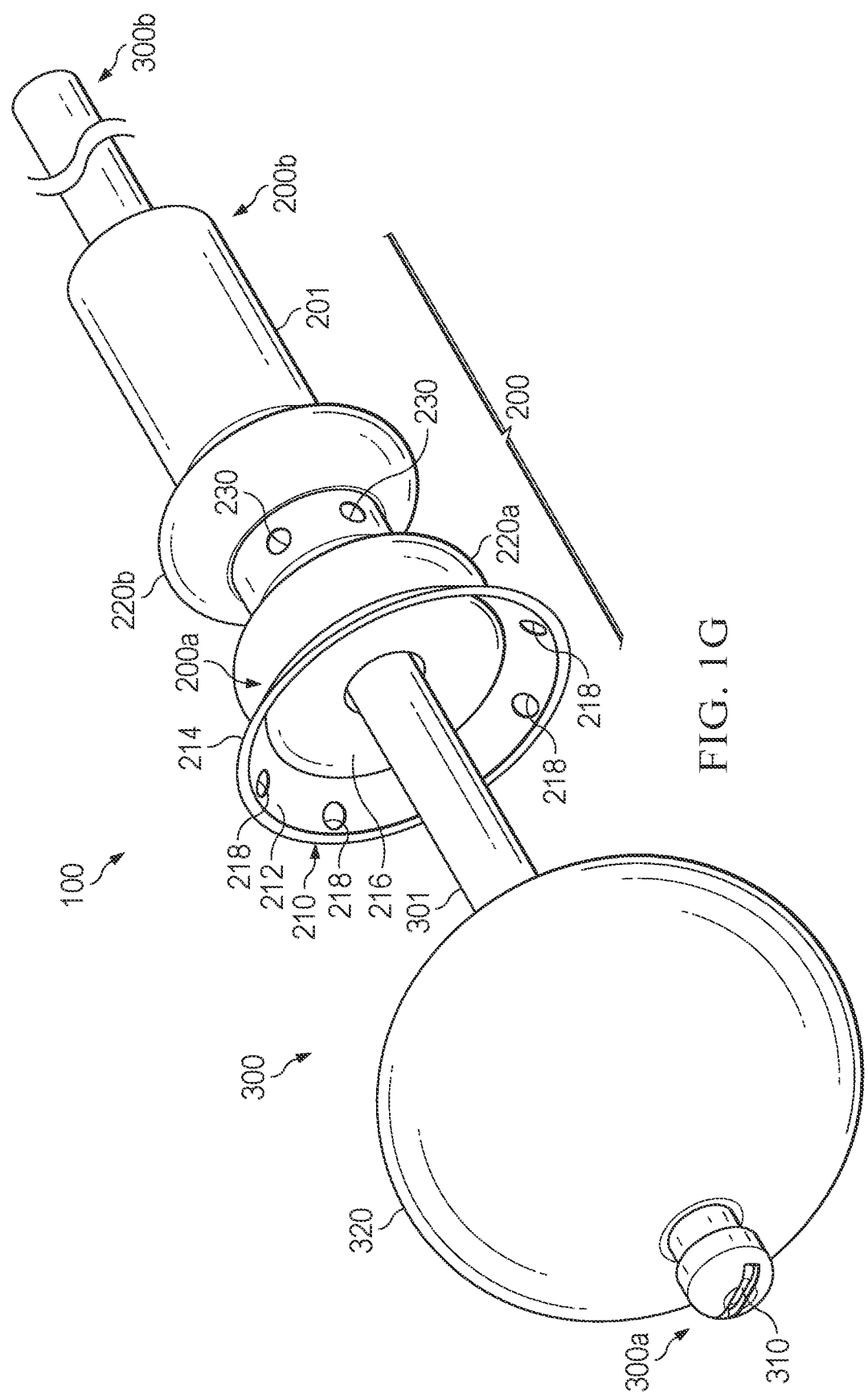
FIG. 1G is another illustration of a perspective view of an example embodiment of a hysteroscopic system (with main assembly in anchoring state and uterine assembly in haemostasis state) for managing post-partum hemorrhaging.
Figure 1H:
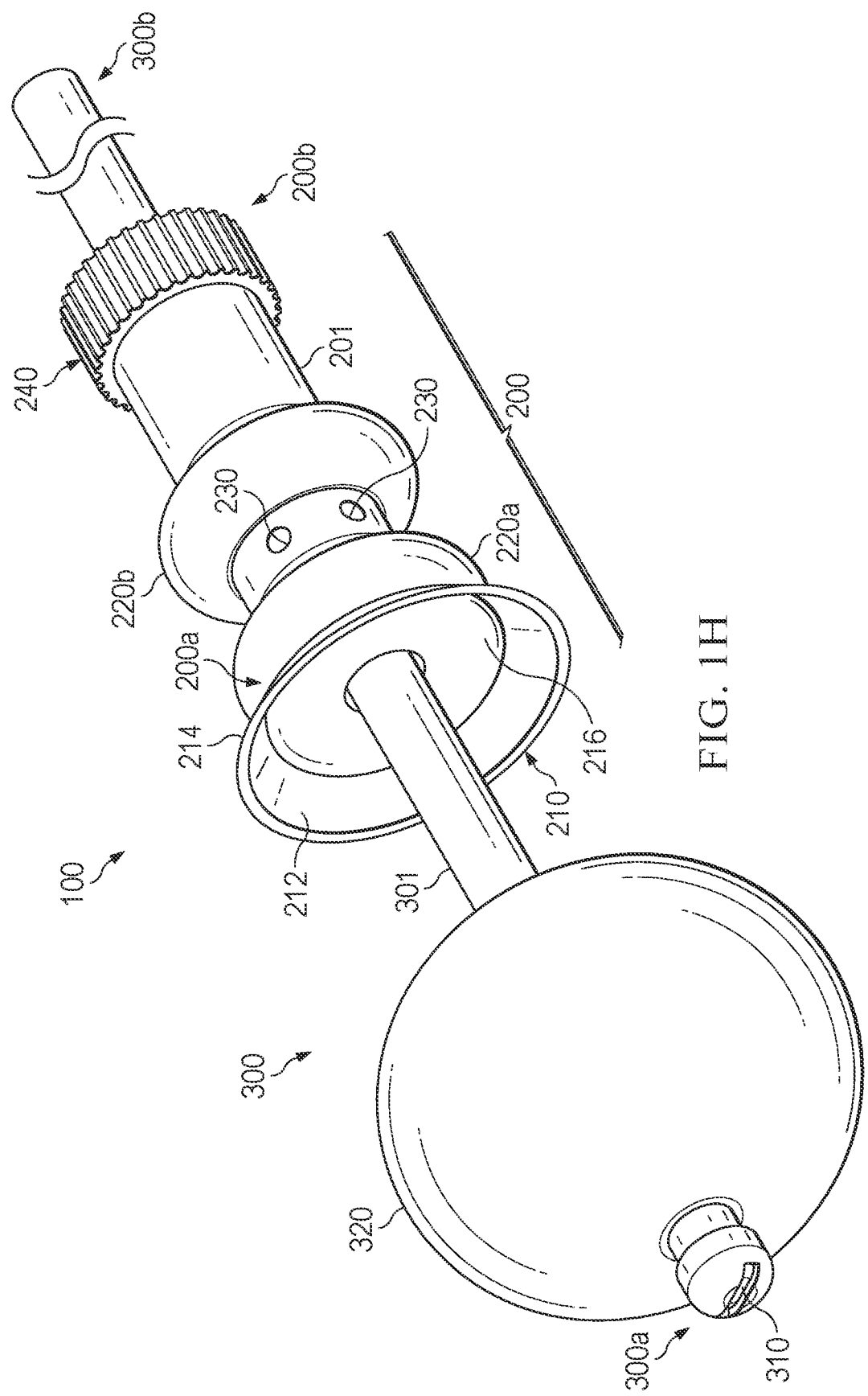
FIG. 1H is another illustration of a perspective view of an example embodiment of a hysteroscopic system (with main assembly in anchoring state and uterine assembly in haemostasis state) for managing post-partum hemorrhaging.
Figure 2A:
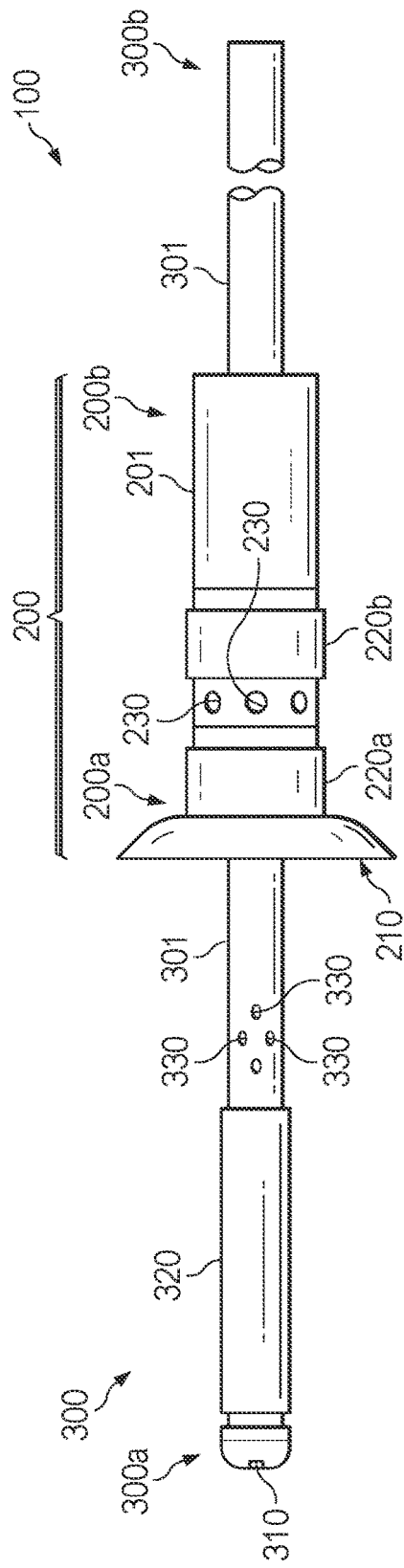
FIG. 2A is an illustration of a side view of an example embodiment of a hysteroscopic system (with main assembly in non-anchoring state and uterine assembly in non-haemostasis state) for managing post-partum hemorrhaging.
Figure 2B:
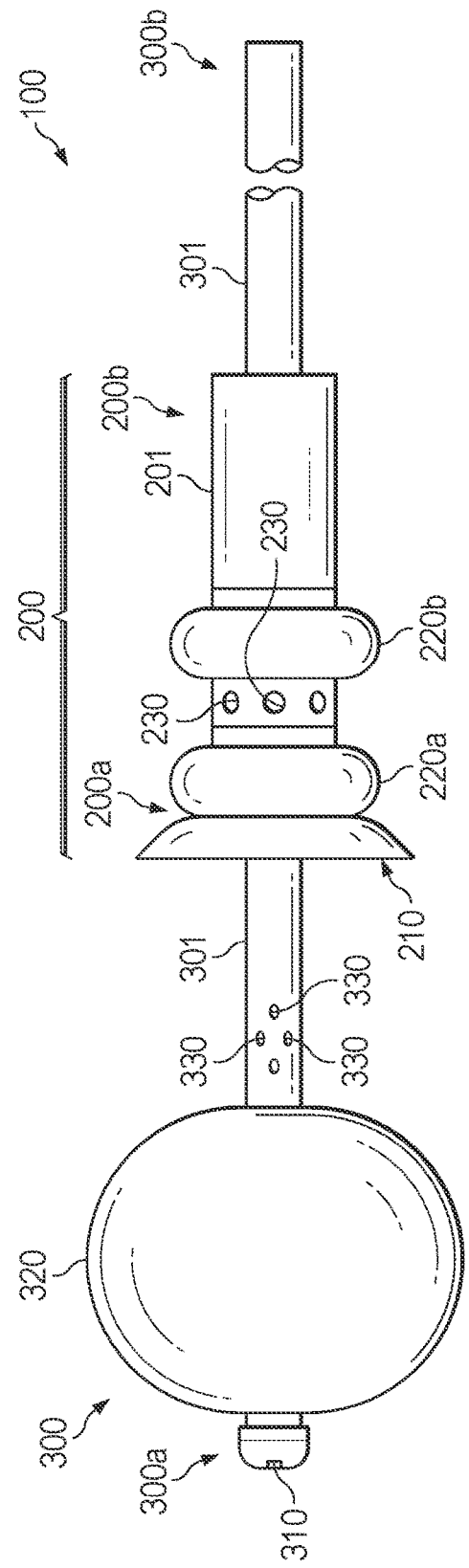
FIG. 2B is another illustration of a side view of an example embodiment of a hysteroscopic system (with main assembly in anchoring state and uterine assembly in haemostasis state) for managing post-partum hemorrhaging.

As illustrated in at least FIGS. 1C and 4H, the cervical seal member 210 may also include one or more suction modules 218. The one or more suction modules 218 may be formed on the contact wall 212 of the cervical seal member 210. The one or more suction modules 218 may be configurable or configured to provide a negative pressure. When in operation, such negative pressure may enable or facilitate a seal and/or hermetic seal between the cervical seal member 210 and a cervix of the patient (and/or uterine wall and/or vaginal wall of the patient). The one or more suction modules 218 may also enable or facilitate a collapse or compression at least a portion of the uterine wall, cervix, and/or vaginal wall of the patient.

In an example embodiment, the cervical seal member 210 may be adjustable in one or more directions, orientation, shapes, and/or sizes so as to adjustably contact with the cervix of the patient (and/or surrounding areas around the cervix). A dimension and/or size of the cervical seal member 210 may be greater than an overall size of the cervix so as to seal a uterine cavity of the patient. For example, the cervical seal member 210 may have a diameter of between 50 to 120 mm, or more or less. In some embodiments, the cervical seal member 210 may have a diameter of between 60 to 80 mm. In some embodiments, the cervical seal member 210 may have an outside diameter of about 70 mm.

In example embodiments, the cervical seal member 210 may be formed partially or completely of medical grade rubber, starch, silicone, polymer or copolymer including polyvinyl chloride (PVC), polypropylene (PP), polyethylene (PE), polystyrene (PS), polymethacrylate (PMMA), polyacrylonitrile, or combination thereof. The cervical seal member 210 may be formed with sufficient rigidity so as to maintain its original shape, while also having sufficient flexibility so as to enable the cervical seal member 210 to provide a seal and/or hermetic seal around the cervix of the patient when in operation. The cervical seal member 210 may include elastic and flexible properties so that, when introduced trans-vaginally to contact with a cervix of a patient, the cervical seal member 210 may conform and/or adjusted to fit the patient's body without causing injuries.
The First Anchoring Member (e.g., First Anchoring Member 220a).

As illustrated in at least FIGS. 1A-H, 2A-D, 3A-D, 4A-E, and 4G, the main assembly 200 includes a first anchoring member (e.g., first anchoring member 220a). The first anchoring member 220a may be formed on (and/or attached to, formed with, etc.) the elongated body 201 of the main assembly 200. The first anchoring member 220a may be configurable or configured to expand or protrude outwardly away from the elongated body 201 of the main assembly 200. For example, the first anchoring member 220a may be an expandable and/or inflatable member configurable or configured to expand when a positive pressure, gas, liquid, and/or solid is introduced in the first anchoring member 220a (e.g., from an external source (not shown)). In an example embodiment, the first anchoring member 220a is configurable or configured to provide a vaginal tamponade in at least a portion of the vaginal cavity (or vaginal wall forming the vaginal cavity). The first anchoring member 220a may be formed adjacent to the cervical seal member 210. The first anchoring member 220a may be configurable or configured to transition between an anchoring state and a non-anchoring state. In an example embodiment, a default state (or initial state or normal state before anchoring) of the first anchoring member 220a is the non-anchoring state.

When transitioning the first anchoring member 220a from a non-anchoring state to the anchoring state, the first anchoring member 220a may receive a positive pressure, gas, liquid, and/or solid so as to expand and/or protrude to a first overall volume and/or diameter (e.g., expanded outwardly away from the elongated body 201 of the main assembly 200 towards the wall of the vaginal cavity).

When transitioning the first anchoring member 220a from the anchoring state to the non-anchoring state, the first anchoring member 220a may receive a negative pressure (or not receive a positive pressure, gas, liquid, and/or solid; and/or remove positive pressure, gas, liquid, and/or solid) so as to contract and/or reduce to a second overall volume (e.g., not expanded as outwardly away from the elongated body 201 of the main assembly 200 as compared to the anchoring state). In this regard, the second overall volume is less than the first overall volume.

In another embodiment, a volume, shape, and/or size of the first anchoring member 220a can be selectively adjustable in one or more directions. The first anchoring member 220a may be in the form of an inflatable or expandable member that can be expanded or inflated with and/or receive and retain a gas, gaseous mixture, pressure, air, water, oil, liquid, semi-solid, etc. In some example embodiments, the first anchoring member 220a may be in the form of an inflatable balloon member, expandable member, or the like. The first anchoring member 220a may be made of surgical grade materials (e.g., medical grade polyurethane, silicone, polycaprolactone, or the like).
The Second Anchoring Member (e.g., Second Anchoring Member 220b).

As illustrated in at least FIGS. 1A-H, 2A-D, 3A-D, 4A-E, and 4G, the main assembly 200 includes a second anchoring member (e.g., second anchoring member 220b). The second anchoring member 220b may be formed on (and/or attached to, formed with, etc.) the elongated body 201 of the main assembly 200. The second anchoring member 220b may be configurable or configured to expand or protrude outwardly away from the elongated body 201 of the main assembly 200. For example, the second anchoring member 220b may be an expandable and/or inflatable member configurable or configured to expand when a positive pressure, gas, liquid, and/or solid is introduced in the first anchoring member 220a (e.g., from an external source (not shown)). In an example embodiment, the second anchoring member 220b is configurable or configured to provide a vaginal tamponade in at least a portion of the vaginal cavity (or vaginal wall forming the vaginal cavity). The second anchoring member 220b may be formed adjacent to the third anchoring member 230 in such a way that the third anchoring member 230 is provided between the first anchoring member 220a and the second anchoring member 220b. The second anchoring member 220b may be configurable or configured to transition between an anchoring state and a non-anchoring state. In an example embodiment, a default state (or initial state or normal state before anchoring) of the second anchoring member 220b is the non-anchoring state.

When transitioning the second anchoring member 220b from a non-anchoring state to the anchoring state, the second anchoring member 220b may receive a positive pressure, gas, liquid, and/or solid so as to and/or protrude to a third overall volume and/or diameter (e.g., expanded outwardly away from the elongated body 201 of the main assembly 200 towards the wall of the vaginal cavity).

When transitioning the second anchoring member 220b from the anchoring state to the non-anchoring state, the second anchoring member 220b may receive a negative pressure (or not receive a positive pressure, gas, liquid, and/or solid; and/or remove positive pressure, gas, liquid, and/or solid) so as to contract and/or reduce to a fourth overall volume (e.g., not expanded as outwardly away from the elongated body 201 of the main assembly 200 as compared to the anchoring state). In this regard, the fourth overall volume is less than the third overall volume. In example embodiments, the third overall volume may be the same as or similar to the first overall volume. Alternatively or in addition, the fourth overall volume may be the same as or similar to the second overall volume in example embodiments.

In another embodiment, a volume, shape, and/or size of the second anchoring member 220b can be selectively adjustable in one or more directions. The second anchoring member 220b may be in the form of an inflatable or expandable member that can be inflated with and/or receive and retain a gas, gaseous mixture, pressure, air, water, oil, liquid, semi-solid, etc. In some example embodiments, the second anchoring member 220b may be in the form of an inflatable balloon member, expandable member, or the like. The second anchoring member 220b may be made of surgical grade materials (e.g., surgical grade polyurethane, silicone, polycaprolactone, or the like).

The Third Anchoring Member (e.g., Third Anchoring Member 230).

As illustrated in at least FIGS. 1A-H, 2A-D, 3A-D, 4A-E, and 4G, the main assembly 200 includes one or more third anchoring members (e.g., third anchoring member 230). The third anchoring member 230 may be formed or provided on the elongated body 201 of the main assembly 200 between the first and second anchoring members 220a, 220b. The third anchoring member 230 may be configurable or configured to provide a negative pressure. As described in the present disclosure, when the main assembly 200 is housed in a vaginal cavity of a patient, the third anchoring member 230 is configurable or configured to provide a negative pressure towards at least a portion of the vaginal cavity (or vaginal wall forming the vaginal cavity) in such a way as to collapse, contract, shrink, narrow, and/or condense at least a portion of the vaginal cavity (and/or vaginal wall forming the vaginal cavity) towards the elongated body 201 of the main assembly 200. In some example embodiments, the third anchoring member 230 may also be configurable or configured to provide positive pressure so as to bring the vaginal cavity (or vaginal wall forming the vaginal cavity) back to its normal shape when needed (e.g., after completing a surgical action, such as treating PPH).

In an example embodiment, the third anchoring member 230 may be configurable or configured to transition between an anchoring state and a non-anchoring state. The anchoring state of the third anchoring member 230 is a state in which the third anchoring member 230 applies at least a first negative pressure. The first negative pressure is an amount of negative pressure required to collapse at least a portion of the vaginal cavity (or vaginal wall forming the vaginal cavity) towards the elongated body 201 of the main assembly 200. The non-anchoring state of the third anchoring member 230 is a state in which the third anchoring member 230 does not apply at least the first negative pressure (e.g., the third anchoring member 230 does not apply any negative pressure).

In an example embodiment, the elongated body 201 of the main assembly 200 is formed having sufficient rigidity so as to not bend, collapse, or deform when the third anchoring member 230 applies negative pressure (or applies suction). Alternatively or in addition, when the third anchoring member 230 applies negative pressure (e.g., the first negative pressure) and the first and second anchoring members 220a, 220b are both in the anchoring state, the first and second anchoring members 220a, 220b are configured in such a way as to possess sufficient rigidity so as to not collapse or deform towards the third anchoring member 230.

The Locking Member (e.g., Locking Member 240).

As illustrated in at least FIG. 1D, FIG. 1H, FIG. 7A, FIG. 7B, FIG. 7C, FIG. 8A, FIG. 8B, FIG. 8C, and FIG. 8D, an example embodiment of the main assembly 200 may include a locking member or mechanism (e.g., locking member 240 or locking mechanism 240). The locking member 240 may be configurable or configured to transition between a locking state and an unlocking state. When in the locking state, the locking member 240 is configurable or configured to secure, lock, join, restrict, or the like, movement of an element of the hysteroscopic system 100 (e.g., the uterine assembly 300 or the manipulator assembly 400) relative to the main assembly 200.

Figure 6A:
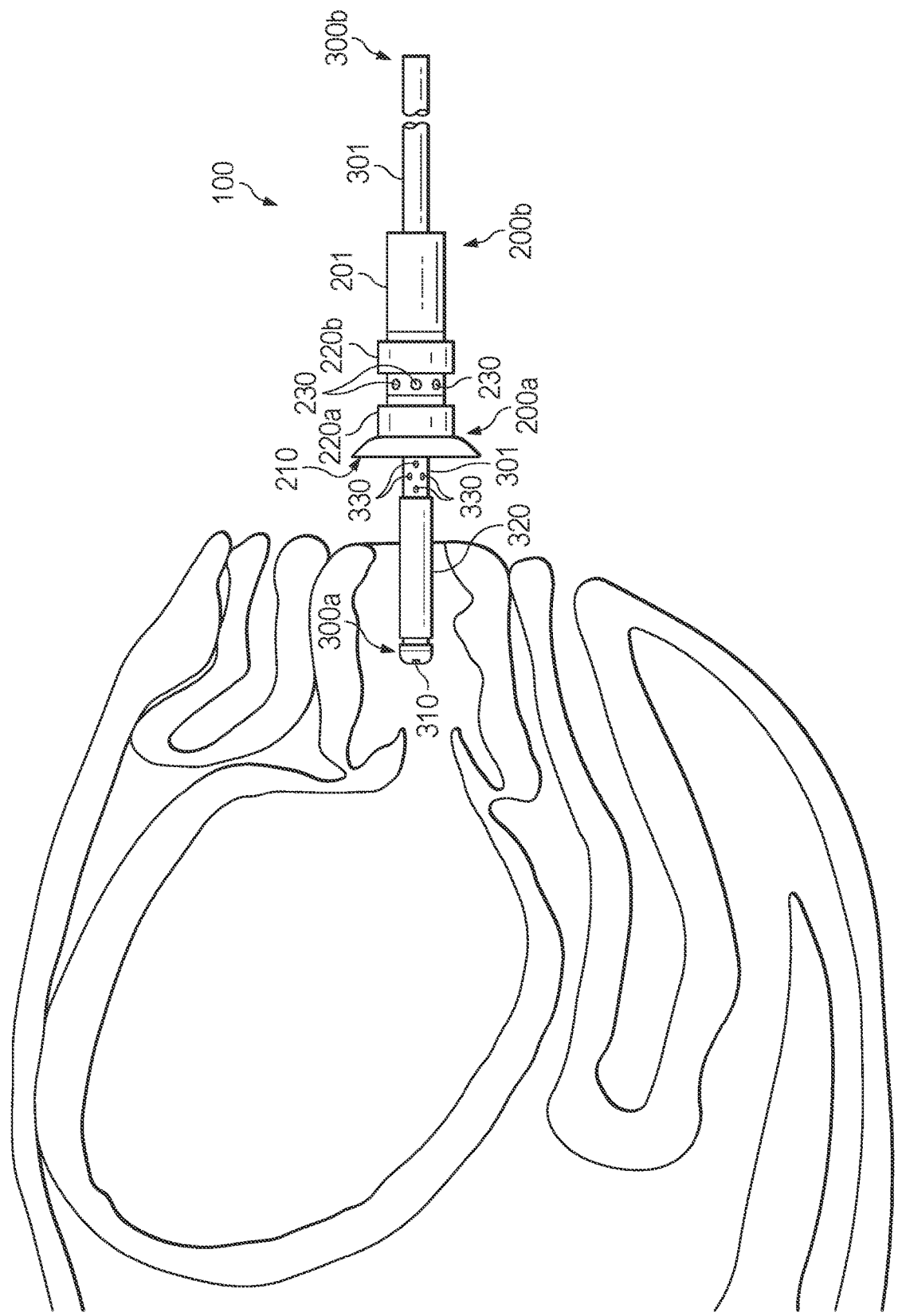
FIG. 6A is an illustration of an example embodiment of a hysteroscopic system being inserted into a vaginal cavity of a patient.
Figure 6B:
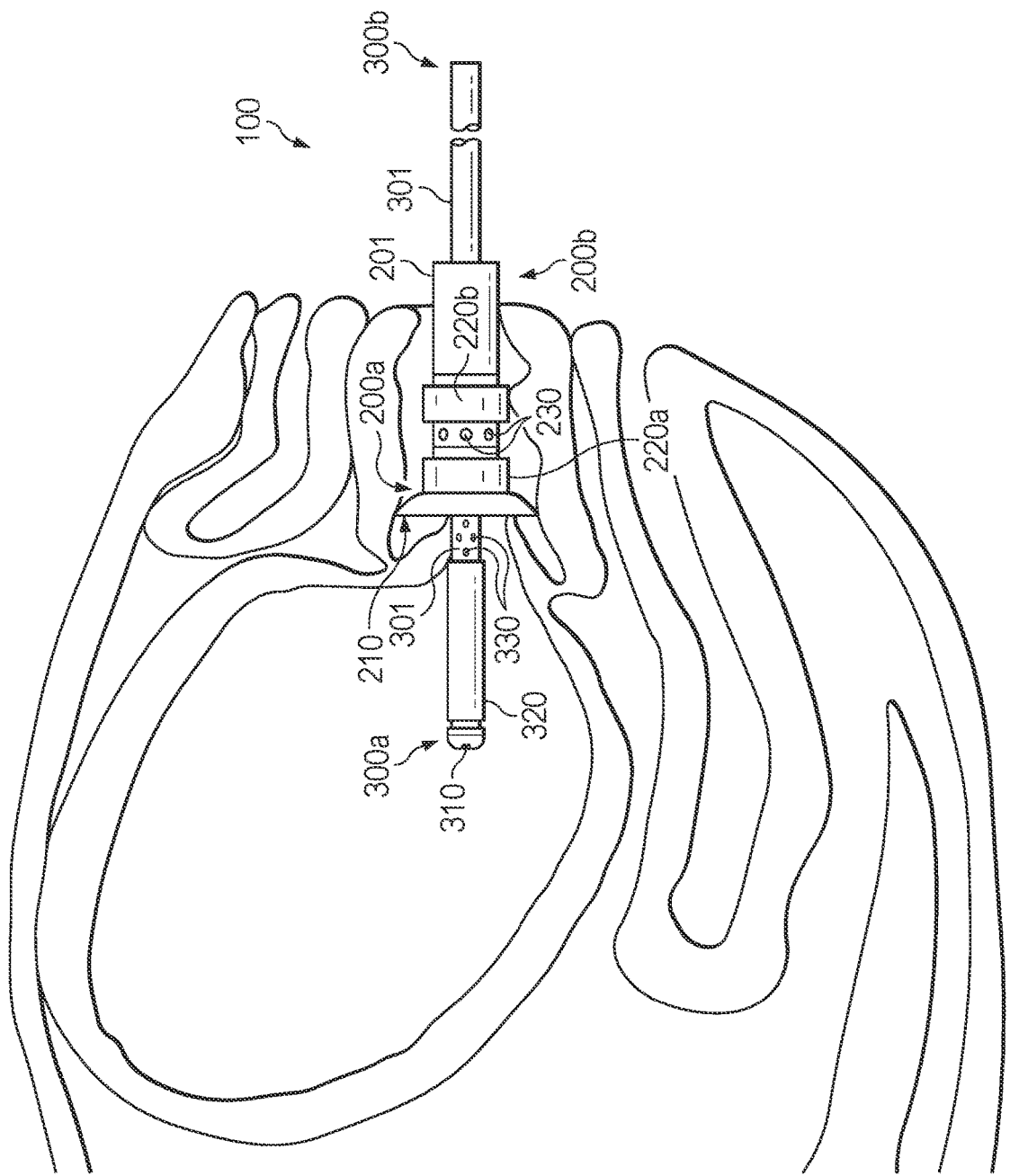
FIG. 6B is an illustration of an example embodiment of a hysteroscopic system having a main assembly (non-anchoring state) housed in a vaginal cavity of a patient and a uterine assembly (non-hemostasis state) housed in a uterine cavity of the patient.
Figure 6C:
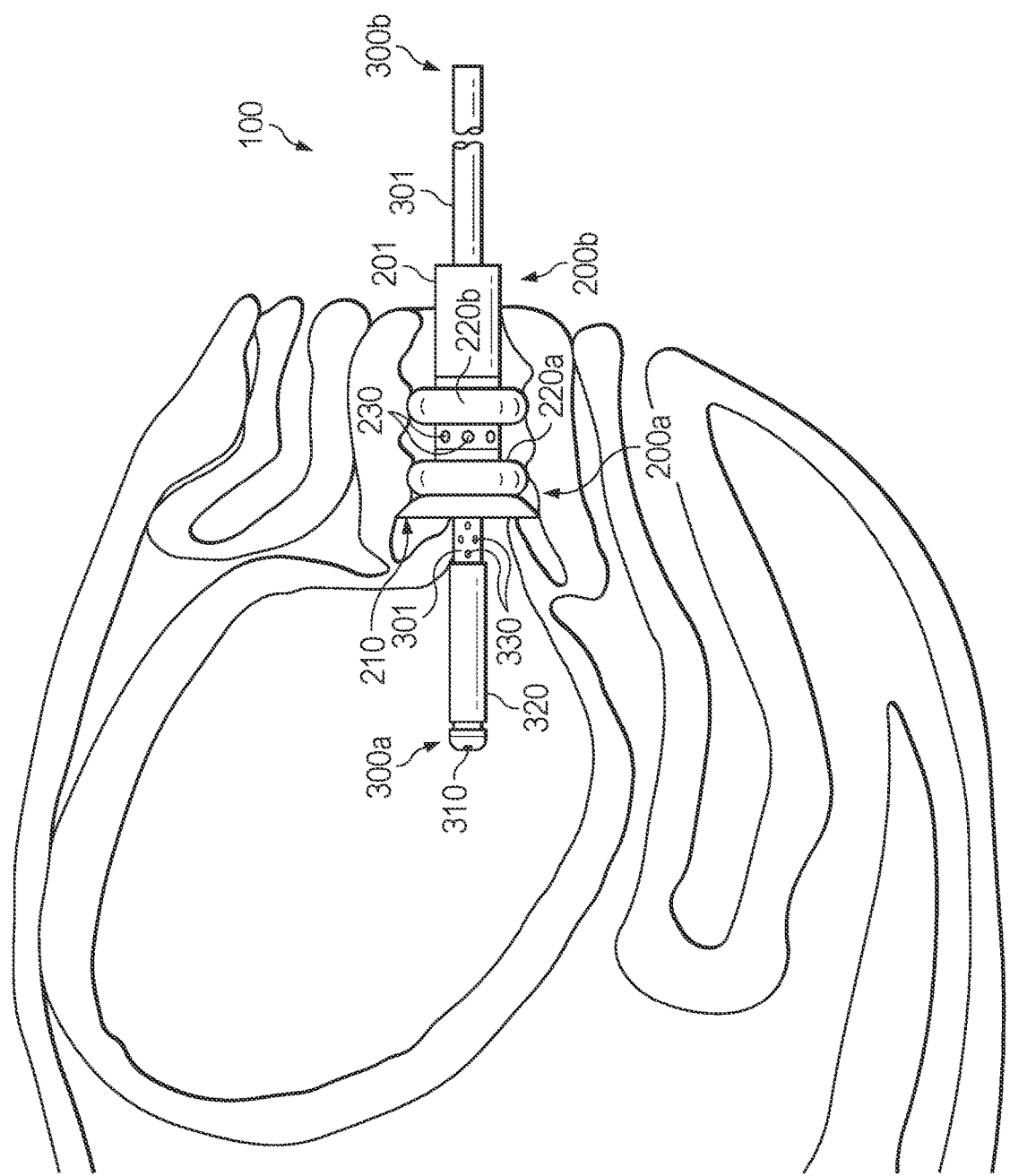
FIG. 6C is an illustration of an example embodiment of a hysteroscopic system having a main assembly (first and second anchoring members in the anchoring state) housed in a vaginal cavity of a patient and a uterine assembly (non-hemostasis state) housed in a uterine cavity of the patient.
Figure 6D:
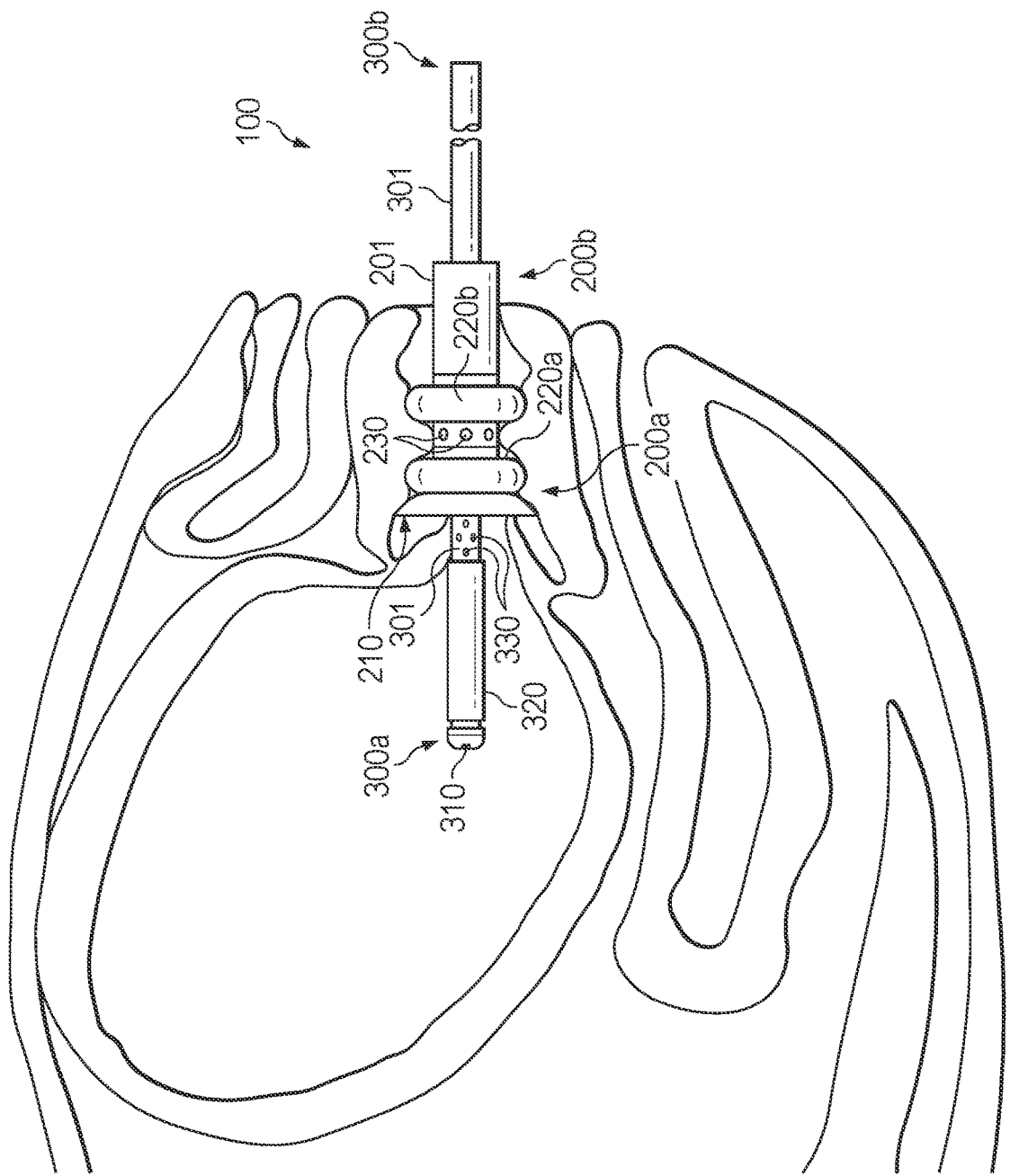
FIG. 6D is an illustration of an example embodiment of a hysteroscopic system having a main assembly (first, second, and third anchoring members in the anchoring state) anchored to a vaginal cavity of a patient and a uterine assembly (non-hemostasis state) housed in a uterine cavity of the patient.
Figure 6E:
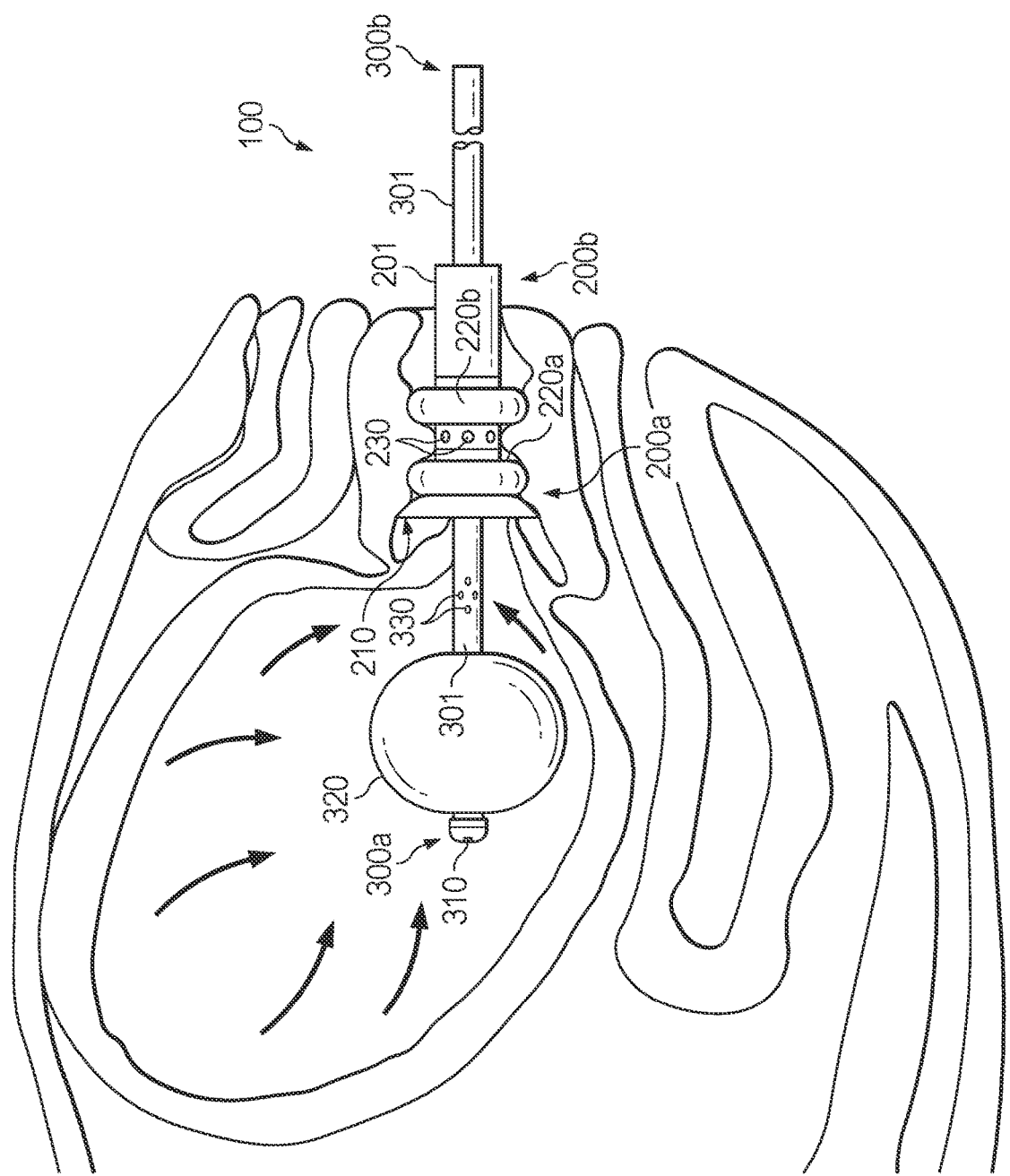
FIG. 6E is an illustration of an example embodiment of a hysteroscopic system having a main assembly (first, second, and third anchoring members in the anchoring state) anchored to a vaginal cavity of a patient and a uterine assembly (first negative pressure port, uterine expandable member, and second negative pressure port transitioned to the hemostasis state) housed in a uterine cavity of the patient.
Figure 6F:
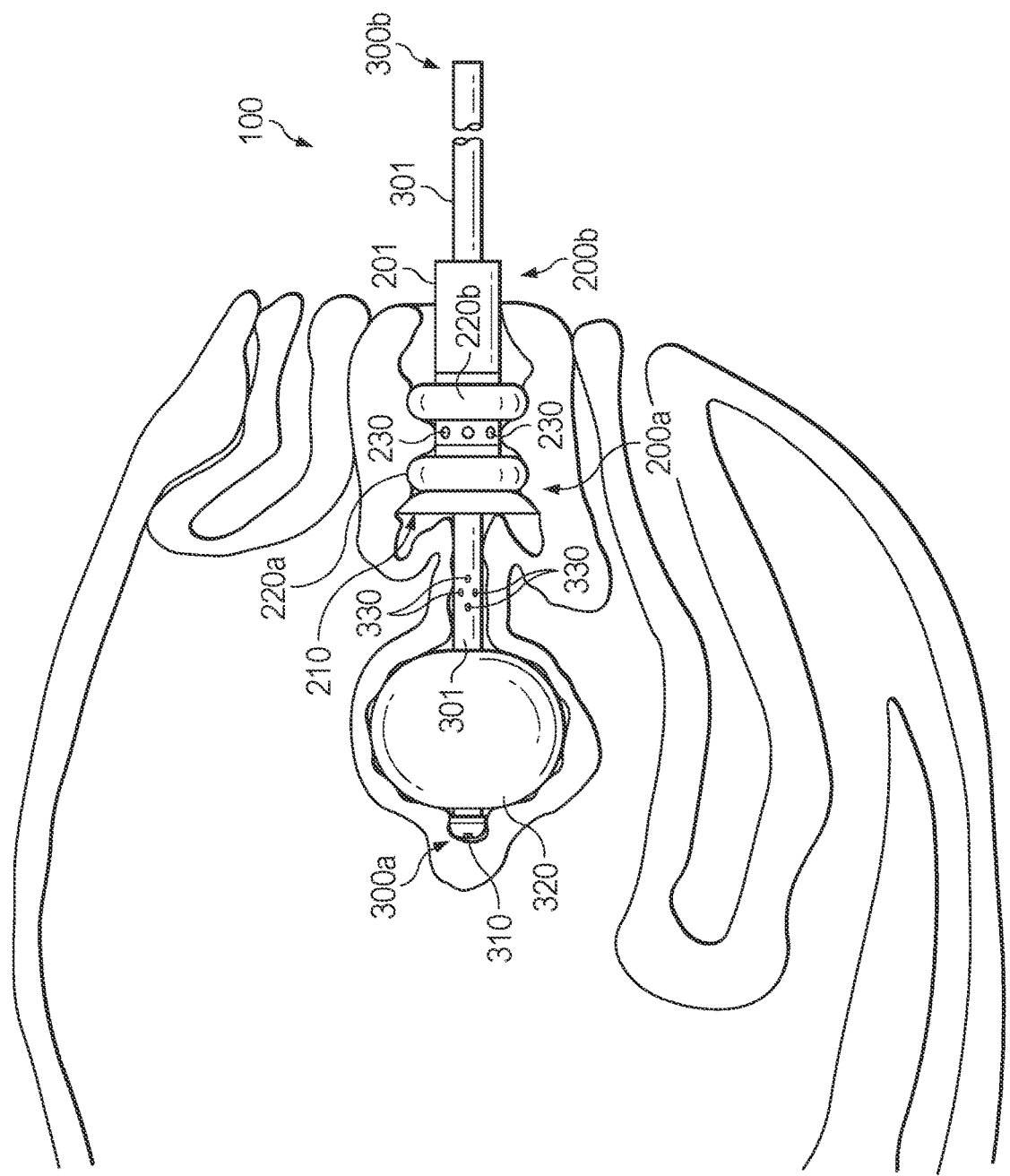
FIG. 6F is an illustration of an example embodiment of a hysteroscopic system having a main assembly (first, second, and third anchoring members in the anchoring state) anchored to a vaginal cavity of a patient and a uterine assembly (first negative pressure port, uterine expandable member, and second negative pressure port in the hemostasis state) anchored to a uterine cavity of the patient.

For example, when the uterine assembly 300 is provided through the main channel 202 of the main assembly 200 (e.g., as illustrated in at least FIGS. 6A, 6B, 6C, 6D and 7A) and transitioned to the hemostasis state (e.g., the first negative pressure port 310, uterine expandable member 320, and second negative pressure port 330 are transitioned from the non-hemostasis state to the hemostasis state when in the uterine cavity of the patient; as illustrated in at least FIGS. 6F and/or 6G), the locking member 240 may be transitioned from the unlocking state (e.g., as illustrated in at least FIGS. 7A, 7B, 8B, and 8D) to the locking state (e.g., as illustrated in at least FIGS. 7C, 8A, and 8C) so as to enable the uterine assembly 300 to be held in the homeostasis state (e.g., as illustrated in at least FIGS. 6F and/or 6G) for a prolonged period of time to manage (e.g., stop) the PPH for the patient.

As another example, when the manipulator assembly 400 is provided through the main channel 202 of the main assembly 200 (e.g., as illustrated in at least FIG. 6I), the locking member 240 may be transitioned from the unlocking state (e.g., as illustrated in at least FIGS. 7A, 7B, 8B, and 8D) to the locking state (e.g., as illustrated in at least FIGS. 7C, 8A, and 8C) so as to enable the manipulator assembly 400 to be held in position to perform a surgical action in the uterine cavity of the patient.

Figure 7A:
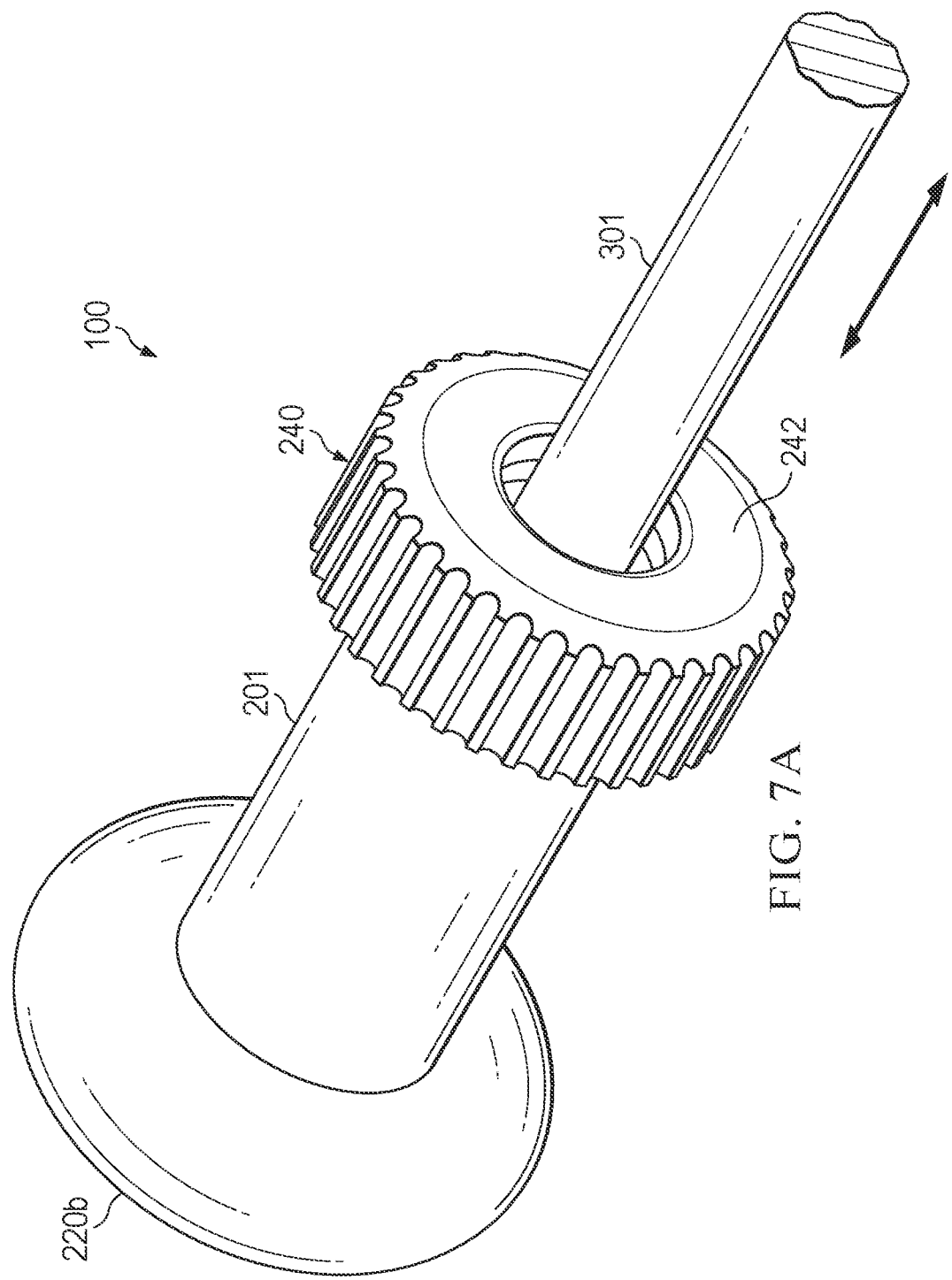
FIG. 7A is an illustration of a perspective view of an example embodiment of a locking mechanism.
Figure 7B:
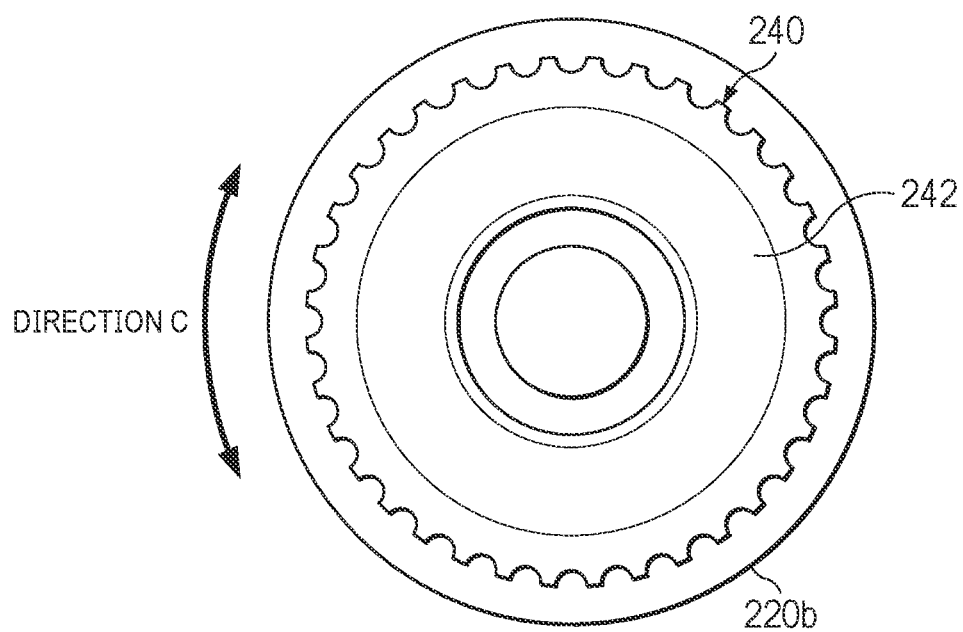
FIG. 7B is an illustration of a front view of an example embodiment of a locking mechanism configurable or configured to transition between locked and unlocked states based on a rotation direction of the locking mechanism.
Figure 7C:
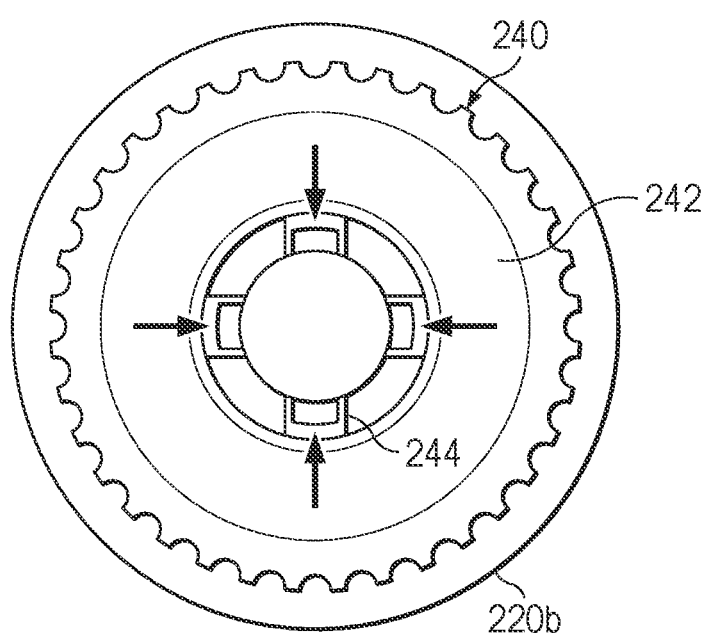
FIG. 7C is another illustration of front view of an example embodiment of locking mechanism in the locked state.

As illustrated in at least FIGS. 7A, 7B, 7C, 8A, 8B, 8C, and 8D, an example embodiment of the locking member 240 may include a main locking body 242. As illustrated in at least FIGS. 7B and 7C, the main locking body 242 may be rotatable in one or both of the directions C so as to transition between the unlocking state (e.g., as illustrated in FIG. 7B) and the locking state (e.g., as illustrated in FIG. 7C). When the main locking body 242 is rotated to the locking state, one or more lock elements 244 (e.g., as illustrated in FIG. 7C) are actuated to protrude inwardly so as to contact with and secure, lock, join, restrict, or the like, an element of the hysteroscopic system 100 (e.g., the uterine assembly 300 or the manipulator assembly 400) relative to the main assembly 200.

Figure 8A:
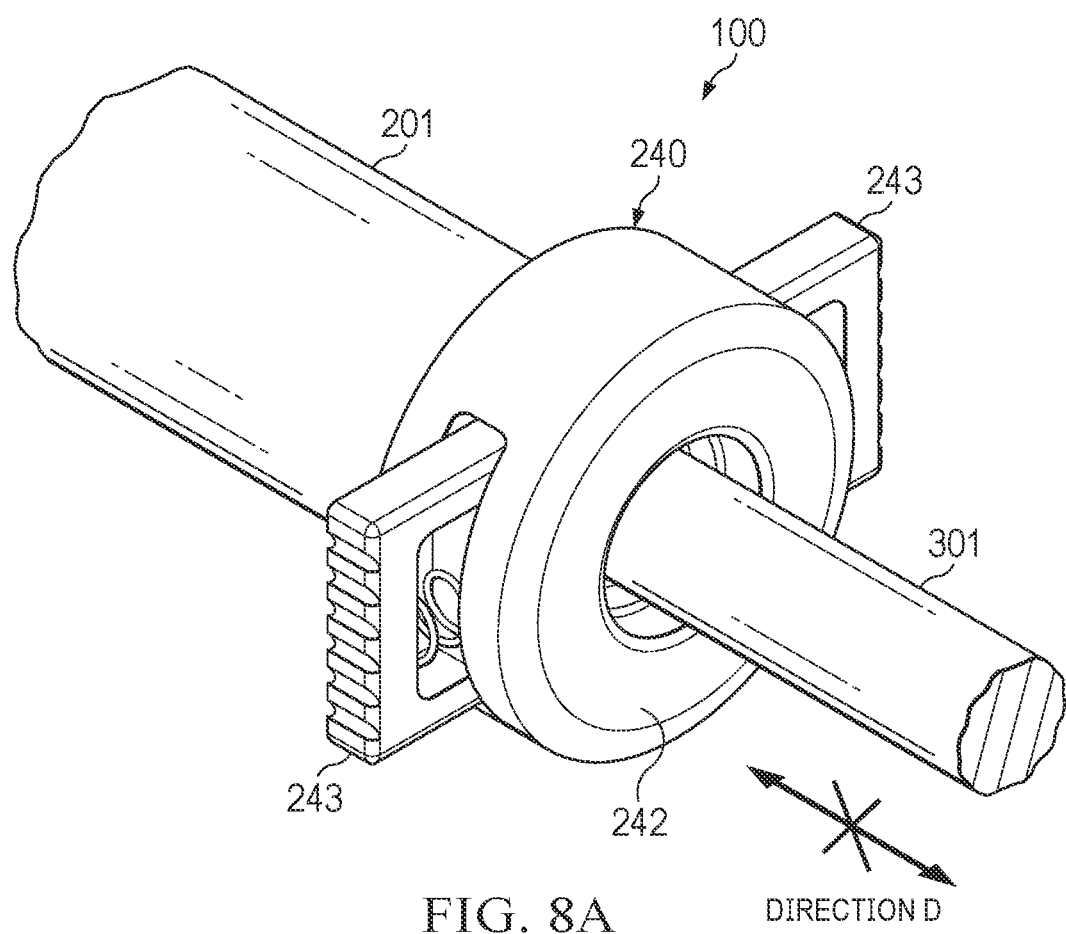
FIG. 8A is an illustration of a perspective view of an example embodiment of a locking mechanism in a locked state.
Figure 8B:
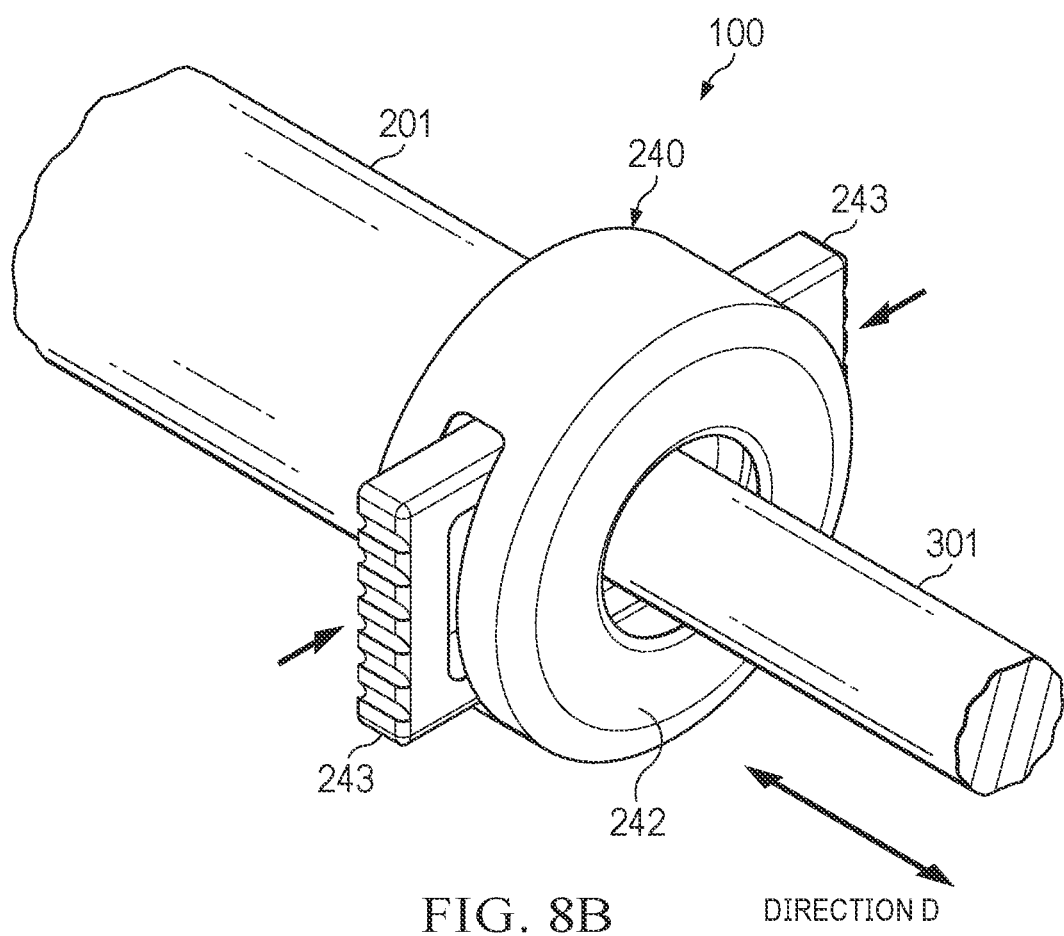
FIG. 8B is an illustration of a perspective view of an example embodiment of a locking mechanism in an unlocked state.
Figure 8C:
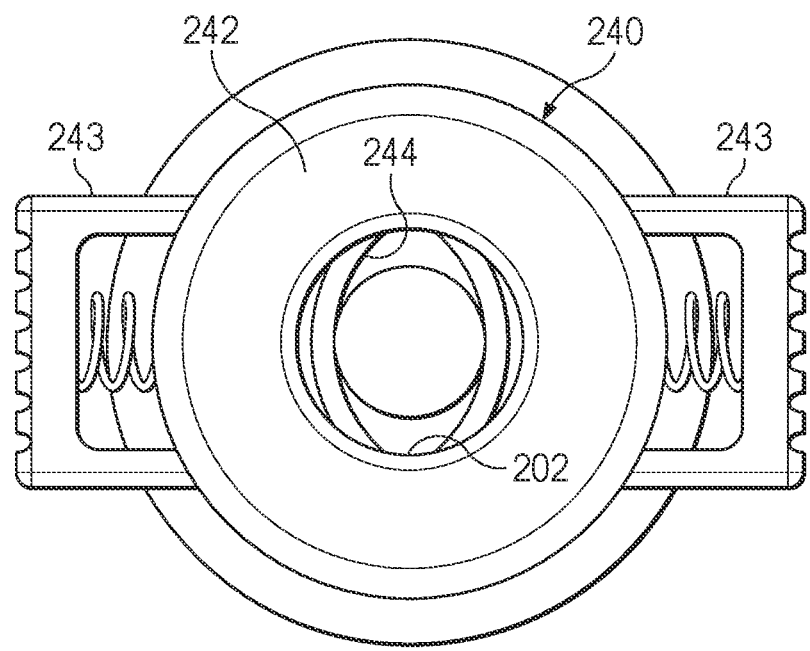
FIG. 8C is an illustration of a front view of an example embodiment of a locking mechanism in a locked state.
Figure 8D:
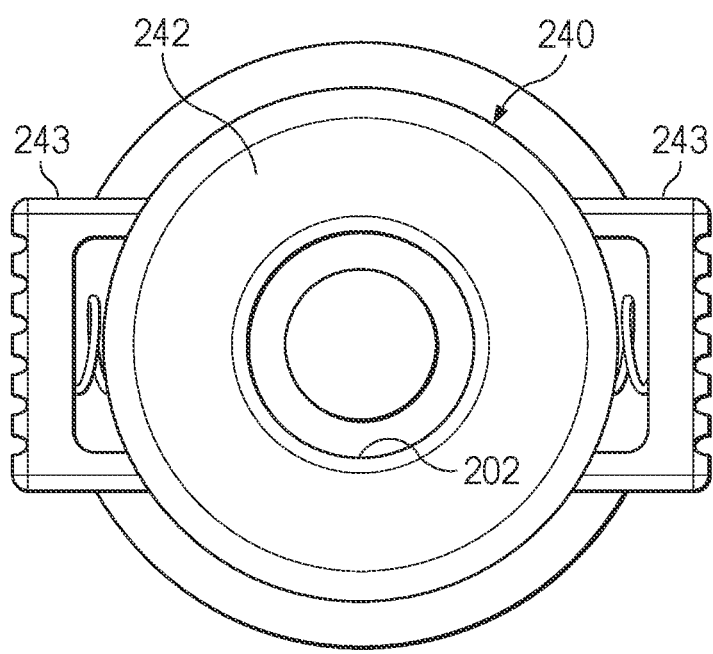
FIG. 8D is an illustration of a front view of an example embodiment of a locking mechanism in an unlocked state.

Alternatively or in addition, the locking member 240 may include a locking actuator 243 (e.g., as illustrated in at least FIGS. 8A, 8B, 8C, and 8D). When the locking actuator 243 is transitioned to the locking state (e.g., as illustrated in at least FIGS. 8B and 8D), one or more lock elements 244 (e.g., as illustrated in FIG. 8C) are actuated to contact with and secure, lock, join, restrict, or the like, an element of the hysteroscopic system 100 (e.g., the uterine assembly 300 or the manipulator assembly 400) relative to the main assembly 200.

It is to be understood in the present disclosure that the locking member 240 may be formed in any one or more other shapes, forms, configurations, mechanisms, assemblies, or the like, so long as it secures, locks, joins, restricts, or the like, an element of the hysteroscopic system 100 (e.g., the uterine assembly 300 or the manipulator assembly 400) relative to the main assembly 200.

The Vaginal Seal Member (e.g., Vaginal Seal Member 250).

As illustrated in at least FIG. 2C and FIG. 2D, the main assembly 200 includes one or more vaginal seal members (e.g., vaginal seal member 250). The vaginal seal member 250 may be configurable or configured to properly position the main assembly 200 in a vaginal cavity of the patient. Alternatively or in addition, the vaginal seal member 250 may be configurable or configured to separate, seal, isolate, and/or hermetically seal the vaginal cavity of the patient.

The vaginal seal member 250 may be formed at the in vitro end 200b of the main assembly 200. The vaginal seal member 250 may include a central axis that is coaxial to a central axis of the main assembly 200 (e.g., a central axis of the main channel 202). The vaginal seal member 250 may be formed along a plane that is orthogonal or substantially orthogonal to the main channel 202 (and/or a central axis formed through the main channel 202). The vaginal seal member 250 may include an outermost edge portion (or perimeter portion or rim portion) formed between the contact wall 251 and non-contact wall 252 of the vaginal seal member 250. Such outermost edge portion of the vaginal seal member 250 may be formed along a plane that is orthogonal or substantially orthogonal to the main channel 202 (and/or a central axis formed through the main channel 202).

To perform the actions, functions, processes, and/or methods described above and in the present disclosure, example embodiments of the vaginal seal member 250 include one or more elements and/or characteristics. For example, the vaginal seal member 250 includes one or more contact walls 251. In operation, when the main assembly 200 is inserted into the vaginal cavity of the patient, the contact wall 251 is configurable or configured to contact with at least a portion of a vulva (and/or surrounding areas around the vulva) of the patient. In example embodiments, the vaginal seal member 250 may also include one or more non-contact walls 252 (e.g., opposite to the contact wall 251). In some example embodiments, the vaginal seal member 250 may include one or more sealable members, or the like (not shown), which may be elements that are similar to or the same as the one or more seal members 216 of the cervical seal member 210 (as described in the present disclosure). In some example embodiments, the vaginal seal member 250 may also include one or more suction modules, or the like (not shown), which may be elements that are similar to or the same as the suction modules 218 of the cervical seal member 210 (as described in the present disclosure).

The Contact Wall of the Vaginal Seal Member (e.g., Contact Wall 251).

In an example embodiment, the vaginal seal member 250 includes one or more contact walls 251. The contact wall 251 of the vaginal seal member 250 may be configurable or configured to contact with at least a portion of the vulva (and/or surrounding areas around the vulva) of the patient. When contacting with at least a portion of the vulva (and/or surrounding areas around the vulva) of the patient, the contact wall 251 may separate, isolate, seal, and/or hermetically seal the vaginal cavity of the patient (e.g., in cooperation with the sealable member (not shown) of the vaginal seal member 250 and/or one or more other elements of the hysteroscopic system 100, such as the uterine assembly 300). The contact wall 251 of the vaginal seal member 250 may include a circular contact portion (and/or any other geometrical shape). The circular contact portion of the contact wall 251 may be formed along a plane that is substantially orthogonal to the first central axis formed through the main channel 202. The contact wall 251 of the vaginal seal member 250 may include at least a portion that is formed in a concave shape. Alternatively or in addition, the contact wall 251 of the vaginal seal member 250 may include at least a portion that is formed in a convex shape, curve shape, rounded shape, etc. The circular contact portion of the contact wall 251 of the vaginal seal member 250 may be formed along a plane that is orthogonal or substantially orthogonal to the main channel 202 (and/or first central axis formed through the main channel 202). The contact wall 251 and/or non-contact wall 252 of the vaginal seal member 250 may include one or more flexible portions (e.g., the outermost edge portion formed between the contact wall 251 and non-contact wall 252). The at least one flexible portion of the contact wall 251 and/or non-contact wall 252 of the vaginal seal member 250 is configured to dynamically adapt to a surface topology of the vulva (and/or surround portions) of the patient (and/or provide a seal and/or hermetic seal).

The Sealable Member of the Vaginal Seal Member (not Shown).

In an example embodiment, the vaginal seal member 250 may also include one or more sealable members (not shown), which may be one or more elements that are similar to, the same as, and/or function similar to and/or the same as the one or more seal members 216 of the cervical seal member 210 (as described in the present disclosure). The sealable member of the vaginal seal member 250 may be configurable or configured to dynamically adjust or transition between an opening state (e.g., a state in which one or more elements of the hysteroscopic system 100 are provided through the sealable member of the vaginal seal member 250) and a closed state (e.g., a state in which no elements of the hysteroscopic system 100 are provided through the sealable member of the vaginal seal member 250).

For example, when a uterine assembly 300 is provided through the sealable member of the vaginal seal member 250 (opening state), the seal member of the vaginal seal member 250 is configurable or configured to provide a hermetic seal around the uterine assembly 300 (or the portion of the uterine assembly 300 provided through the sealable member of the vaginal seal member 250). The sealable member of the vaginal seal member 250 may be configurable or configured to allow the uterine assembly 300 to slide or pass through in both directions (opening state). As another example, when a manipulator assembly 400 is provided through the sealable member of the vaginal seal member 250 (opening state), the sealable member of the vaginal seal member 250 is configurable or configured to provide a hermetic seal around the manipulator assembly 400 (or the portion of the manipulator assembly 400 provided through the sealable member of the vaginal seal member 250). The sealable member of the vaginal seal member 250 may be configurable or configured to allow the manipulator assembly 400 to slide or pass through in both directions. The sealable member of the vaginal seal member 250 may be configurable or configured to hermetically seal itself when the manipulator assembly 400 is not provided through the sealable member of the vaginal seal member 250 (closed state). The sealable member of the vaginal seal member 250 may be formed coaxial to the vaginal seal member 250 (and/or a central axis formed through the vaginal seal member 250). Alternatively or in addition, the sealable member of the vaginal seal member 250 may be formed coaxial to the main channel 202 (and/or a central axis formed through the main channel 202).

The Suction Modules of the Vaginal Seal Member (not Shown).

In an example embodiment, the vaginal seal member 250 may also include one or more suction modules (not shown). The one or more suction modules of the vaginal seal member 250 may be formed on the contact wall 251 of the vaginal seal member 250. The one or more suction modules of the vaginal seal member 250 may be configurable or configured to provide a negative pressure. When in operation, such negative pressure may enable or facilitate a seal and/or hermetic seal between the vaginal seal member 250 and a vulva of the patient (and/or surrounding area of the vulva of the patient).

In another example embodiment, the vaginal seal member 250 may be adjustable in one or more directions and/or orientation so as to contact with the vulva of the patient (and/or surrounding areas of the vulva of the patient). A dimension and/or size of the vaginal seal member 250 may be greater than an overall size of the vulva of the patient so as to seal the vulva (and/or surrounding areas) of the patient. For example, the vaginal seal member 250 may have a diameter of between 50 to 120 mm, or more or less. In some embodiments, the vaginal seal member 250 may have a diameter of between 60 to 80 mm. In some embodiments, the vaginal seal member 250 may have an outside diameter of about 70 mm.

In example embodiments, the vaginal seal member 250 may be formed partially or completely of medical grade rubber, starch, silicone, polymer or copolymer including polyvinyl chloride (PVC), polypropylene (PP), polyethylene (PE), polystyrene (PS), polymethacrylate (PMMA), polyacrylonitrile, or combination thereof. The vaginal seal member 250 may be formed with sufficient rigidity so as to maintain its original shape, while also having sufficient flexibility so as to enable the vaginal seal member 250 to provide a seal and/or hermetic seal around the vulva of the patient when in operation. The vaginal seal member 250 may include elastic and flexible properties so that, when in use, the vaginal seal member 250 may conform and/or adjusted to fit an exterior of the patient's body without causing injuries.

The First Extendible Member (e.g., First Extendible Member 260).

Figure 3A:
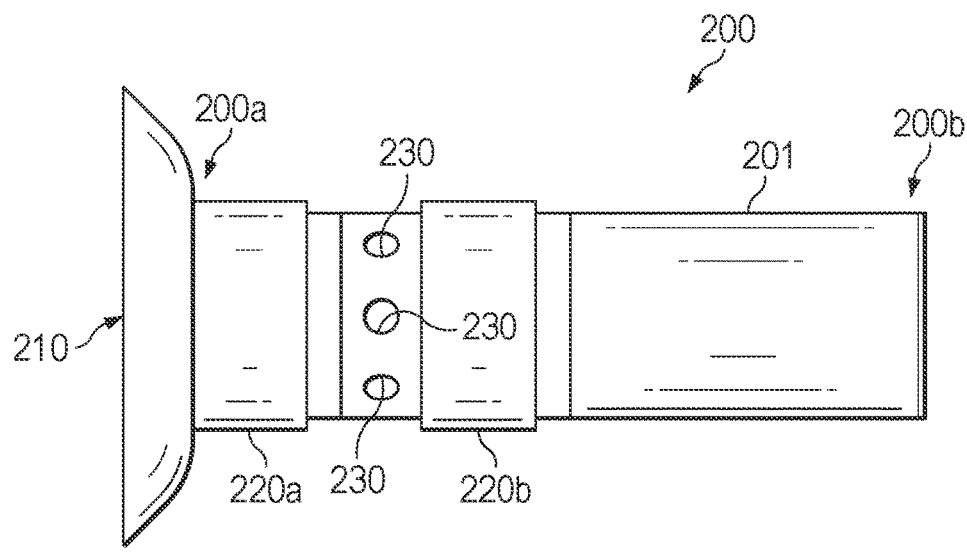
FIG. 3A is an illustration of a side view of an example embodiment of a main assembly (in non-anchoring state) of a hysteroscopic system for managing post-partum hemorrhaging.
Figure 3B:
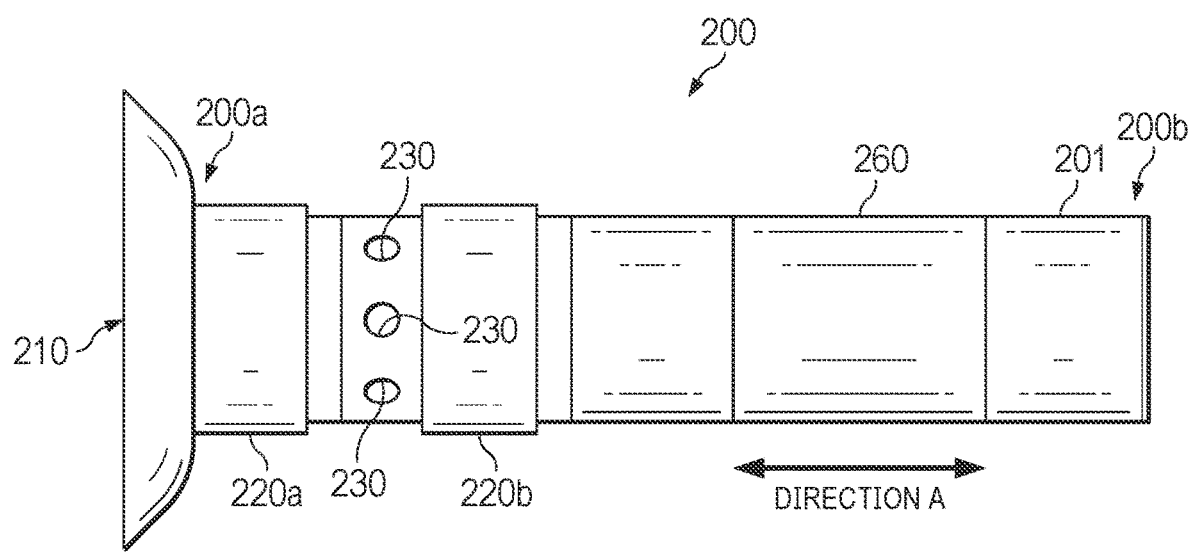
FIG. 3B is another illustration of a side view of an example embodiment of a main assembly (in non-anchoring state) of a hysteroscopic system for managing post-partum hemorrhaging.
Figure 3C:
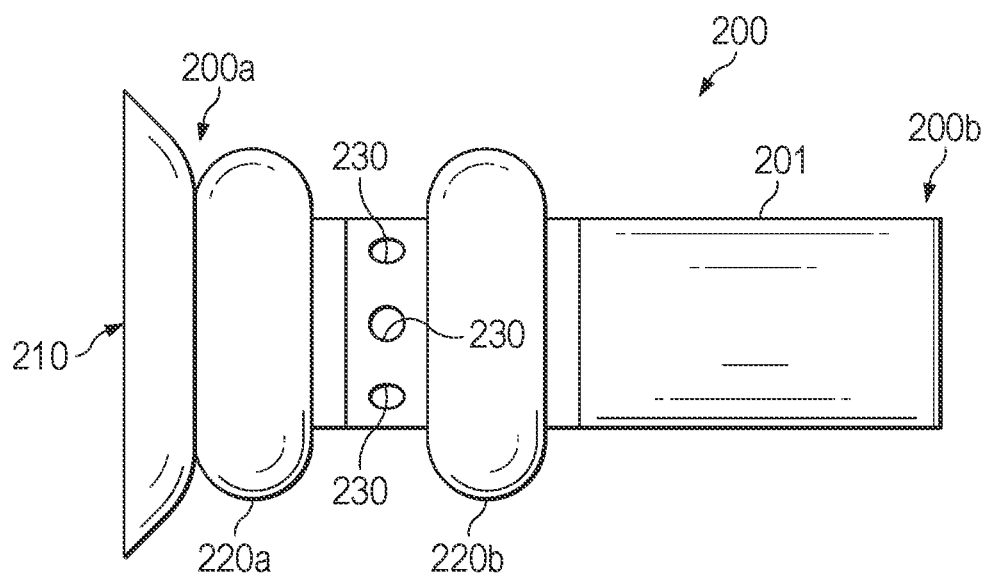
FIG. 3C is another illustration of a side view of an example embodiment of a main assembly (anchoring state) of a hysteroscopic system for managing post-partum hemorrhaging.
Figure 3D:
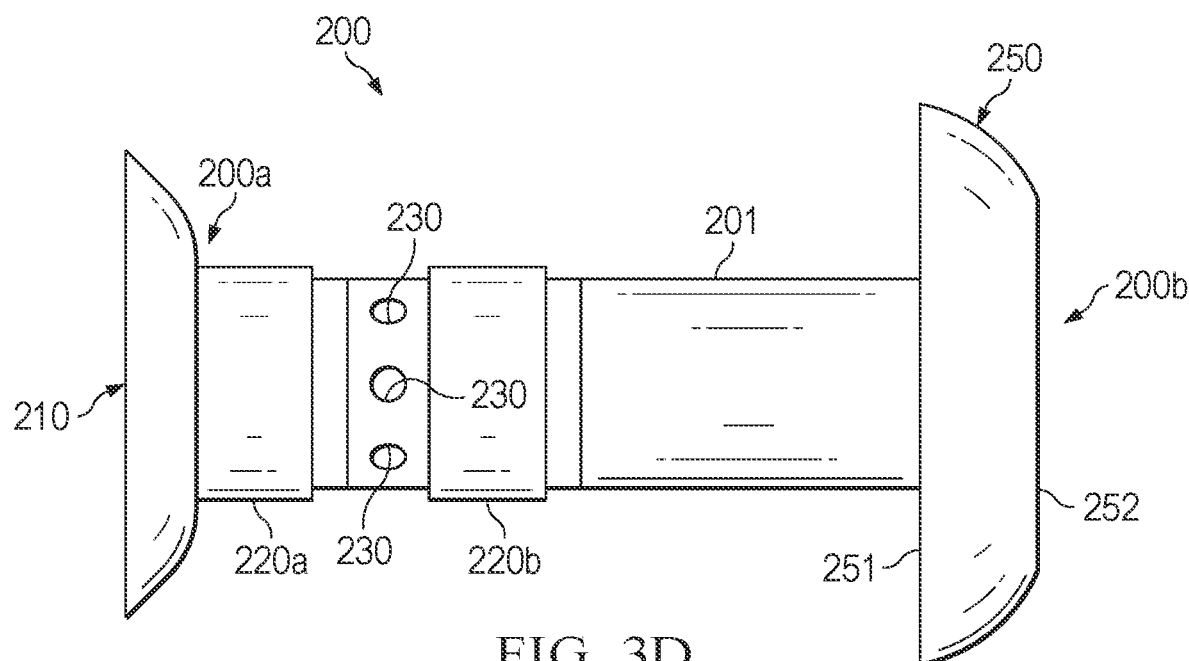
FIG. 3D is another illustration of a side view of an example embodiment of a main assembly (non-anchoring state) of a hysteroscopic system for managing post-partum hemorrhaging.

As illustrated in at least FIG. 3B, the main assembly 200 may include one or more first extendible members (e.g., first extendible member 260). The first extendible member 260 may be configurable or configured to selectively adjust or change a length of the main assembly 200 (and/or a distance between the in vivo end 200a and the in vitro end 200b of the main assembly 200).

For example, the first extendible member 260 may be configurable or configured to extend or contract/shorten in Direction A (e.g., as illustrated in at least FIG. 3B) to adjust the overall length of the main assembly 200. The first extendible member 260 may be formed on, in, and/or as a part of the main assembly 200 (e.g. adjacent to the second anchoring member 220b and/or at any other location along the main assembly 200). When the main assembly 200 is introduced trans-vaginally, the first extendible member 260 may be adjusted such that each element of the main assembly 200 (e.g. the cervical seal member 210, the first anchoring member 220a, the second anchoring member 220b, the third anchoring member 230, and vaginal seal member 250, etc.) is in a patient-specific position. Alternatively or in addition, the first extendible member 260 may be adjusted to suit specific anatomy (e.g., vaginal cavity dimensions) of each patient.

In example embodiments, the first extendible member 260 may be formed in any shape, form, size, and/or dimension (e.g., tubular shaped member, cylindrical shaped member, hollow shaped member, square tube shaped member, etc.).

The Uterine Assembly (e.g., Uterine Assembly 300).

As illustrated in at least in FIGS. 1A-1H and 2A-2D, the hysteroscopic system 100 includes a uterine assembly (e.g., uterine assembly 300). The uterine assembly 300 may be configurable or configured to be inserted through (and/or slide through) the main channel 202 of the main assembly 200 from the in vitro end 200b of the main assembly 200 until the in vivo end 300a of the uterine assembly 300 passes through the main channel 202 of the main assembly 200 and into the uterine cavity of the patient. In doing so, the uterine assembly 300 may be inserted through the sealable member 216 of the cervical seal member 210. In example embodiments in which the vaginal seal member 250 includes a sealable member (not shown; as described in the present disclosure), the uterine assembly 300 may also be inserted through the sealable member of the vaginal seal member 250.

To perform the actions, functions, processes, and/or methods described above and in the present disclosure, the uterine assembly 300 may include one or more elements.

For example, the uterine assembly 300 includes and/or is formed as an elongated body 301 having an in vivo end 300a and an in vitro end 300b opposite to the in vivo end 300a. The elongated body 301 of the uterine assembly 300 may be formed in one or more of a variety of shapes, dimensions, configurations, etc. For example, the elongated body 301 of the uterine assembly 300 may be formed in the shape of a cylindrical tube, or the like, and/or with a circular, elliptical, oval, or other cross sectional shape. The elongated body 301 of the uterine assembly 300 may include and/or be formed having a central axis.

The uterine assembly 300 also includes one or more first negative pressure ports 310. The uterine assembly 300 also includes one or more uterine expandable members 320. The uterine assembly 300 also includes one or more second negative pressure ports 330. The uterine assembly 300 may also include one or more locking members or mechanisms (not shown), which may be used (either alone or in cooperation with locking member 240 of the main assembly 200; such locking member of the uterine assembly 300 being similar to that of locking member 240) to secure, lock, join, restrict, or the like, movement of the uterine assembly 300 relative to the main assembly 200. The uterine assembly 300 may also include one or more bendable members 370 (e.g., as illustrated in at least FIG. 5C). The uterine assembly 300 may also include one or more second extendible members 340 (as illustrated in at least FIG. 5D).

These and other elements of the uterine assembly 300 will now be further described with reference to the accompanying figures.

The Elongated Body of the Uterine Assembly (e.g., Elongated Body 301).

As illustrated in at least FIGS. 1A-1H, 2A-2D, and 5A-D, the uterine assembly 300 includes an elongated body of uterine assembly (e.g., elongated body 301). The elongated body 301 of the uterine assembly 300 may function as a core structure to provide structural rigidity for the uterine assembly 300, and to secure, lock, join, restrict, or the like, a position of the uterine assembly 300 relative to the main assembly 200a. The elongated body 301 of the uterine assembly 300 may be configurable or configured to support each element of the uterine assembly 300 (e.g., the first negative pressure port 310, the uterine expandable member 320, the second negative pressure port 330, the bendable member 370, the extendible member 340, etc.). The elongated body 301 of the uterine assembly 300 is formed having sufficient rigidity so as to not bend, collapse, or deform when in operation, including when the first negative pressure port 310 is in the hemostasis state; when the uterine expandable member 320 is in the hemostasis state; when the second negative pressure port 330 is in the hemostasis state; when the bendable member 370 is selectively configured to bend in one or more locations along the bendable member 370 and/or bend in one or more directions and/or angles; when the extendible member 340 is selectively configured to extend or contract in length; and/or when the uterine assembly 300 is secured, locked, joined, restricted, or the like, relative to the main assembly 200.

The elongated body 301 of the uterine assembly 220 may be formed as a tubular shaped member, cylindrical shaped member, hollow member, square tubular shaped member, etc.

The First Negative Pressure Port (e.g., First Negative Pressure Port 310).

As illustrated in at least FIGS. 1A-1H, 2A-2D, and 5A-D, the uterine assembly 300 includes one or more first negative pressure ports (e.g., first negative pressure port 310). The first negative pressure port 310 may be formed or provided on a distal-most end (or tip) of the in vivo end 300a of the elongated body 301 of the uterine assembly 300 (e.g., see FIGS. 1A-H and 2A-D). Alternatively or in addition, the first negative pressure port 310 may be formed or provided on a side of the in vivo end 300a of the elongated body 301 of the uterine assembly 300 (e.g., see FIGS. 1B and 1F). The first negative pressure port 310 may be configurable or configured to provide a negative pressure. As described in the present disclosure, when the uterine assembly 300 is housed in a uterine cavity of a patient, the first negative pressure port 310 is configurable or configured to provide a negative pressure towards at least a portion of the uterine cavity (or uterine wall forming the uterine cavity) in such a way as to collapse, contract, shrink, narrow, and/or condense at least a portion of the uterine cavity (and/or uterine wall forming the uterine cavity) towards the elongated body 301 of the uterine assembly 300. In some example embodiments, the first negative pressure port 310 may also be configurable or configured to provide positive pressure so as to bring the uterine cavity (or uterine wall forming the uterine cavity) back to its normal (or near-normal) shape when needed (e.g., after completing a surgical action, such as treating PPH).

In an example embodiment, the first negative pressure port 310 may be configurable or configured to transition between a hemostasis state (or anchoring state) and a non-hemostasis state (or non-anchoring state). The hemostasis state of the first negative pressure port 310 is a state in which the first negative pressure port 310 applies at least a second negative pressure. The second negative pressure is an amount of negative pressure required to collapse at least a portion of the uterine cavity (or uterine wall forming the uterine cavity) towards the elongated body 301 of the uterine assembly 300. The non-hemostasis state of the first negative pressure port 310 is a state in which the first negative pressure port 310 does not apply at least the second negative pressure (e.g., the first negative pressure port 310 does not apply any negative pressure).

In an example embodiment, the elongated body 301 of the uterine assembly 300 is formed having sufficient rigidity so as to not bend, collapse, or deform when the first negative pressure port 310 applies negative pressure (or applies suction). Alternatively or in addition, when the first negative pressure port 310 applies negative pressure (e.g., the second negative pressure) and the uterine expandable member 320 and second negative pressure port 330 are both in the hemostasis state, the uterine expandable member 320 is configured in such a way as to possess sufficient rigidity so as to not collapse or deform.

The first negative pressure port 310 may be configurable or configured to provide negative pressure via a negative pressure source (not shown). The first negative pressure port 310 may also be configurable or configured to decrease a volume of the uterine cavity or cervix of the patient by providing a vacuum aspiration by any mechanically suitable methods. The first negative pressure port 310 may be in a form of a port, opening, groove, hole, aperture, orifice, slot, vent, or the like so as to allow the negative pressure to be introduced to the uterine cavity or cervix of the patient.

The Uterine Expandable Member (e.g., Uterine Expandable Member 320).

As illustrated in at least FIGS. 1A-H, 2A-D, and 5A-D, the uterine assembly 300 includes one or more uterine expandable members (e.g., uterine expandable member 320). The uterine expandable member 320 may be formed on (and/or attached to, formed with, etc.) the elongated body 301 of the uterine assembly 300. The uterine expandable member 320 may be configurable or configured to expand or protrude outwardly away from the elongated body 301 of the uterine assembly 300. For example, the uterine expandable member 320 may be an expandable and/or inflatable member configurable or configured to expand when a positive pressure, gas, liquid, and/or solid is introduced in the uterine expandable member 320 (e.g., from an external source (not shown)). The uterine expandable member 320 may be formed adjacent to the first negative pressure port 310. In example embodiments, the uterine expandable member 320 may be formed between the first negative pressure port 310 and the second negative pressure port 330. The uterine expandable member 320 may be configurable or configured to transition between a hemostasis state (or anchoring state) and a non-hemostasis state (or non-anchoring state). In an example embodiment, a default state (or initial state or normal state before performing hemostasis in the uterine cavity) of the uterine expandable member 320 is the non-hemostasis state.

When transitioning the uterine expandable member 320 from a non-hemostasis state to the hemostasis state, the uterine expandable member 320 may receive a positive pressure (or gas, liquid, and/or solid) so as to expand to a third overall volume (e.g., expanded outwardly away from the elongated body 301 of the uterine assembly 300 towards the wall of the uterine cavity).

When transitioning the uterine expandable member 320 from the hemostasis state to the non-hemostasis state, the uterine expandable member 320 may receive a negative pressure (or not receive a positive pressure, gas, liquid, and/or solid; and/or remove positive pressure, gas, liquid, and/or solid) so as to contract and/or reduce to a fourth overall volume (e.g., not expanded as outwardly away from the elongated body 301 of the uterine assembly 300 as compared to the hemostasis state). In this regard, the fourth overall volume is less than the third overall volume.

In another embodiment, a volume, shape, and/or size of the uterine expandable member 320 can be selectively adjustable in one or more directions. The uterine expandable member 320 may be in the form of an inflatable or expandable object that can be expanded or inflated with and/or receive and retain a gas, gaseous mixture, pressure, air, water, oil, liquid, semi-solid, etc. In some example embodiments, the uterine expandable member 320 may be in the form of an inflatable balloon member, expandable member, or the like. The uterine expandable member 320 may be made of surgical grade materials (e.g., surgical grade polyurethane, silicone, polycaprolactone, or the like).

The Second Negative Pressure Port (e.g., Second Negative Pressure Port 330).

As illustrated in at least FIGS. 1B, 1F, 2A-D, and 5A-D, the uterine assembly 300 includes one or more second negative pressure ports (e.g., second negative pressure port 330). The second negative pressure port 330 may be formed or provided on the elongated body 301 of the uterine assembly 300. For example, the second negative pressure port 330 may be formed or provided on the elongated body 301 of the uterine assembly 300 in such a way that the uterine expandable member 320 is provided between the first negative pressure port 310 and the second negative pressure port 330. The second negative pressure port 330 may be configurable or configured to provide a negative pressure. As described in the present disclosure, when the uterine assembly 300 is housed in a uterine cavity of a patient, the second negative pressure port 330 is configurable or configured to provide a negative pressure towards at least a portion of the uterine cavity (or uterine wall forming the uterine cavity) in such a way as to collapse, contract, shrink, narrow, and/or condense at least a portion of the uterine cavity (and/or uterine wall forming the uterine cavity) towards the elongated body 301 of the uterine assembly 300. In some example embodiments, the second negative pressure port 330 may also be configurable or configured to provide positive pressure so as to bring the uterine cavity (or uterine wall forming the uterine cavity) back to its normal (or near-normal) shape when needed (e.g., after completing a surgical action, such as treating PPH).

In an example embodiment, the second negative pressure port 330 may be configurable or configured to transition between a hemostasis state (or anchoring state) and a non-hemostasis state (or non-anchoring state). The hemostasis state of the second negative pressure port 330 is a state in which the second negative pressure port 330 applies at least a third negative pressure. The third negative pressure is an amount of negative pressure required to collapse at least a portion of the uterine cavity (or uterine wall forming the uterine cavity) towards the elongated body 301 of the uterine assembly 300. The non-hemostasis state of the second negative pressure port 330 is a state in which the second negative pressure port 330 does not apply at least the third negative pressure (e.g., the second negative pressure port 330 does not apply any negative pressure).

In example embodiments, the first negative pressure port 310 and second negative pressure port 330 are configurable or configured to cooperate to provide a sufficient collective negative pressure (e.g., the second negative pressure plus the third negative pressure) to collapse, contract, shrink, narrow, and/or condense most or all of the uterine cavity (and/or uterine wall forming the uterine cavity) towards the uterine expandable member 320 (when in the hemostasis state).

In an example embodiment, the elongated body 301 of the uterine assembly 300 is formed having sufficient rigidity so as to not bend, collapse, or deform when the second negative pressure port 330 applies negative pressure (or applies suction). Alternatively or in addition, when the second negative pressure port 330 applies negative pressure (e.g., the third negative pressure) and the uterine expandable member 320 and first negative pressure port 310 are both in the hemostasis state, the uterine expandable member 320 is configured in such a way as to possess sufficient rigidity so as to not collapse or deform.

The second negative pressure port 330 may be configurable or configured to provide negative pressure via a negative pressure source (not shown). The second negative pressure port 330 may also be configurable or configured to decrease a volume of the uterine cavity or cervix of the patient by providing a vacuum aspiration by any mechanically suitable methods. The second negative pressure port 330 may be in a form of a port, opening, groove, hole, aperture, orifice, slot, vent, or the like so as to allow the negative pressure to be introduced to the uterine cavity or cervix of the patient.

The Bendable Member (e.g., Bendable Member 370).

Figure 5A:
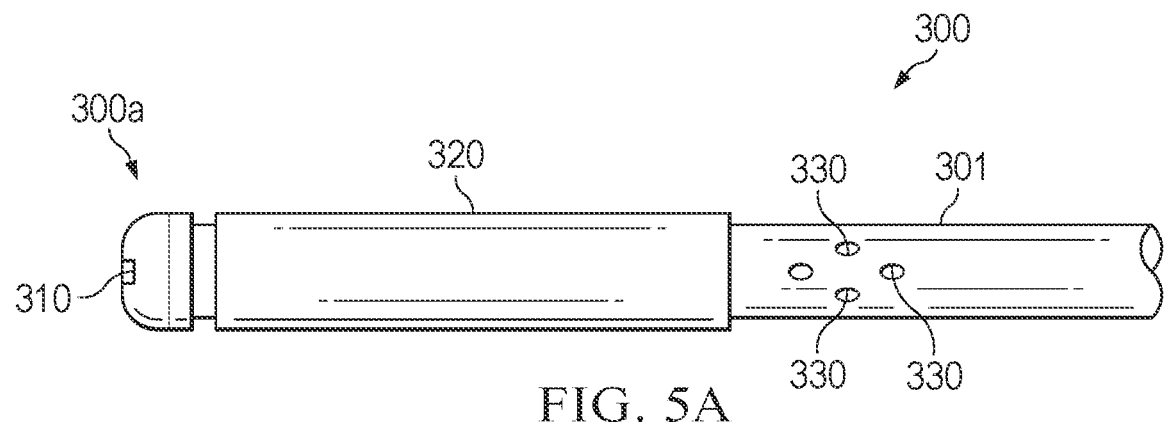
FIG. 5A is an illustration of a side view of an example embodiment of a uterine assembly (non-haemostasis state)
Figure 5B:
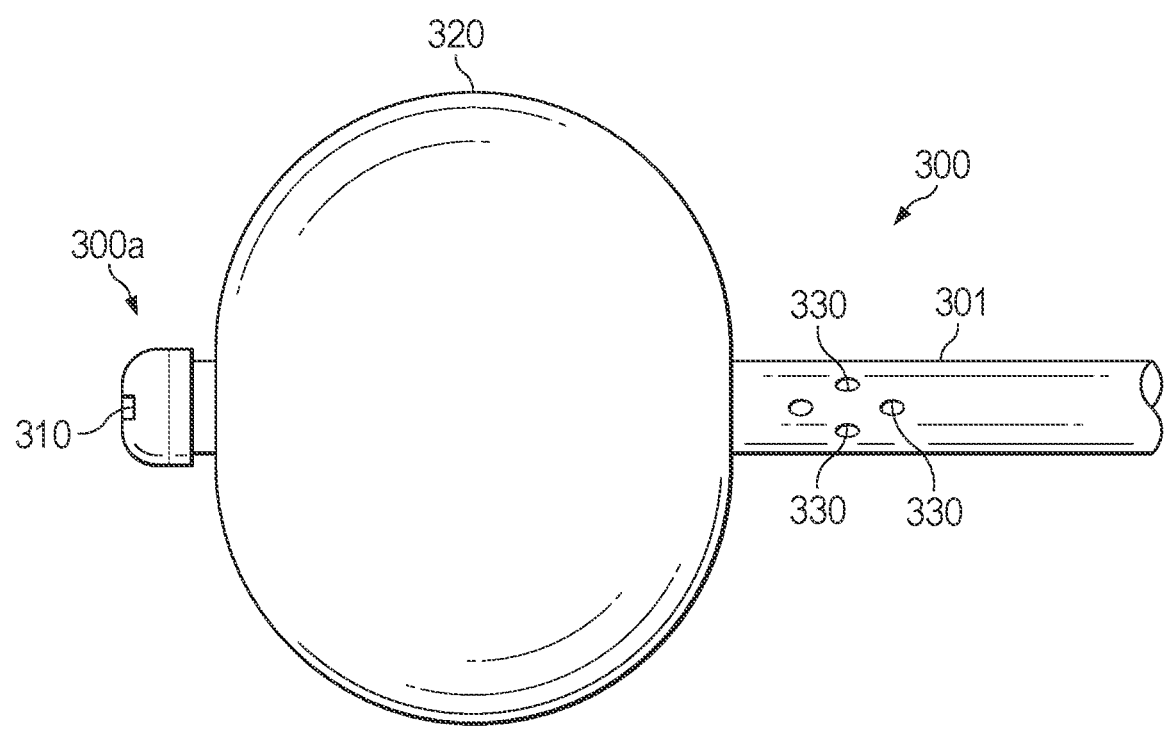
FIG. 5B is an illustration of a side view of an example embodiment of a uterine assembly (hemostasis state)
Figure 5C:
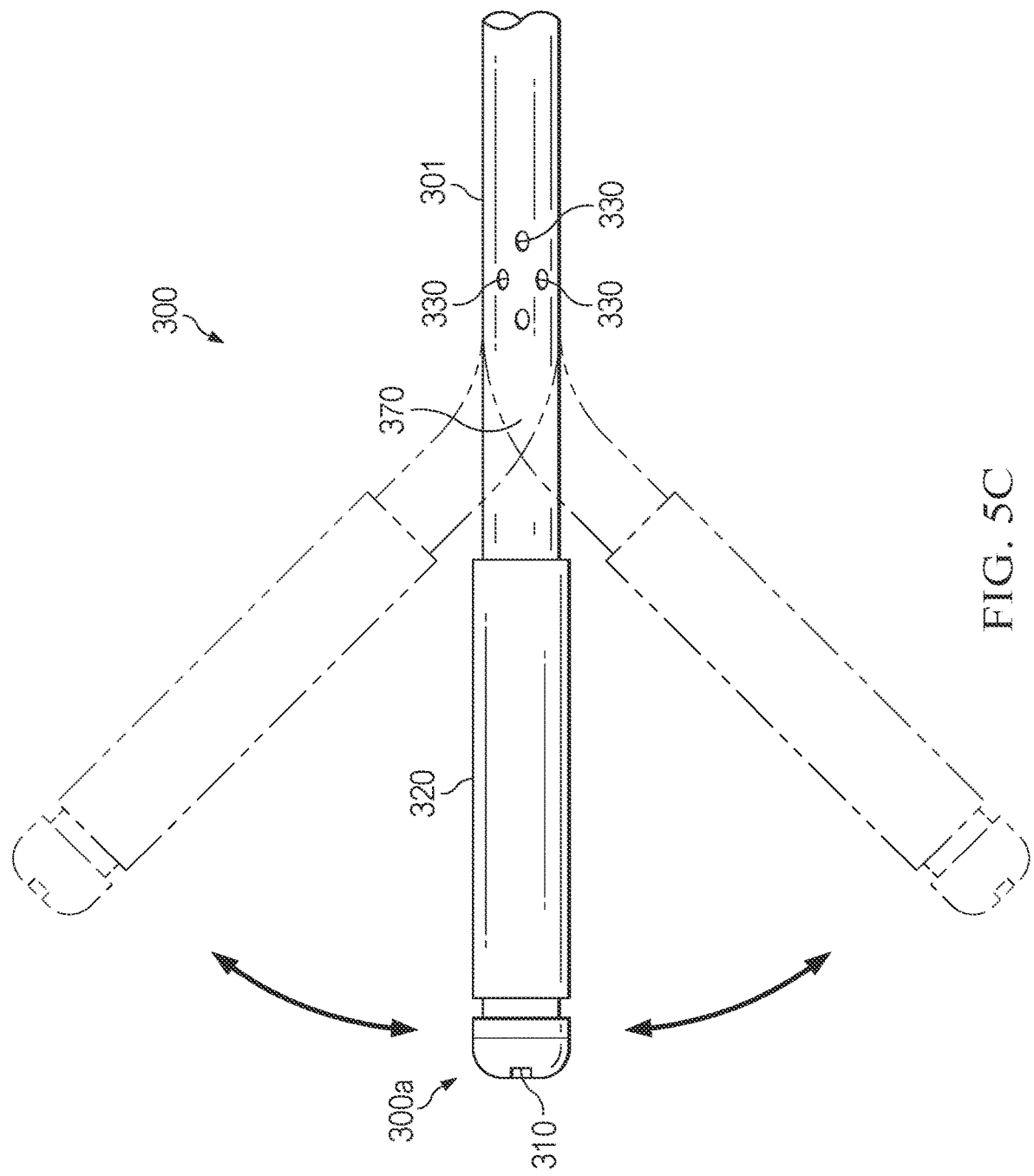
FIG. 5C is an illustration of a side view of an example embodiment of a uterine assembly having a bendable member.

As illustrated in at least FIG. 5C, the uterine assembly 300 includes one or more bendable members (e.g., bendable member 370). The bendable member 370 may be configurable or configured to facilitate a bending of the in vivo end 300a of the uterine assembly 300 at one or more locations and in one or more directions. The bendable member 370 may be selectively adjusted to bend in multiple angles, directions, and locations along the bendable member 370 so as to adjustably direct as needed the vivo end 300a of the uterine assembly 300 relative to the patient's uterine cavity.

In example embodiments, the bendable member 370 may be formed adjacent to the second negative pressure port 330 (e.g., between the second negative pressure port 330 and the in vitro end 300b of the uterine assembly 300). Alternatively or in addition, the bendable member 370 may be formed between the uterine expandable member 320 and the second negative pressure port 330. Alternatively or in addition, the bendable member 370 may be formed between the first negative pressure port 310 and the uterine expandable member 320. In example embodiments, the bendable member 370 may be configurable or configured to connect the in vivo end 300a of the uterine assembly 300 to the elongated body 301 (and/or in vitro end 300b) of uterine assembly 300.

In example embodiments, the bendable member 370 may be formed using any medical grade flexible, elastic, plastic, rigid, deformable, etc. material so long as the bendable member 370 can be selectively adjusted to bend in one or more bending angles, directions, and/or locations while rigid enough to maintain the vivo end 300a of the uterine assembly 300 in a desired direction, position, orientation, and/or location.

The Second Extendible Member (e.g., Second Extendible Member 340).

Figure 5D:
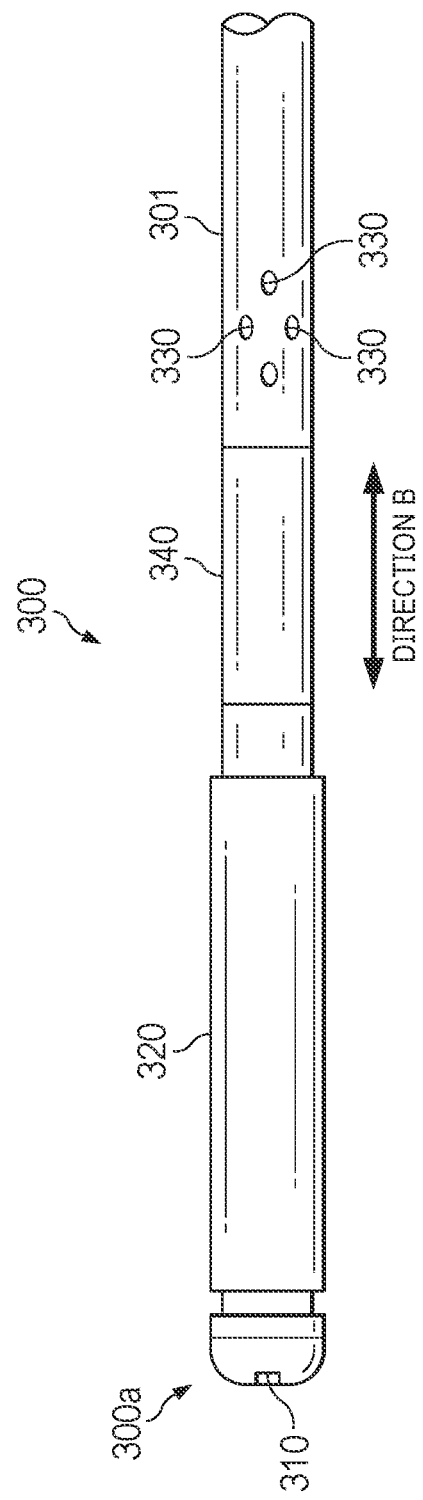
FIG. 5D is an illustration of a side view of an example embodiment of a uterine assembly having a second extendible member.

As illustrated in at least FIG. 5D, the uterine assembly 300 may include one or more second extendible members (e.g., second extendible member 340). The second extendible member 340 may be configurable or configured to selectively adjust or change a length of the uterine assembly 300 (and/or a distance between the in vivo end 300a and the in vitro end 300b of the uterine assembly 300).

For example, the second extendible member 340 may be configurable or configured to extend or contract/shorten in Direction B (e.g., as illustrated in at least FIG. 5D) to adjust the overall length of the uterine assembly 300. The second extendible member 340 may be formed on, in, and/or as a part of the uterine assembly 300 (e.g. adjacent to the uterine expandable member 320, between the uterine expandable member 320 and the second negative pressure port 330, and/or at any other location along the uterine assembly 300). When the uterine assembly 300 is inserted into the uterine cavity of the patient, the second extendible member 340 may be adjusted such that each element of the uterine assembly 300 (e.g., the first negative pressure port 310, the uterine expandable member 320, the second negative pressure port 330, etc.) is in a patient-specific position. Alternatively or in addition, the second extendible member 340 may be adjusted to suit specific anatomy (e.g., uterine cavity dimensions) of each patient.

In example embodiments, the second extendible member 340 may be formed in any shape, form, size, and/or dimension (e.g., tubular shaped member, cylindrical shaped member, hollow shaped member, square tube shaped member, etc.).

The Manipulator Assembly (e.g., Manipulator Assembly 400).

Figure 6G:
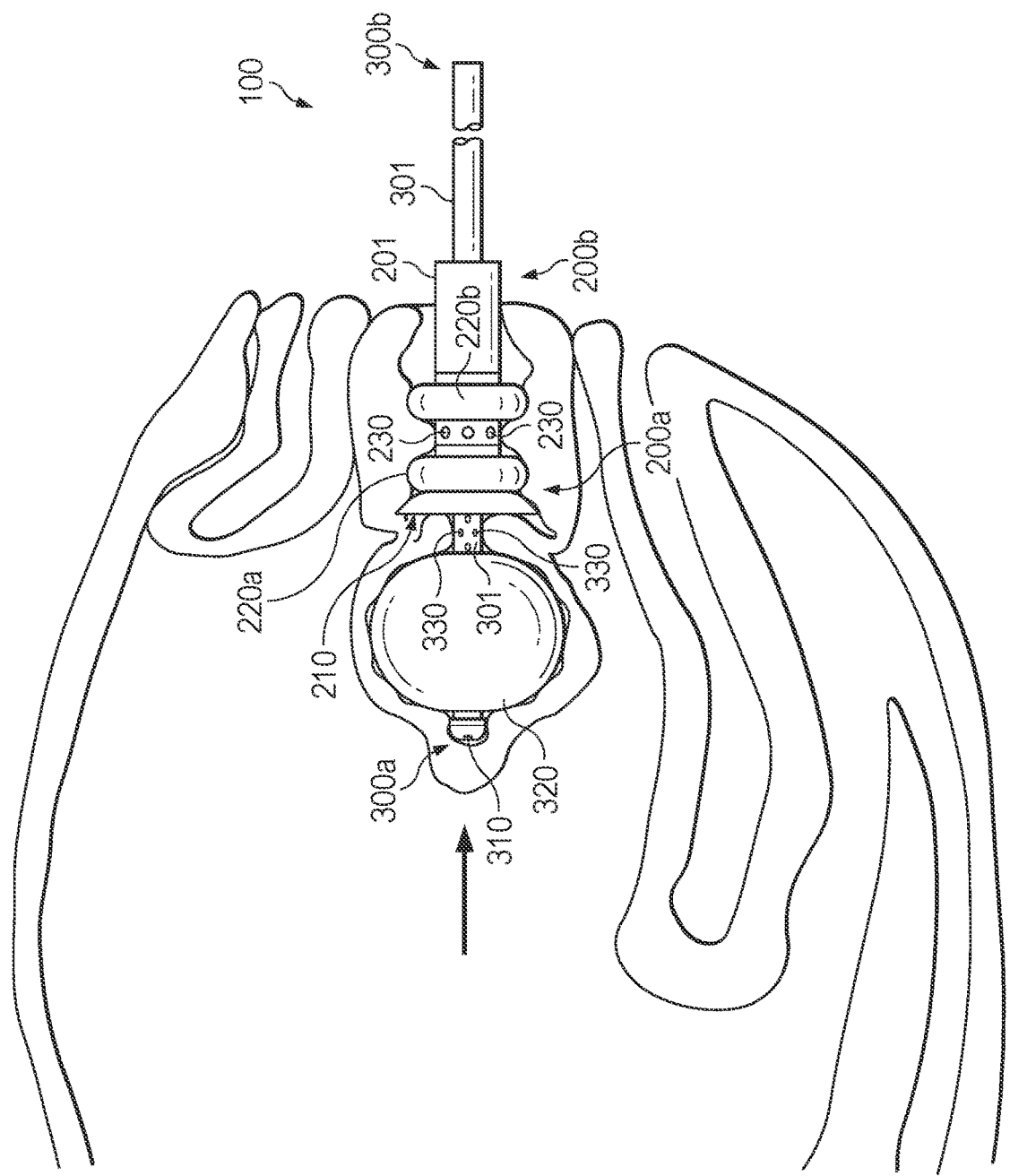
FIG. 6G is an illustration of an example embodiment of a hysteroscopic system having a main assembly (first, second, and third anchoring members in the anchoring state) anchored to a vaginal cavity of a patient and a uterine assembly (first negative pressure port, uterine expandable member, and second negative pressure port in the hemostasis state) anchored to a uterine cavity of the patient, wherein the anchored uterine assembly is moved relative to the anchored main assembly.
Figure 6H:
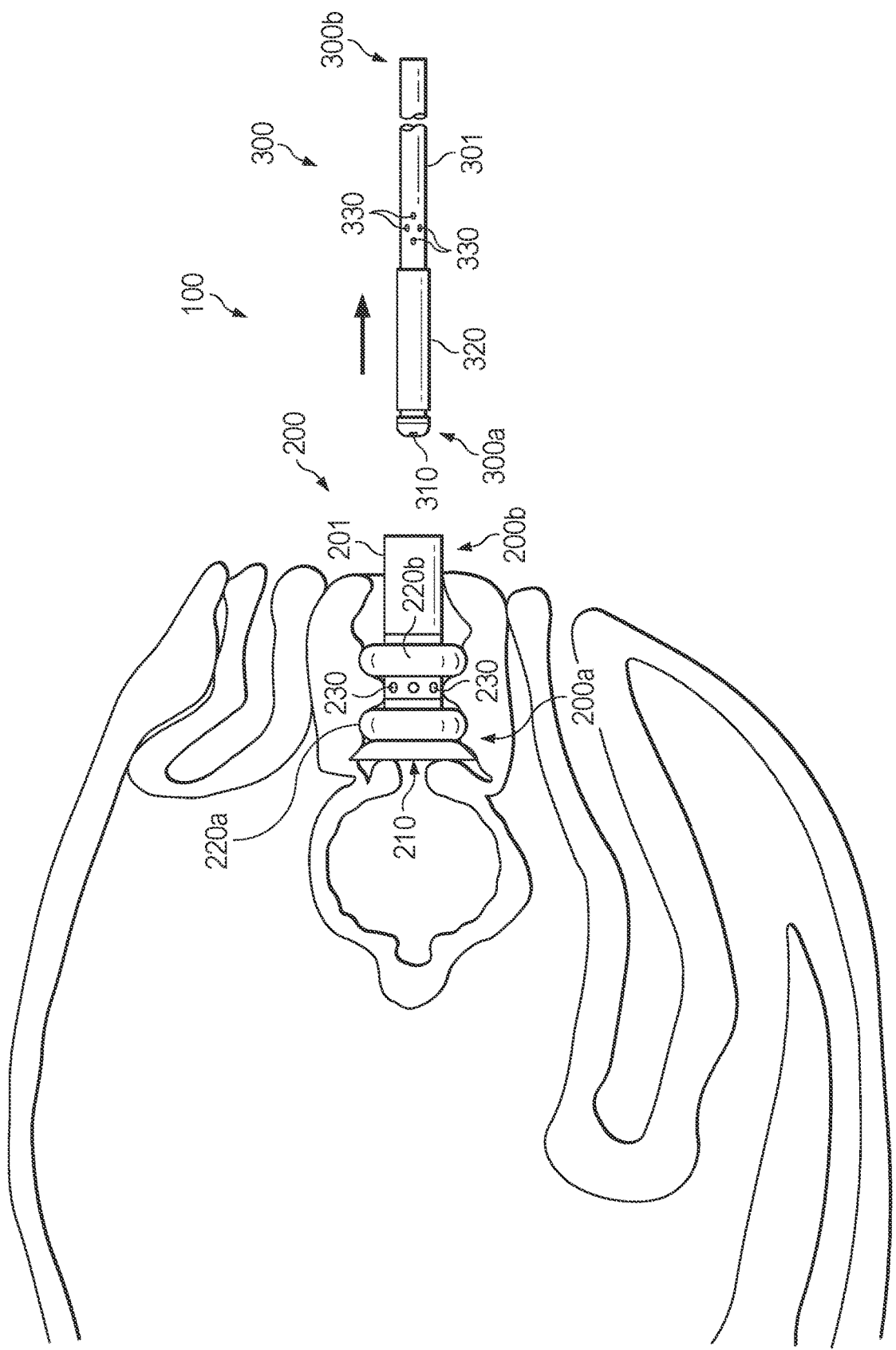
FIG. 6H is an illustration of an example embodiment of a hysteroscopic system having a main assembly (first, second, and third anchoring members in the anchoring state) anchored to a vaginal cavity of a patient and a uterine assembly (non-hemostasis state) being removed from uterine and vaginal cavities of the patient.
Figure 6I:
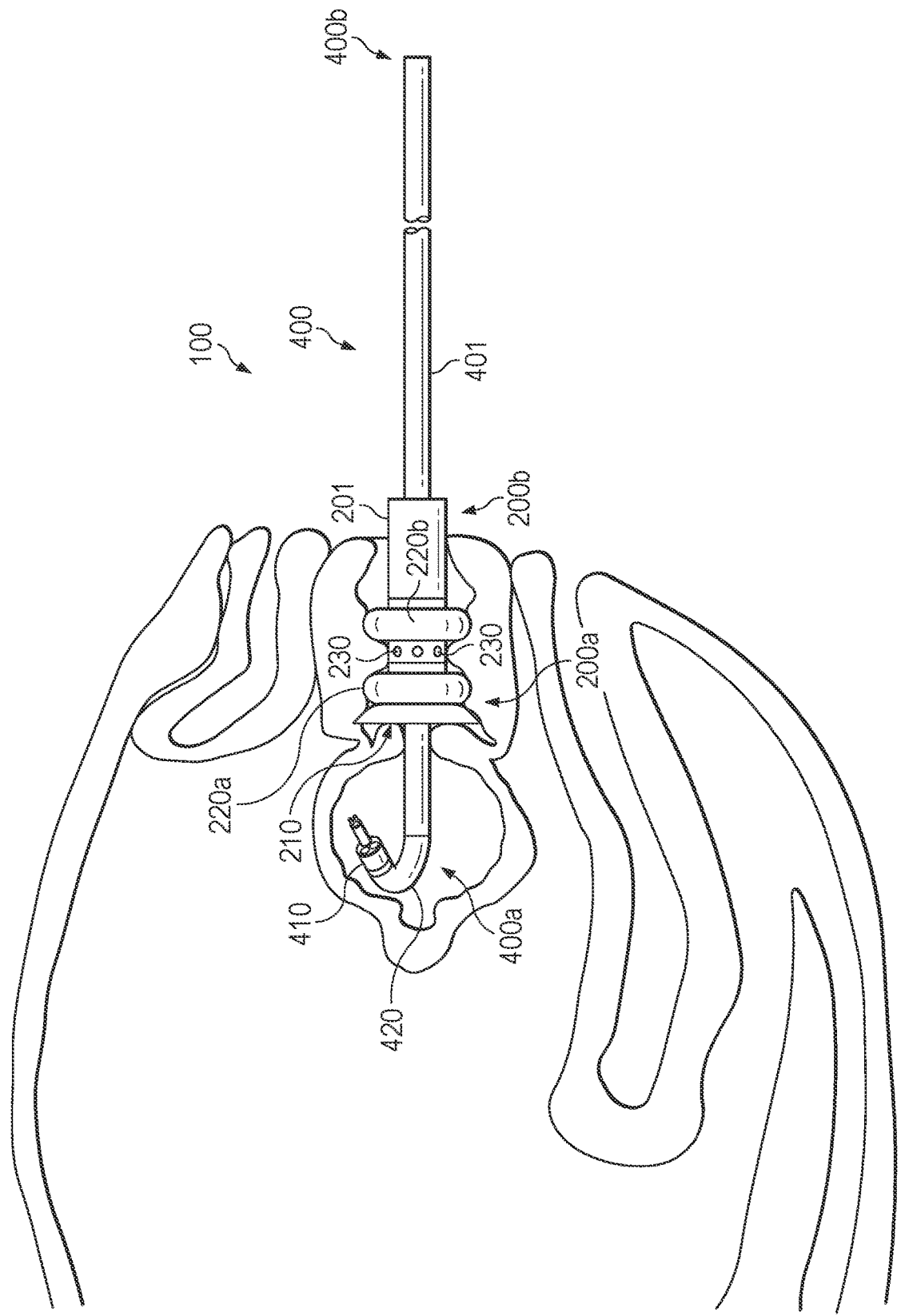
FIG. 6I is an illustration of an example embodiment of a hysteroscopic system having a main assembly (first, second, and third anchoring members in the anchoring state) anchored to a vaginal cavity of a patient and a manipulator assembly inserted into a uterine cavity of the patient to perform a surgical action in the uterine cavity of the patient.

As illustrated in at least FIG. 6I, an example embodiment of the hysteroscopic system 100 may further include a manipulator assembly (e.g., manipulator assembly 400). The manipulator assembly 400 may be configurable or configured to be inserted through and/or slidably housed in the main channel 202 of the main assembly 200.

The manipulator assembly 400 may be formed as an elongated body 401 having an in vivo end 400a and an in vitro end 400b. The manipulator assembly 400 may be inserted to mobilize in different positions of the uterine cavity. The manipulator assembly 400 includes one or more end effectors 410 for use in performing a surgical action (e.g., on one or more parts of the uterine cavity or uterine wall forming the uterine cavity of the patient).

The manipulator assembly 400 may also include one or more bendable sections 420. The bendable section 420 may be configurable or configured to facilitate a bending of the in vivo end 400a of the manipulator assembly 400 at one or more locations and in one or more directions. The bendable section 420 may be selectively adjusted to bend in multiple angles, directions, and locations along the bendable section 420 so as to adjustably direct as needed the end effector 410 relative to the patient's uterine cavity.

In example embodiments, the manipulator assembly 400 may include one or more extendible sections (not shown). The extendible section of the manipulator assembly 400 may be configurable or configured to selectively adjust or change a length of the manipulator assembly 400 (and/or a distance between the in vivo end 400a and the in vitro end 400b of the manipulator assembly 400).

The Controller (not Shown).

In an example embodiment, the hysteroscopic system 100 includes one or more controllers (not shown). The controller is configurable or configured to control and/or manage one or more elements of the hysteroscopic system 100 (as described in the present disclosure). The controller may perform such controlling and/or managing of one or more elements of the hysteroscopic system 100 by receiving instructions, commands, and/or actions from onsite and/or remote one or more surgeons or operators. Alternatively or in addition, the controller may perform such controlling and/or managing of one or more elements of the hysteroscopic system 100, in part or in whole, via artificial intelligence, or the like.

For example, the controller is configurable or configured to manage and/or control one or more elements of the main assembly 200. More specifically, the controller may be configurable or configured to transition the first anchoring member 220a between the anchoring state and the non-anchoring state. The controller may also be configurable or configured to transition the second anchoring member 220b between the anchoring state and the non-anchoring state. The controller may also be configurable or configured to transition the third anchoring member 230 between the anchoring state and the non-anchoring state. The controller may also be configurable or configured to transition the main assembly 200 between the anchoring state and the non-anchoring state. The controller may also be configurable or configured to actuate the extendible section 260 to extend and contract so as to change a length of the main assembly 200. The controller may also be configurable or configured to transition the locking member 240 between the locking state and the unlocking state. The controller may also be configurable or configured to cause the cervical seal member 210 to seal or hermetically seal the uterine cavity of the patient. The controller may also be configurable or configured to cause the vaginal seal member 250 to seal or hermetically seal the vaginal cavity of the patient. The controller may also be configurable or configured to position the main assembly 200 into the vaginal cavity of the patient, including removing the main assembly 200 from the vaginal cavity of the patient.

As another example, the controller is configurable or configured to manage and/or control one or more elements of the uterine assembly 300. More specifically, the controller may be configurable or configured to transition the first negative pressure port 310 between the hemostasis state and the non-hemostasis state. The controller may also be configurable or configured to transition the uterine expandable member 320 between the hemostasis state and the non-hemostasis state. The controller may also be configurable or configured to transition the second negative pressure port 330 between the hemostasis state and the non-hemostasis state. The controller may also be configurable or configured to transition the uterine assembly 300 between the hemostasis state and the non-hemostasis state. The controller may also be configurable or configured to actuate the bendable section 370 to bend in a plurality of directions, curvatures, and/or locations. The controller may also be configurable or configured to actuate the extendible section 340 to extend and contract so as to change a length of the uterine assembly 300. The controller may also be configurable or configured to transition the locking member of the uterine assembly between the locking state and the unlocking state. The controller may also be configurable or configured to position the in vivo end 300a of the uterine assembly 300 into the uterine cavity of the patient, including removing the uterine assembly 300 from the uterine cavity of the patient.

In yet another example, the controller is configurable or configured to manage and/or control one or more elements of the manipulator assembly 400. More specifically, the controller may be configurable or configured to actuate the end effector 410 to perform a surgical action. The controller may also be configurable or configured to actuate the bendable section 420 to bend in a plurality of directions, curvatures, and/or locations. The controller may also be configurable or configured to actuate an extendible section of the manipulator assembly 400 to extend and contract so as to change a length of the manipulator assembly 400. The controller may also be configurable or configured to position the in vivo end 400a of the manipulator assembly 400 into the uterine cavity of the patient, including removing the manipulator assembly 400 from the uterine cavity of the patient.

As used in the present disclosure, when applicable, the controller (and/or one or more of its elements) may include one or more computing devices, processors, servers, systems, cloud-based computing, or the like, and/or functionality of one or more processors, computing devices, servers, systems, cloud-based computing, or the like. The controller (and/or one or more of its elements) may be or have any processor, server, system, device, computing device, controller, microprocessor, microcontroller, microchip, semiconductor device, or the like, configurable or configured to perform one or more of the actions described above and in the present disclosure. Alternatively or in addition, the controller (and/or one or more of its elements) may include and/or be a part of a virtual machine, processor, computer, node, instance, host, or machine, including those in a networked computing environment.

Example Embodiments of a Method of Managing Post-Partum Hemorrhaging and/or a Method of Configuring a Hysteroscopic System to Manage Post-Partum Hemorrhaging.

As illustrated in at least FIGS. 6A-I, an example embodiment of a method of managing post-partum hemorrhaging (PPH) and/or a method of configuring a hysteroscopic system (e.g., hysteroscopic system 100) to manage PPH includes one or more actions performed using one or more elements of the hysteroscopic system 100.

For example, the method may include configuring a main assembly 200 to be in a non-anchoring state (as described in the present disclosure), if the main assembly 200 is not already in the non-anchoring state. The method may also include configuring a uterine assembly 300 to be in a non-hemostasis state (as described in the present disclosure), if the uterine assembly 300 is not already in the non-hemostasis state.

The method further includes configuring the uterine assembly 300 and main assembly 200 to be in a first insertion configuration by inserting the uterine assembly 300 into a main channel 202 of the main assembly 200 in such a way that at least a portion of the uterine assembly 300 is housed in the main channel 202 of the main assembly 200 (e.g., as illustrated in at least FIG. 6A). While in the first insertion configuration, at least a portion of an in vivo end 300a of the uterine assembly 300 may not be housed in the main channel 202. In example embodiments, the first insertion configuration may include transitioning a locking member 240 (and/or locking member of the uterine assembly 300, not shown) to a locking state so as to secure or lock the uterine assembly 300 relative to the main assembly 200 (as described in the present disclosure). It is to be understood that the locking member 240 (and/or locking member of the uterine assembly 300, not shown) may be transitioned to the locking state before and/or after both main assembly 200 and uterine assembly 300 are inserted into a vaginal cavity of the patient (and the in vivo end 300a of the uterine assembly is inserted into a uterine cavity of the patient). As illustrated in at least FIGS. 6A and 6B, the uterine assembly 300 and the main assembly 200 (while in the first insertion configuration) may then be introduced trans-vaginally into the vaginal cavity of the patient (and the in vivo end 300a of the uterine assembly introduced into a uterine cavity of the patient) until a cervical seal member 210, which is formed at the in vivo end 200a of the main assembly 200, is brought into contact with at least a portion of a cervix (and/or areas surrounding the cervix) of the patient (as illustrated in at least FIG. 6B).

Alternative to the first insertion configuration, the method may include first inserting the main assembly 200 into the vaginal cavity of the patient until the cervical seal member 210 is brought into contact with at least a portion of the cervix (and/or areas surrounding the cervix) of the patient. Thereafter, the method may include inserting the uterine assembly 300 through the main channel 202 of the main assembly 200 until the in vivo end 300a of the uterine assembly 300 passes through the main channel 202 (and is inserted into the uterine cavity of the patient, as illustrated in at least FIG. 6B). In example embodiments having the sealable member 216 sealable member for the vaginal seal member 250, the inserting of the uterine assembly 300 through the main channel 202 further includes inserting the in vivo end 300a of the uterine assembly 300 through the sealable member 216 and the sealable member of the vaginal seal member 250.

After the main assembly 200 is housed in the vaginal cavity of the patient and the in vivo end 300a of the uterine assembly 300 is housed in the uterine cavity of the patient (as illustrated in at least FIG. 6B), the method may include sealing or hermetically sealing the uterine cavity from the vaginal cavity of the patient via the cervical seal member 210. Alternatively or in addition, the cervical seal member 210 is configured to ensure that the main assembly 200 is properly positioned in the vaginal cavity of the patient, and to ensure that the main assembly 200 is not inserted into the uterine cavity of the patient.

The method may include transitioning the main assembly 200 to be in the anchoring state (as described in the present disclosure). As illustrated in at least FIG. 6C, this may include first transitioning the first anchoring member 220a to be in the anchoring state and transitioning the second anchoring member 220b to be in the anchoring state. As illustrated in at least FIG. 6D, the third anchoring member 230 may then be transitioned to be in the anchoring state, which enables or causes at least a portion of the vaginal cavity of the patient (and/or vaginal walls forming the vaginal cavity) to collapse towards the elongated body 201 of the main assembly 200 (i.e., towards the third anchoring member 230). In example embodiments, the first anchoring member 220a, second anchoring member 220b, and third anchoring member 230 are all transitioned to the anchoring state (and in the above order, or in any order).

After the main assembly 200 is transitioned to the anchoring state, the method includes transitioning the uterine assembly 300 to be in the hemostasis state (as described in the present disclosure). As illustrated in at least FIG. 6E, this may include transitioning the uterine expandable member 320 to be in the hemostasis state, transitioning the first negative pressure port 310 to be in the hemostasis state, and/or transitioning the second negative pressure port 330 to be in the hemostasis state. In example embodiments, the first negative pressure port 310, uterine expandable member 320, and second negative pressure port 330 are all transitioned to the hemostasis state. As illustrated in at least FIG. 6F, transitioning the uterine assembly 300 to be in the hemostasis state enables or causes at least a portion of the uterine cavity of the patient (and/or uterine wall forming the uterine cavity) to collapse towards the elongated body 301 of the uterine assembly 300 (i.e., towards the first negative pressure port 310, uterine expandable member 320, and second negative pressure port 330). In example embodiments, most or all of the uterine cavity of the patient (and/or uterine wall forming the uterine cavity) collapses towards and onto (or enveloping) at least the uterine expandable member 320 when the uterine assembly 300 is transitioned to the hemostasis state.

After the uterine assembly 300 is transitioned to the hemostasis state and the main assembly 200 is transitioned to the anchoring state, the method may include pulling or sliding the uterine assembly 300 (which remains in the hemostasis state) relative to the main assembly 200 (which remains in the anchoring state), as illustrated in at least FIG. 6G, so as to further manage or treat PPH (e.g., performing an accordioning of the uterine cavity of the patient (and/or uterine walls forming the uterine cavity)). In example embodiments in which the locking member 240 (and/or locking member of the uterine assembly 300) is provided and in the locking state, the method includes first transitioning the locking member 240 to the unlocking state.

The method further includes transitioning the uterine assembly 300 from the hemostasis state to the non-hemostasis state, including transitioning the uterine expandable member 320 to be in the non-hemostasis state, transitioning the first negative pressure port 310 to be in the non-hemostasis state, and/or transitioning the second negative pressure port 330 to be in the non-hemostasis state. As illustrated in at least FIG. 6H, the uterine assembly 300 is then pulled, removed, or withdrawn from the uterine cavity of the patient and the main channel 202 of the main assembly 200.

It is recognized in the present disclosure that after the uterine assembly 300 is transitioned to the non-hemostasis state, removed from the uterine cavity of the patient, and removed from the main channel 202 of the main assembly 200, the uterine cavity of the patient may remain in the same or similar shape as when the uterine assembly 300 was in the hemostasis state. In this regard, the method may include inserting a manipulator assembly 400 through the main channel 202 of the main assembly 200 in such a way that the end effector 410 of the manipulator assembly 400 can perform a surgical action in the uterine cavity of the patient (which can be properly positioned via bendable section 420, extendible section (not shown)). Although not shown, the manipulator assembly 400 may also include one or more imaging assemblies for use in enabling a surgeon to view inside the uterine cavity of the patient so as to perform the surgical actions with the end effector 410.

While various embodiments in accordance with the disclosed principles have been described above, it should be understood that they have been presented by way of example only, and are not limiting. Thus, the breadth and scope of the example embodiments described in the present disclosure should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

For example, "communication," "communicate," "connection," "connect," or other similar terms should generally be construed broadly to mean a wired, wireless, and/or other form of, as applicable, connection between elements, devices, computing devices, telephones, processors, controllers, servers, networks, telephone networks, the cloud, and/or the like, which enable voice and/or data to be sent, transmitted, broadcasted, received, intercepted, acquired, and/or transferred (each as applicable).

As another example, "seal", "sealing", "sealed", "sealable", or the like as referred herein should generally be construed broadly to mean to any actions including to close, cover, attach, fix, adhere, hinder, block, or obstruct and/or the like, which partly or substantially prevent, limit, interfere the activity or progress of the air or liquid, etc. to pass in or out.

As another example, "in vivo end" as referred herein should generally be construed broadly to mean a part that is inside an organism and more specifically to the part that is in or on the living tissue of a whole, living multicellular organism (animal), such as a mammal.

As another example, "in vitro end" as referred herein should generally be construed broadly to mean a part that is outside an organism and more specifically to the part that is not in or on the living tissue of a whole, living multicellular organism (animal), such as a mammal.

Various terms used herein have special meanings within the present technical field. Whether a particular term should be construed as such a "term of art" depends on the context in which that term is used. Such terms are to be construed in light of the context in which they are used in the present disclosure and as one of ordinary skill in the art would understand those terms in the disclosed context. The above definitions are not exclusive of other meanings that might be imparted to those terms based on the disclosed context.

Words of comparison, measurement, and timing such as "at the time," "equivalent," "during," "complete," and the like should be understood to mean "substantially at the time," "substantially equivalent," "substantially during," "substantially complete," etc., where "substantially" means that such comparisons, measurements, and timings are practicable to accomplish the implicitly or expressly stated desired result.

Additionally, the section headings and topic headings herein are provided for consistency with the suggestions under various patent regulations and practice, or otherwise to provide organizational cues. These headings shall not limit or characterize the embodiments set out in any claims that may issue from this disclosure. Specifically, a description of a technology in the "Background" is not to be construed as an admission that technology is prior art to any embodiments in this disclosure. Furthermore, any reference in this disclosure to "invention" in the singular should not be used to argue that there is only a single point of novelty in this disclosure. Multiple inventions may be set forth according to the limitations of the claims issuing from this disclosure, and such claims accordingly define the invention(s), and their equivalents, that are protected thereby. In all instances, the scope of such claims shall be considered on their own merits in light of this disclosure, but should not be constrained by the headings herein.

The invention claimed is:

1. A hysteroscopic system for managing post-partum hemorrhaging, the hysteroscopic system comprising:
   a main assembly, the main assembly formed as an elongated body having an in vivo end and an in vitro end, wherein, when in operation, the in vivo end of the main assembly is configured to be inserted into and housed in a vaginal cavity of a patient and the in vitro end of the main assembly is configured to remain outside of the vaginal cavity of the patient, the main assembly including:
- a main channel formed through the elongated body of the main assembly between the in vivo and in vitro ends of the main assembly, the main channel formed along a first central axis;
- a cervical seal member, the cervical seal member formed at the in vivo end of the main assembly and having a central axis coaxial to the first central axis, the cervical seal member having a contact wall and a non-contact wall opposite to the contact wall of the cervical seal member, the contact wall of the cervical seal member configured to contact with at least a portion of a cervix of the patient, the cervical seal member configured to hermetically isolate a uterine cavity of the patient from the vaginal cavity of the patient when: the contact wall of the cervical seal member is positioned to be in contact with at least a portion of the cervix of the patient;
- a first anchoring member, the first anchoring member formed on the elongated body of the main assembly and adjacent to the cervical seal member, the first anchoring member configured to transition between an anchoring state and a non-anchoring state, the anchoring state of the first anchoring member being a state in which the first anchoring member has a first overall volume, the non-anchoring state of the first anchoring member being a state in which the first anchoring member has a second overall volume, the first overall volume greater than the second overall volume;
- a second anchoring member, the second anchoring member configured to transition between an anchoring state and a non-anchoring state, the anchoring state of the second anchoring member being a state in which the second anchoring member has a third overall volume, the non-anchoring state of the second anchoring member being a state in which the second anchoring member has a fourth overall volume, the third overall volume greater than the fourth overall volume; and
- a third anchoring member, the third anchoring member formed between the first and second anchoring members, the third anchoring member configured to transition between an anchoring state and a non-anchoring state, the anchoring state of the third anchoring member being a state in which the third anchoring member applies at least a first negative pressure, the first negative pressure being an amount of negative pressure required to collapse at least a portion of the vaginal cavity towards the elongated body of the main assembly, the non-anchoring state of the third anchoring member being a state in which the third anchoring member does not apply at least the first negative pressure; and
- a uterine assembly, the uterine assembly formed as an elongated body having an in vivo end and an in vitro end, the uterine assembly configured to be slidably housed in the main channel of the main assembly in such a way that the in vivo end of the uterine assembly is extendible outwardly away from the in vivo end of the main assembly, the uterine assembly including:
  - a first negative pressure port, the first negative pressure port formed at a distal end of the in vivo end of the uterine assembly, the first negative pressure port configured to transition between a homeostasis state and a non-homeostasis state, the homeostasis state of the first negative pressure port being a state in which the first negative pressure port applies a negative pressure having a magnitude that is greater than or equal to a second negative pressure, the non-homeostasis state of the first negative pressure port being a state in which the first negative pressure port does not apply a negative pressure having a magnitude that is greater than or equal to the second negative pressure;
  - a uterine expandable member, the uterine expandable member formed on the elongated body of the uterine assembly and adjacent to the first negative pressure port, the uterine expandable member configured to transition between a homeostasis state and a non-homeostasis state, the homeostasis state of the uterine expandable member being a state in which the uterine expandable member has a third overall volume, the non-homeostasis state of the uterine expandable member being a state in which the uterine expandable member has a fourth overall volume, the third overall volume greater than the fourth overall volume; and
  - a second negative pressure port, the second negative pressure port formed adjacent to the uterine expandable member in such a way that the uterine expandable member is positioned between the first and second negative pressure ports, the second negative pressure port configured to transition between a homeostasis state and a non-homeostasis state, the homeostasis state of the second negative pressure port being a state in which the second negative pressure port applies a negative pressure having a magnitude that is greater than or equal to a third negative pressure, the non-homeostasis state of the second negative pressure port being a state in which the second negative pressure port does not apply a negative pressure having a magnitude that is greater than or equal to the third negative pressure, wherein the uterine assembly is configured to apply the second and third negative pressures in such a way that a combination of the second and third negative pressures is an amount of negative pressure required to collapse at least a portion of the uterine cavity towards the elongated body of the uterine assembly.

2. The hysteroscopic system of claim 1, wherein at least one of the following apply:
- the contact wall of the cervical seal member includes at least a portion that is formed in a concave shape; and/or
- the non-contact wall of the cervical seal member includes at least a portion that is formed in a convex shape; and/or
- the cervical seal member is formed along a plane that is substantially orthogonal to the first central axis; and/or
- the cervical seal member includes an outermost edge portion formed between the contact and non-contact walls of the cervical seal member, the outermost edge portion of the cervical seal member formed along a plane that is substantially orthogonal to the first central axis; and/or
- the contact wall of the cervical seal member includes a circular contact portion,
- the circular contact portion of the cervical seal member formed along a plane that is substantially orthogonal to the first central axis.

3. The hysteroscopic system of claim 1,
wherein the contact wall of the cervical seal member is formed having at least one flexible portion;
wherein the at least one flexible portion of the contact wall of the cervical seal member is configured to dynamically adapt to a surface topology of the cervix of the patient.

4. The hysteroscopic system of claim 1,
wherein the cervical seal member includes a sealable member formed at a center of the cervical seal member;
wherein the sealable member of the cervical seal member is coaxial to the first central axis; and
wherein the sealable member of the cervical seal member is configured to allow the in vivo end of the uterine assembly to slide through in both directions;
wherein the sealable member of the cervical seal member is configured to provide a hermetic seal around the uterine assembly when the uterine assembly is provided through the sealable member of the cervical seal member; and
wherein the sealable member of the cervical seal member is configured to hermetically seal itself when the uterine assembly is not provided through the sealable member of the cervical seal member.

5. The hysteroscopic system of claim 1, wherein at least one of the following apply:
wherein the cervical seal member is formed with sufficient rigidity that, when the third anchoring member applies the first negative pressure to collapse the at least one portion of the vaginal cavity towards the elongated body of the main assembly, the cervical seal member does not collapse or deform towards the third anchoring member; and/or
wherein, when the first anchoring member is transitioned to the anchoring state such that the first anchoring member has the first overall volume, the first anchoring member has sufficient rigidity so as to not collapse or deform towards the third anchoring member when the third anchoring member applies the first negative pressure to collapse the at least one portion of the vaginal cavity towards the elongated body of the main assembly; and/or
wherein, when the second anchoring member is transitioned to the anchoring state such that the second anchoring member has the third overall volume, the second anchoring member has sufficient rigidity so as to not collapse or deform towards the third anchoring member when the third anchoring member applies the first negative pressure to collapse the at least one portion of the vaginal cavity towards the elongated body of the main assembly.

6. The hysteroscopic system of claim 1, wherein at least one of the following apply:
wherein at least a portion of the in vivo end of the uterine assembly is configured to bend in one or more directions; and/or
wherein at least a portion of the in vivo end of the uterine assembly is configured to extend and contract so as to change a length of the in vivo end of the uterine assembly.

7. The hysteroscopic system of claim 1, further comprising:
a manipulator assembly, the manipulator assembly formed as an elongated body having an in vivo end and an in vitro end, the manipulator assembly configured to be slidably housed in the main channel of the main assembly when the uterine assembly is not housed in the main channel of the main assembly, the manipulator assembly including:
an end-effector, the end-effector provided at a distal most end of the in vivo end of the manipulator assembly, the end-effector configurable to perform a surgical action.

8. The hysteroscopic system of claim 7, wherein at least one of the following apply:
wherein at least a portion of the in vivo end of the manipulator assembly is configured to bend in one or more directions; and/or
wherein at least a portion of the in vivo end of the manipulator assembly is configured to extend and contract so as to change a length of the in vivo end of the manipulator assembly.

9. The hysteroscopic system of claim 1, further comprising:
a locking member, the locking member configured to transition between a locking state and an unlocking state such that, when in the locking state, the locking member is configured to lock movement of the uterine assembly relative to the main assembly when the uterine assembly is inserted through the main channel of the main assembly.

10. The hysteroscopic system of claim 9, wherein the locking member includes:
a main locking body, the main locking body rotatable in one or more directions so as to transition between the unlocking state and the locking state; and/or
a locking actuator, the locking actuator configured to transition between the locking state and the unlocking state when the main locking body is rotated.

11. The hysteroscopic system of claim 1, further comprising a controller, the controller configurable to perform at least one of the following:
adjust a position of the main assembly in such a way that the contact wall of the cervical seal member is positioned to be in contact with the at least one portion of the cervix of the patient; and/or
transition the first anchoring member between the anchoring state and the non-anchoring state; and/or
transition the second anchoring member between the anchoring state and the non-anchoring state; and/or
transition the third anchoring member between the anchoring state and the non-anchoring state; and/or
transition the first negative pressure port between the homeostasis state and the non-homeostasis state; and/or
transition the uterine expandable member between the homeostasis state and the non-homeostasis state; and/or
transition the second negative pressure port between the homeostasis state and the non-homeostasis state.

12. A hysteroscopic system for managing post-partum hemorrhaging, the hysteroscopic system comprising:
a main assembly, the main assembly formed as an elongated body having an in vivo end and an in vitro end, the in vivo end of the main assembly configured to be inserted into and housed in a vaginal cavity of a patient, the in vitro end of the main assembly configured to remain outside of the vaginal cavity of the patient, the main assembly including:
a main channel formed through the elongated body of the main assembly between the in vivo and in vitro ends of the main assembly, the main channel formed along a first central axis;
a first anchoring member, the first anchoring member formed on the elongated body of the main assembly, the first anchoring member configured to transition between an anchoring state and a non-anchoring state, the anchoring state of the first anchoring member being a state in which the first anchoring member is expanded away from the elongated body of the main assembly;

a second anchoring member, the second anchoring member configured to transition between an anchoring state and a non-anchoring state, the anchoring state of the second anchoring member being a state in which the second anchoring member is expanded away from the elongated body of the main assembly; and a vaginal seal member, the vaginal seal member formed at the in vitro end of the main assembly and having a central axis coaxial to the first central axis, the vaginal seal member having a contact wall and a non-contact wall opposite to the contact wall, the contact wall of the vaginal seal member configured to contact with at least a portion of a vulva of the patient, the vaginal seal member configured to hermetically isolate the vaginal cavity of the patient when: the contact wall of the vaginal seal member is positioned to be in contact with at least a portion of the vulva of the patient; and a third anchoring member, the third anchoring member formed between the first and second anchoring members, the third anchoring member configured to transition between an anchoring state and a non-anchoring state, the anchoring state of the third anchoring member being a state in which the third anchoring member applies at least a first negative pressure; and a uterine assembly, the uterine assembly formed as an elongated body having an in vivo end and an in vitro end, the uterine assembly configured to be slidably housed in the main channel of the main assembly, the uterine assembly including:

a first negative pressure port, the first negative pressure port formed at a distal end of the in vivo end of the uterine assembly, the first negative pressure port configured to transition between a homeostasis state and a non-homeostasis state, the homeostasis state of the first negative pressure port being a state in which the first negative pressure port applies at least a second negative pressure;

a uterine expandable member, the uterine expandable member formed on the elongated body of the uterine assembly and adjacent to the first negative pressure port, the uterine expandable member configured to transition between a homeostasis state and a non-homeostasis state, the homeostasis state of the uterine expandable member being a state in which the uterine expandable member is expanded away from the elongated body of the uterine assembly; and a second negative pressure port, the second negative pressure port formed adjacent to the uterine expandable member in such a way that the uterine expandable member is positioned between the first and second negative pressure ports, the second negative pressure port configured to transition between a homeostasis state and a non-homeostasis state, the homeostasis state of the second negative pressure port being a state in which the second negative pressure port applies at least a third negative pressure.

13. The hysteroscopic system of claim 12, wherein at least one of the following apply:

the contact wall of the vaginal seal member includes at least a portion that is formed in a concave shape; and/or the non-contact wall of the vaginal seal member includes at least a portion that is formed in a convex shape; and/or the vaginal seal member is formed along a plane that is substantially orthogonal to the first central axis; and/or the vaginal seal member includes an outermost edge portion formed between the contact and non-contact walls of the vaginal seal member, the outermost edge portion of the vaginal seal member formed along a plane that is substantially orthogonal to the first central axis; and/or the contact wall of the vaginal seal member includes a circular contact portion, the circular contact portion of the vaginal seal member formed along a plane that is substantially orthogonal to the first central axis.

14. The hysteroscopic system of claim 12, wherein the contact wall of the vaginal seal member is formed having at least one flexible portion;

wherein the at least one flexible portion of the contact wall of the vaginal seal member is configured to dynamically adapt to a surface topology of an area surrounding the vulva of the patient.

15. The hysteroscopic system of claim 12, wherein the vaginal seal member includes an opening formed at a center of the vaginal seal member;

wherein the opening of the vaginal seal member is coaxial to the first central axis;

wherein the opening of the vaginal seal member is configured to allow the in vivo end of the uterine assembly to slide through in both directions;

wherein the opening of the vaginal seal member is configured to provide a hermetic seal around the uterine assembly when the uterine assembly is provided through the opening of the vaginal seal member; and wherein the opening of the vaginal seal member is configured to hermetically seal itself when the uterine assembly is not provided through the opening of the vaginal seal member.

16. The hysteroscopic system of claim 12, wherein at least one of the following apply:

wherein at least a portion of the in vivo end of the uterine assembly is configured to bend in one or more directions;

wherein at least a portion of the in vivo end of the uterine assembly is configured to extend and contract so as to change a length of the in vivo end of the uterine assembly;

wherein the uterine assembly is configured to apply the second and third negative pressures in such a way that a combination of the second and third negative pressures is an amount of negative pressure required to collapse at least a portion of the uterine cavity towards the elongated body of the uterine assembly.

17. The hysteroscopic system of claim 12, further comprising:

a manipulator assembly, the manipulator assembly formed as an elongated body having an in vivo end and an in vitro end, the manipulator assembly configured to be slidably housed in the main channel of the main assembly when the uterine assembly is not housed in the main channel of the main assembly, the manipulator assembly including:

an end-effector, the end-effector provided at a distal most end of the in vivo end of the manipulator assembly, the end-effector configurable to perform a surgical action.

18. The hysteroscopic system of claim 17, wherein at least a portion of the in vivo end of the manipulator assembly is configured to bend in one or more directions.

19. The hysteroscopic system of claim 17, wherein at least a portion of the in vivo end of the manipulator assembly is configured to extend and contract so as to change a length of the in vivo end of the manipulator assembly.

20. The hysteroscopic system of claim 12, further comprising a controller, the controller configurable to perform at least one of the following:
adjust a position of the main assembly in such a way that the contact wall of the vaginal seal member is positioned to be in contact with the at least one portion of the vulva of the patient; and/or
transition the first anchoring member between the anchoring state and the non-anchoring state; and/or
transition the second anchoring member between the anchoring state and the non-anchoring state; and/or
transition the third anchoring member between the anchoring state and the non-anchoring state; and/or
transition the first negative pressure port between the homeostasis state and the non-homeostasis state; and/or
transition the uterine expandable member between the homeostasis state and the non-homeostasis state; and/or
transition the second negative pressure port between the homeostasis state and the non-homeostasis state; and/or
apply the second and third negative pressures in such a way that a combination of the second and third negative pressures is an amount of negative pressure required to collapse at least a portion of the uterine cavity towards the elongated body of the uterine assembly.

21. A hysteroscopic system for managing post-partum hemorrhaging, the hysteroscopic system comprising:
a main assembly, the main assembly formed as an elongated body having an in vivo end and an in vitro end, wherein, when in operation, the in vivo end of the main assembly is configured to be inserted into and housed in a vaginal cavity of a patient and the in vitro end of the main assembly is configured to remain outside of the vaginal cavity of the patient, the main assembly including:
a main channel formed through the elongated body of the main assembly between the in vivo and in vitro ends of the main assembly, the main channel formed along a first central axis;
a cervical seal member, the cervical seal member formed at the in vivo end of the main assembly and having a central axis coaxial to the first central axis, the cervical seal member having a contact wall and a non-contact wall opposite to the contact wall of the cervical seal member, the contact wall of the cervical seal member configured to contact with at least a portion of a cervix of the patient, the cervical seal member configured to hermetically isolate a uterine cavity of the patient from the vaginal cavity of the patient when: the contact wall of the cervical seal member is positioned to be in contact with at least a portion of the cervix of the patient;
a first anchoring member, the first anchoring member formed on the elongated body of the main assembly and adjacent to the cervical seal member, the first anchoring member configured to transition between an anchoring state and a non-anchoring state, the anchoring state of the first anchoring member being a state in which the first anchoring member has a first overall volume, the non-anchoring state of the first anchoring member being a state in which the first anchoring member has a second overall volume, the first overall volume greater than the second overall volume;
a second anchoring member, the second anchoring member configured to transition between an anchoring state and a non-anchoring state, the anchoring state of the second anchoring member being a state in which the second anchoring member has a third overall volume, the non-anchoring state of the second anchoring member being a state in which the second anchoring member has a fourth overall volume, the third overall volume greater than the fourth overall volume;
a third anchoring member, the third anchoring member formed between the first and second anchoring members, the third anchoring member configured to transition between an anchoring state and a non-anchoring state, the anchoring state of the third anchoring member being a state in which the third anchoring member applies at least a first negative pressure, the first negative pressure being an amount of negative pressure required to collapse at least a portion of the vaginal cavity towards the elongated body of the main assembly, the non-anchoring state of the third anchoring member being a state in which the third anchoring member does not apply at least the first negative pressure; and
a vaginal seal member, the vaginal seal member formed at the in vitro end of the main assembly and having a central axis coaxial to the first central axis, the vaginal seal member having a contact wall and a non-contact wall opposite to the contact wall, the contact wall of the vaginal seal member configured to contact with at least a portion of a vulva of the patient, the vaginal seal member configured to hermetically isolate the vaginal cavity of the patient when: the contact wall of the vaginal seal member is positioned to be in contact with at least a portion of the vulva of the patient; and
a uterine assembly, the uterine assembly formed as an elongated body having an in vivo end and an in vitro end, the uterine assembly configured to be slidably housed in the main channel of the main assembly in such a way that the in vivo end of the uterine assembly is extendible outwardly away from the in vivo end of the main assembly, the uterine assembly including:
a first negative pressure port, the first negative pressure port formed at a distal end of the in vivo end of the uterine assembly, the first negative pressure port configured to transition between a homeostasis state and a non-homeostasis state, the homeostasis state of the first negative pressure port being a state in which the first negative pressure port applies a negative pressure having a magnitude that is greater than or equal to a second negative pressure, the non-homeostasis state of the first negative pressure port being a state in which the first negative pressure port does not apply a negative pressure having a magnitude that is greater than or equal to the second negative pressure;
a uterine expandable member, the uterine expandable member formed on the elongated body of the uterine assembly and adjacent to the first negative pressure port, the uterine expandable member configured to transition between a homeostasis state and a non-homeostasis state, the homeostasis state of the uterine expandable member being a state in which the uterine expandable member has a third overall volume, the non-homeostasis state of the uterine expandable member being a state in which the uterine expandable member has a fourth overall volume, the third overall volume greater than the fourth overall volume; and a second negative pressure port, the second negative pressure port formed adjacent to the uterine expandable member in such a way that the uterine expandable member is positioned between the first and second negative pressure ports, the second negative pressure port configured to transition between a homeostasis state and a non-homeostasis state, the homeostasis state of the second negative pressure port being a state in which the second negative pressure port applies a negative pressure having a magnitude that is greater than or equal to a third negative pressure, the non-homeostasis state of the second negative pressure port being a state in which the second negative pressure port does not apply a negative pressure having a magnitude that is greater than or equal to the third negative pressure.

22. The hysteroscopic system of claim 21, wherein at least one of the following apply:

the contact wall of the cervical seal member includes at least a portion that is formed in a concave shape; and/or the non-contact wall of the cervical seal member includes at least a portion that is formed in a convex shape; and/or the contact wall of the vaginal seal member includes at least a portion that is formed in a concave shape; and/or the non-contact wall of the vaginal seal member includes at least a portion that is formed in a convex shape; and/or the cervical seal member is formed along a plane that is substantially orthogonal to the first central axis; and/or the cervical seal member includes an outermost edge portion formed between the contact and non-contact walls of the cervical seal member, the outermost edge portion of the cervical seal member formed along a plane that is substantially orthogonal to the first central axis; and/or the contact wall of the cervical seal member includes a circular contact portion, the circular contact portion of the cervical seal member formed along a plane that is substantially orthogonal to the first central axis; and/or the vaginal seal member is formed along a plane that is substantially orthogonal to the first central axis; and/or the vaginal seal member includes an outermost edge portion formed between the contact and non-contact walls of the vaginal seal member, the outermost edge portion of the vaginal seal member formed along a plane that is substantially orthogonal to the first central axis; and/or the contact wall of the vaginal seal member includes a circular contact portion, the circular contact portion of the vaginal seal member formed along a plane that is substantially orthogonal to the first central axis.

23. The hysteroscopic system of claim 21, wherein the contact wall of the cervical seal member is formed having at least one flexible portion;

wherein the at least one flexible portion of the contact wall of the cervical seal member is configured to dynamically adapt to a surface topology of the cervix of the patient;

wherein the contact wall of the vaginal seal member is formed having at least one flexible portion;

wherein the at least one flexible portion of the contact wall of the vaginal seal member is configured to dynamically adapt to a surface topology of an area surrounding the vulva of the patient.

24. The hysteroscopic system of claim 21, wherein the cervical seal member includes a sealable member formed at a center of the cervical seal member;

wherein the sealable member of the cervical seal member is coaxial to the first central axis;

wherein the sealable member of the cervical seal member is configured to allow the in vivo end of the uterine assembly to slide through in both directions;

wherein the sealable member of the cervical seal member is configured to provide a hermetic seal around the uterine assembly when the uterine assembly is provided through the sealable member of the cervical seal member;

wherein the sealable member of the cervical seal member is configured to hermetically seal itself when the uterine assembly is not provided through the sealable member of the cervical seal member.

25. The hysteroscopic system of claim 21, wherein the vaginal seal member includes an opening formed at a center of the vaginal seal member;

wherein the opening of the vaginal seal member is coaxial to the first central axis;

wherein the opening of the vaginal seal member is configured to allow the in vivo end of the uterine assembly to slide through in both directions;

wherein the opening of the vaginal seal member is configured to provide a hermetic seal around the uterine assembly when the uterine assembly is provided through the opening of the vaginal seal member; and wherein the opening of the vaginal seal member is configured to hermetically seal itself when the uterine assembly is not provided through the opening of the vaginal seal member.

26. The hysteroscopic system of claim 21, wherein at least one of the following apply:

wherein the cervical seal member is formed with sufficient rigidity that, when the third anchoring member applies the first negative pressure to collapse the at least one portion of the vaginal cavity towards the elongated body of the main assembly, the cervical seal member does not collapse or deform towards the third anchoring member; and/or wherein, when the first anchoring member is transitioned to the anchoring state such that the first anchoring member has the first overall volume, the first anchoring member has sufficient rigidity so as to not collapse or deform towards the third anchoring member when the third anchoring member applies the first negative pressure to collapse the at least one portion of the vaginal cavity towards the elongated body of the main assembly; and/or wherein, when the second anchoring member is transitioned to the anchoring state such that the second anchoring member has the third overall volume, the second anchoring member has sufficient rigidity so as to not collapse or deform towards the third anchoring member when the third anchoring member applies the first negative pressure to collapse the at least one portion of the vaginal cavity towards the elongated body of the main assembly; and/or wherein at least a portion of the in vivo end of the uterine assembly is configured to bend in one or more directions; and/or wherein at least a portion of the in vivo end of the uterine assembly is configured to extend and contract so as to change a length of the in vivo end of the uterine assembly.

27. The hysteroscopic system of claim 21, further comprising:
   a manipulator assembly, the manipulator assembly formed as an elongated body having an in vivo end and an in vitro end, the manipulator assembly configured to be slidably housed in the main channel of the main assembly when the uterine assembly is not housed in the main channel of the main assembly, the manipulator assembly including:
   an end-effector, the end-effector provided at a distal most end of the in vivo end of the manipulator assembly, the end-effector configurable to perform a surgical action.

28. The hysteroscopic system of claim 27, wherein at least one of the following apply:
   wherein at least a portion of the in vivo end of the manipulator assembly is configured to bend in one or more directions; and/or
   wherein at least a portion of the in vivo end of the manipulator assembly is configured to extend and contract so as to change a length of the in vivo end of the manipulator assembly.

29. The hysteroscopic system of claim 21, further comprising a controller, the controller configurable to perform at least one of the following:
   adjust a position of the main assembly in such a way that the contact wall of the cervical seal member is positioned to be in contact with the at least one portion of the cervix of the patient; and/or
   transition the first anchoring member between the anchoring state and the non-anchoring state; and/or
   transition the second anchoring member between the anchoring state and the non-anchoring state; and/or
   transition the third anchoring member between the anchoring state and the non-anchoring state; and/or
   transition the first negative pressure port between the homeostasis state and the non-homeostasis state; and/or
   transition the uterine expandable member between the homeostasis state and the non-homeostasis state; and/or
   transition the second negative pressure port between the homeostasis state and the non-homeostasis state; and/or
   apply the second and third negative pressures in such a way that a combination of the second and third negative pressures is an amount of negative pressure required to collapse at least a portion of the uterine cavity towards the elongated body of the uterine assembly.

* * * * *